US010232044B2

(12) United States Patent
Lichter et al.

(10) Patent No.: US 10,232,044 B2
(45) Date of Patent: *Mar. 19, 2019

(54) CONTROLLED RELEASE AURAL PRESSURE MODULATOR COMPOSITIONS AND METHODS FOR THE TREATMENT OF OTIC DISORDERS

(71) Applicants: Otonomy, Inc., San Diego, CA (US); The Regents of the University of California, Oakland, CA (US)

(72) Inventors: Jay Lichter, Rancho Santa Fe, CA (US); Andrew M. Trammel, Olathe, KS (US); Fabrice Piu, San Diego, CA (US); Qiang Ye, San Diego, CA (US); Michael Christopher Scaife, Los Altos, CA (US); Benedikt Vollrath, San Diego, CA (US); Sergio G. Duron, San Diego, CA (US); Luis A. Dellamary, San Marcos, CA (US); Carl Lebel, Malibu, CA (US); Jeffrey P. Harris, La Jolla, CA (US)

(73) Assignees: OTONOMY, INC., San Diego, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 193 days.

This patent is subject to a terminal disclaimer.

(21) Appl. No.: 14/465,153

(22) Filed: Aug. 21, 2014

(65) Prior Publication Data

US 2014/0364510 A1   Dec. 11, 2014

Related U.S. Application Data

(63) Continuation of application No. 12/486,697, filed on Jun. 17, 2009, now Pat. No. 8,846,770.

(60) Provisional application No. 61/073,716, filed on Jun. 18, 2008, provisional application No. 61/074,583, filed on Jun. 20, 2008, provisional application No. 61/082,450, filed on Jul. 21, 2008, provisional application No. 61/086,105, filed on Aug. 4, 2008, provisional application No. 61/094,384, filed on Sep. 4, 2008, provisional application No. 61/101,112, filed on Sep. 29, 2008, provisional application No. 61/140,033, filed on Dec. 22, 2008.

(51) Int. Cl.
*A61K 31/724* (2006.01)
*A61K 47/34* (2017.01)
*A61K 9/14* (2006.01)
*A61K 31/5377* (2006.01)
*A61K 31/5517* (2006.01)

(52) U.S. Cl.
CPC .............. *A61K 47/34* (2013.01); *A61K 9/14* (2013.01); *A61K 31/5377* (2013.01); *A61K 31/5517* (2013.01); *A61K 31/724* (2013.01)

(58) Field of Classification Search
CPC ............ A61K 31/5377; A61K 31/5517; A61K 31/724; A61K 47/34; A61K 9/14
See application file for complete search history.

(56) References Cited

U.S. PATENT DOCUMENTS

| | | |
|---|---|---|
| 5,503,848 A | 4/1996 | Perbellini et al. |
| 5,861,174 A | 1/1999 | Stratton et al. |
| 6,177,434 B1 | 1/2001 | Kopke et al. |
| 6,287,588 B1 * | 9/2001 | Shih ............... A61K 47/34 424/426 |
| 6,316,011 B1 | 11/2001 | Ron et al. |
| 6,392,036 B1 | 5/2002 | Karlsson et al. |
| 6,649,621 B2 | 11/2003 | Kopke et al. |
| 6,740,664 B2 | 5/2004 | Cagle et al. |
| 7,524,834 B2 | 4/2009 | Karlsson et al. |
| 8,349,353 B2 | 1/2013 | Lichter et al. |
| 8,399,018 B2 | 3/2013 | Lichter et al. |
| 8,496,957 B2 | 7/2013 | Lichter et al. |
| 8,648,119 B2 | 2/2014 | Lichter et al. |
| 8,784,870 B2 | 7/2014 | Lichter et al. |
| 8,846,770 B2 | 9/2014 | Lichter et al. |
| 2001/0044584 A1 * | 11/2001 | Kensey ............. A61B 5/02028 600/504 |
| 2003/0229333 A1 | 12/2003 | Ashton et al. |
| 2004/0082509 A1 | 4/2004 | Bonny |

(Continued)

FOREIGN PATENT DOCUMENTS

WO   WO 9524430 A2 *  9/1995  ............... A61K 8/91
WO   WO 1997/038698   10/1997

(Continued)

OTHER PUBLICATIONS

Chen et al. In vivo Distribution and Pharmacokinetics of Dexamethasone Acetate Nanoparticles Thermosensitive in situ Gel Following Intratympanic Injection. Chin. J. Otorhinolaryngol Head Neck Surg 42:533-534 (2007).

Chen et al. Preliminary study on brain-targeted drug delivery via inner ear. Acta Pharmaceutica Sinica 42:1102-1106 (2007) (English Abstract).

Feng et al. Effect of Poloxamer 407 on the cochlear orphology and hearing function after perfusion in round window: experiment with guinea pigs. National Medical Journal of China 87:2289-2291 (2007) (English Translation).

(Continued)

*Primary Examiner* — Sarah Pihonak
(74) *Attorney, Agent, or Firm* — Wilson Sonsini Goodrich & Rosati

(57) ABSTRACT

Disclosed herein are compositions and methods for the treatment of otic diseases or conditions with aural pressure modulating agent compositions and formulations administered locally to an individual afflicted with an otic disease or condition, through direct application of these compositions and formulations onto or via perfusion into the targeted auris structure(s).

16 Claims, 4 Drawing Sheets

(56) References Cited

U.S. PATENT DOCUMENTS

| | | | |
|---|---|---|---|
| 2004/0151753 A1* | 8/2004 | Chen | A61K 9/0024 424/426 |
| 2005/0118206 A1* | 6/2005 | Luk | A61K 9/0024 424/400 |
| 2005/0147585 A1 | 7/2005 | Schwarz | |
| 2005/0214338 A1 | 9/2005 | Guitton et al. | |
| 2006/0013858 A1 | 1/2006 | Trune | |
| 2006/0046970 A1 | 3/2006 | Bowman et al. | |
| 2006/0063802 A1 | 3/2006 | Guitton et al. | |
| 2006/0264897 A1 | 11/2006 | Lobl et al. | |
| 2006/0269602 A1 | 11/2006 | Dasch et al. | |
| 2007/0110788 A1 | 5/2007 | Hissong et al. | |
| 2007/0178051 A1 | 8/2007 | Pruitt et al. | |
| 2009/0297533 A1 | 12/2009 | Lichter et al. | |
| 2009/0306225 A1 | 12/2009 | Lichter et al. | |
| 2009/0324552 A1 | 12/2009 | Lichter et al. | |
| 2009/0325938 A1 | 12/2009 | Lichter et al. | |
| 2010/0004225 A1 | 1/2010 | Lichter et al. | |
| 2010/0009952 A1 | 1/2010 | Lichter et al. | |
| 2010/0015228 A1 | 1/2010 | Lichter et al. | |
| 2010/0016218 A1 | 1/2010 | Lichter et al. | |
| 2010/0016450 A1 | 1/2010 | Lichter et al. | |
| 2010/0021416 A1 | 1/2010 | Lichter et al. | |
| 2010/0022661 A1 | 1/2010 | Lichter et al. | |
| 2010/0036000 A1 | 2/2010 | Lichter et al. | |
| 2010/0197800 A1 | 8/2010 | Friedman et al. | |
| 2010/0015263 A1 | 12/2010 | Lichter et al. | |

FOREIGN PATENT DOCUMENTS

| | | |
|---|---|---|
| WO | WO 1999/024051 | 5/1999 |
| WO | WO 2002/056890 | 7/2002 |
| WO | WO 2003/017990 | 3/2003 |
| WO | WO 2003/034979 | 5/2003 |
| WO | WO 2003/071986 | 9/2003 |
| WO | WO 2007/031098 | 3/2007 |
| WO | WO 2007/031280 | 3/2007 |
| WO | WO 2007/038949 | 4/2007 |
| WO | WO 2008/001341 | 1/2008 |
| WO | WO 2008/076556 | 6/2008 |

OTHER PUBLICATIONS

Pappas et al. Topical Antibiotic Ear Drops: Are They Safe? Int J Clin Pract. 60:1115-1119 (2006).
Ross et al. Aqueous Solubilities of some variously Substituted Quinolone Antimicrobials. Int'l J of Pharm 63:237-250 (1990).
Ahn et al. Lipoic acid rescues DBA mice from early-onset age-related hearing impairment. Neuroreport 19(13):1265-1269. 2008.
Arnold et al. Novel slow- and fast-type drug release round-window microimplants for local drug application to the cochlea: an experimental study in guinea pigs. Audiol Neurootol 10(1):53-63. 2005.
Auris Medical. press release reporting initiating of phase I/II clinical trial with AM-101 Feb. 22, 2007.
Auris Medical. press release reporting results of phase I/II clinical trial with AM-111. Jun. 21, 2006.
Battaglia et al.. Combination therapy (intratympanic dexamethasone + high-dose prednisone taper) for the treatment of idiopathic sudden sensorineural hearing loss. Otol Neurotol 29(4):453-460. 2008.
Campbell et al. Oral-D-methionine (MRX-1024) significantly protects against cisplatin-induced hearing loss: a phase II study in humans. Abst 32nd Ann MidWinter Res Meeting. ARO Abstracts 32:7. Feb. 14-19, 2009.
Chen et al. Estrogen-related receptor beta/NR3B2 controls epithelial cell fate and endolymph production by the stria vascularis. Dev Cell 13(3):325-337. 2007.
Chen et al. Design and preparation of thermosensitive in situ gel of dexamethasone sodium phosphate. J Guangdong Coll Pharm 23(5):518-521. 2007 (English abstract).
Chen et al. Evaluation of thermosensitive in situ gel using dynamic rheological experiment. Chin Pharm J 43(6):444-447. 2008 (English abstract).
Chen et al. In vivo distribution and pharmacokinetics of dexamethasone sodium phosphate thermosensitive in situ gel following intratympanic injection. Sichuan Da Xue Xue Bao Yi Xue Ban 37(3):456-459. 2006 (English translation).
Chen et al. Preparation and characterization of dexamethasone acetate-loaded solid lipid nanoparticles. Chinese J Pharm 39(4):261-264. 2008 (English abstract).
Chen et al. Study on dexamethasone thermosensitive in situ gel for treating deafness. Chin Pharm J 41(9):685-688. 2006 (English abstract).
Ciprodex. product label. 2009.
Derin et al. The effects of L-carnitine on presbyacusis in the rat model. Clin Otolaryngol Allied Sci 29(3):238-241. 2004.
Endo et al. Novel strategy for treatment of inner ears using a biodegradable gel. Laryngoscope 115(11):2016-2020. 2005.
Feng et al. Effect of poloxamer 407 on the middle ear and inner ear after regional perfusion in guinea pigs. Zhonghua Er Bi Yan Hou Tou Jing Wai Ke Za Zhi 42(6):443-446. 2007 (English translation).
Feng et al. In vitro and in vivo biodegradation of sustained-release vehicle poloxamer 407 in situ gel. Lin Chung Er Bi Yan Hou Tou Jing Wai Ke Za Zhi 22(1):28-31. 2008 (English translation).
Feng et al. Zhonghua er Bi Yan Hou Tou Jing Wai Ke Za Zhi. Jun. 2007;42(6):443-6 (English Abstract).
Feng et al. Zhonghua Yi Xue Za Zhi. Aug. 28, 2007;87(32):2289-91 (English Translation).
Fernandez et al. Self-curing controlled release systems for steroids. Application of prednisolone-based polymeric systems to ear diseases. Biomaterials 26(16):3311-3318. 2005.
Friedman et al. GRM7 variants confer susceptibility to age-related hearing impairment. Hum Mol Genet 18(4):785-796. 2009.
Garduno-Anaya et al. Dexamethasone inner ear perfusion by intratympanic injection in unilateral Ménière's disease: a two-year prospective. placebo-controlled. double-blind. randomized trial. Otolaryngol Head Neck Surg 133(2):285-294. 2005.
GB0823378.5 combined search and examination report dated Feb. 27, 2009.
GB0823378.5 examination report dated Oct. 23, 2009.
GB0907065.7 combined search and examination report dated Nov. 16, 2009.
GB0912650.9 combined search and examination report dated Oct. 23, 2009.
Gubbels et al. Functional auditory hair cells produced in the mammalian cochlea by in utero gene transfer. Nature 455(7212):537-541. 2008.
Guyot et al. Intratympanic application of an antiviral agent for the treatment of Ménière's disease. ORL J Otorhinolaryngol Relat Spec 70(1):21-6; discussion 26-7. 2008.
Hargunani et al. Intratympanic injection of dexamethasone: time course of inner ear distribution and conversion to its active form. Otol Neurotol 27(4):564-569. 2006.
Harris et al. Prevention of noise-induced hearing loss with Src-PTK inhibitors. Hear Res 208(1-2):14-25. 2005.
Harris et al. Treatment of corticosteroid-responsive autoimmune inner ear disease with methotrexate: a randomized controlled trial. JAMA 290(14):1875-1883. 2003.
Hill et al. Cisplatin-induced ototoxicity: effect of intratympanic dexamethasone injections. Otol Neurotol 29:1005-1011. 2008.
Hoffer et al. Transtympanic management of tinnitus. Otolaryngol Clin North Am 36(2):353-358. 2003.
Hoshino et al. The non-steroidal anti-inflammatory drugs protect mouse cochlea against acoustic injury. Tohoku J Exp Med 216(1):53-59. 2008.
Inaoka et al. Local application of hepatocyte growth factor using gelatin hydrogels attenuates noise-induced hearing loss in guinea pigs. Acta Otolaryngol 129(4):453-457. 2009.
Jia et al. Intratympanic dexamethasone for refractory sudden deafness. Lin Chung Er Bi Yan Hou Tou Jing Wai Ke Za Zhi 22(7):309-311. 2008 (English translation).
Kazama et al. Lithium effectively complements vasopressin V2 receptor antagonist in the treatment of hyponatraemia of SIADH rats. Nephrol Dial Transplant 22(1):68-76. 2007.
Keithley et al. GDNF protects the cochlea against noise damage. Neuroreport 9(10):2183-2187. 1998.

(56) References Cited

OTHER PUBLICATIONS

Kim et al. Effects of tumor necrosis factor alpha antagonist. platelet activating factor antagonist. and nitric oxide synthase inhibitor on experimental otitis media with effusion. Ann Otol Rhinol Laryngol 115(8):617-623. 2006.
Kitahara et al. Up-regulation of cochlear aquaporin-3 mRNA expression after intra-endolymphatic sac application of dexamethasone. Neurol Res. 25(8):865-870. 2003.
Lamm et al. The effect of prednisolone and non-steroidal anti-inflammatory agents on the normal and noise-damaged guinea pig inner ear. Hear Res 115(1-2):149-161. 1998.
Lavreysen et al. Therapeutic potential of group III metabotropic glutamate receptors. Curr Med Chem 15(7):671-684. 2008.
Lee et al. Novel therapy for hearing loss: delivery of insulin-like growth factor 1 to the cochlea using gelatin hydrogel. Otol Neurotol 28(7):976-981. 2007.
Lee et al. Regional delivery of vancomycin using pluronic F-127 to inhibit methicillin resistant *Staphylococcus aureus* (MRSA) growth in chronic otitis media in vitro and in vivo. J Control Release 96(1):1-7. 2004.
Liu et al. Permeability of different Dexamethasone drugs through round window membrane. Zhonghua Er Bi Yan Hou Tou Jing Wai Ke Za Zhi 41(3):211-215. 2006 (English abstract).
Mcguinness et al. Exogenous BDNF rescues rat spiral ganglion neurons in vivo. Otol Neurotol 26(5):1064-1072. 2005.
Meltser et al. Estrogen receptor beta protects against acoustic trauma in mice. J Clin Invest 118(4):1563-1570. 2008.
Miceli et al. Molecular pharmacology and therapeutic potential of neuronal Kv7-modulating drugs. Curr Opin Pharmacol 8(1):65-74. 2008.
Mitsukawa et al. A selective metabotropic glutamate receptor 7 agonist: activation of receptor signaling via an allosteric site modulates stress parameters in vivo. PNAS USA 102(51):18712-18717. 2005.
Nakagawa et al. Local drug delivery to inner ear for treatment of hearing loss. Curr Drug Ther 3:143-147. 2008.
Nishimaki et al. Reduction of metabotropic glutamate receptor-mediated heterosynaptic inhibition of developing MNTB-LSO inhibitory synapses. Eur J Neurosci 26(2):323-330. 2007.
Nouvian et al. Degeneration of sensory outer hair cells following pharmacological blockade of cochlear KCNQ channels in the adult guinea pig. Eur J Neurosci 17(12):2553-2562. 2003.
Park et al. Effect of inhibitor of tumor necrosis factor-alpha and oxatomide on immune mediated otitis media. Laryngoscope 116(9):1642-1646. 2006.
Parnes et al. Corticosteroid pharmacokinetics in the inner ear fluids: an animal study followed by clinical application. Laryngoscope 109(7 Pt 2 Supplement No. 91):1-17. 1999.
Paulson et al. A novel controlled local drug delivery system for inner ear disease. Laryngoscope 118(4):706-711. 2008.
PCT/US2008/061330 International Search Report dated Jul. 31, 2008.
Peng et al. Clinical investigation of different routes of administration of dexamethasone on sudden deafness. Lin Chung Er Bi Yan Hou Tou Jing Wai Ke Za Zhi 22(10):442-445. 2008 (English translation).
Plontke et al. Rapid clearance of methylprednisolone after intratympanic application in humans. Comment on: Bird PA. Begg EJ. Zhang M. et al. Intratympanic versus intravenous delivery of methylprednisolone to cochlear perilymph. Otol Neurotol 2007; 28:1124-30. Otol Neurotol 29(5):732-733. 2008.
Pondugula et al. Glucocorticoid regulation of genes in the amiloride-sensitive sodium transport pathway by semicircular canal duct epithelium of neonatal rat. Physiol Genomics 24(2):114-123. 2006.
Pondugula et al. Glucocorticoids stimulate cation absorption by semicircular canal duct epithelium via epithelial sodium channel. Am J Physiol Renal Physiol 286(6):F1127-1135. 2004.
Psillas et al. Potential efficacy of early treatment of acute acoustic trauma with steroids and piracetam after gunshot noise. Eur Arch Otorhinolaryngol 265(12):1465-1469. 2008.

Puel. Chemical synaptic transmission in the cochlea. Prog Neurobiol 47(6):449-476. 1995.
Satoh et al. Tumor necrosis factor-alpha. An initiator. And etanercept. An inhibitor of.cochlear inflammation. Laryngoscope 112(9):1627-1634. 2002.
Schoepp et al. Pharmacological agents acting at subtypes of metabotropic glutamate receptors. Neuropharmacology 38(10):1431-1476. 1999.
Seidman et al. Anti-intercellular adhesion molecule-1 antibody's effect on noise damage. Laryngoscope 119(4):707-712. 2009.
She et al. A short term study on the efficacies of intratympanic prednisolone and dexamethasone injection for subjective tinnitus. Lin Chung Er Bi Yan Hou Tou Jing Wai Ke Za Zhi 22(19):871-873. 2008 (English translation).
Shepherd et al. Neurotrophins and electrical stimulation for protection and repair of spiral ganglion neurons following sensorineural hearing loss. Hear Res 242(1-2):100-109. 2008.
Shinohara et al. Neurotrophic factor intervention restores auditory function in deafened animals. PNAS USA 99(3):1657-1660. 2002.
Song et al. Bioorganic & Medicinal Chemistry Letters. 2003. Pergamon. 13:297-300.
Sun et al. In vitro permeability of round window membrane to transforming dexamethasone with delivery vehicles—a dosage estimation. Chin Med J (Engl) 120(24):2284-2289. 2007.
Synphora AB. website printout for JB004/A. 2009.
Tabuchi et al. Hearing impairment in TRPV4 knockout mice. Neurosci Lett 382(3):304-308. 2005.
Taguchi et al. Expressions of aquaporin-2. vasopressin type 2 receptor. transient receptor potential channel vanilloid (TRPV)1. and TRPV4 in the human endolymphatic sac. Laryngoscope 117(4):695-698. 2007.
Tahera et al. NF-kB mediated glucocorticoid response in the inner ear after acoustic trauma. J Neurosci Res 1;83(6):1066-1076. 2006.
Takeda et al. Aquaporins as potential drug targets for Meniere's disease and its related diseases. Handb Exp Pharmacol 190:171-184. 2009.
Takeda et al. Decompression effects of erythritol on endolymphatic hydrops. Auris Nasus Larynx 36(2):146-51. 2009.
Takeda et al. The effects of V2 antagonist (OPC-31260) on endolymphatic hydrops. Hear Res 182(1-2):9-18. 2003.
Takemura et al. Direct inner ear infusion of dexamethasone attenuates noise-induced trauma in guinea pig. Hear Res 196(1-2):58-68. 2004.
Takumida et al. Nitric oxide in the inner ear.Cur Opin Neurol 15(1):11-15. 2002.
Tang et al. COUP-TFI controls Notch regulation of hair cell and support cell differentiation. Development 133(18):3683-3693. 2006.
The Royal National Institute for Deaf People (RNID). advertisement insert in Nature Reviews Drug Discovery. May 2009.
Thorne et al. Potential role of purinergic signalling in cochlear pathology. Audiol Neurootol 7(3):180-184. 2002.
U.S. Appl. No. 12/486,697 Office Action dated Apr. 26, 2011.
U.S. Appl. No. 12/486,697 Office Action dated Dec. 29, 2011.
U.S. Appl. No. 12/506,091 Office Action dated Feb. 22, 2012.
Van Wijk et al. Local perfusion of the tumor necrosis factor alpha blocker infliximab to the inner ear improves autoimmune neurosensory hearing loss. Audiol Neurootol 11(6):357-365. 2006.
Wang et al. A novel dual inhibitor of calpains and lipid peroxidation (BN82270) rescues the cochlea from sound trauma. Neuropharmacology 52(6):1426-1437. 2007.
Wang et al. Over-expression of X-linked inhibitor of apoptosis protein slows presbycusis in C57BL/6J mice. Neurobiol Aging Aug. 26, 2008 [Epub ahead of print].
Watanabe et al. Inhibition of inducible nitric oxide synthase lowers the cochlear damage by lipopolysaccharide in guinea pigs. Free Radic Res 32(4):363-370. 2000.
Watanabe et al. Nitric oxide synthase inhibitor reduces the apoptotic change in the cisplatin-treated cochlea of guinea pigs. Anticancer Drugs 11(9):731-735. 2000.
Watanabe et al. Nitric oxide synthase inhibitor suppresses the ototoxic side effect of cisplatin in guinea pigs. Anticancer Drugs 11(5):401-406. 2000.

(56) References Cited

OTHER PUBLICATIONS

Yamamoto et al Inhibition of Notch/RBP-J signaling induces hair cell formation in neonate mouse cochleas. J Mol Med 84(1):37-45. 2006.

Yang et al. Intratympanic immunosuppressives for prevention of immune-mediated sensorineural hearing loss. Am J Otol 21(4):499-504. 2000.

Yildirim et al. Effect of intratympanic dexamethasone on noise-induced temporary threshold shift. Laryngoscope 115(7):1219-1222. 2005.

Zheng et al. Vanilloid receptors in hearing: altered cochlear sensitivity by vanilloids and expression of TRPV1 in the organ of corti. J Neurophysiol 90(1):444-455. 2003.

Zhou et al. Intratympanic administration of methylprednisolone reduces impact of experimental intensive impulse noise trauma on hearing. Acta Oto-Laryngologica 129:602-607. 2009.

\* cited by examiner

CONTROLLED RELEASE AURAL PRESSURE MODULATOR COMPOSITIONS AND METHODS FOR THE TREATMENT OF OTIC DISORDERS

CROSS-REFERENCE

This application is a Continuation application of U.S. Ser. No. 12/486,697, filed Jun. 17, 2009, which claims the benefit of U.S. Provisional Application No. 61/073,716 filed Jun. 18, 2008, U.S. Provisional Application No. 61/074,583 filed Jun. 20, 2008, U.S. Provisional Application No. 61/082,450 filed Jul. 21, 2008, U.S. Provisional Application No. 61/086,105 filed Aug. 4, 2008, U.S. Provisional Application No. 61/094,384 filed Sep. 4, 2008, U.S. Provisional Application No. 61/101,112 filed Sep. 29, 2008, and U.S. Provisional Application No. 61/140,033 filed Dec. 22, 2008, all of which are incorporated herein by reference in their entirety.

JOINT RESEARCH AGREEMENT

The claimed invention was made as a result of activities undertaken within the scope of a joint research agreement between Jay Benjamin Lichter, Benedikt K. Vollrath, Otonomy, Inc., and Avalon Ventures VIII GP, LLC that was in effect on or before the date the invention was made.

BACKGROUND OF THE INVENTION

Vertebrates have a pair of ears, placed symmetrically on opposite sides of the head. The ear serves as both the sense organ that detects sound and the organ that maintains balance and body position. The ear is generally divided into three portions: the outer ear, auris media (or middle ear) and the auris interna (or inner ear).

SUMMARY OF THE INVENTION

Described herein are compositions, formulations, manufacturing methods, therapeutic methods, uses, kits, and delivery devices for the controlled release or delivery of at least one aural pressure modulating agent to at least one structure or region of the ear.

In some embodiments, the aural pressure modulating agents target imbalance in aural pressure in the ear. In some embodiments, the aural pressure modulating agents target fluid homeostasis control in the inner ear, or auris interna. In other embodiments, the aural pressure modulating agents target fluid homeostasis control in the middle ear, or auris media. In some embodiments, the aural pressure modulators are vasopressin receptor modulators, prostaglandins or estrogen-related receptor modulators. In some embodiments, the aural pressure modulating agents are inhibitors of vasopressin receptor function, prostaglandin receptor or estrogen-related receptor function in the ear. In some embodiments, the aural pressure modulating agents are osmotic diuretic agents. In some embodiments, the controlled release formulations further comprise a rapid or immediate release component for delivering aural pressure modulating agents to the auris interna. All formulations comprise excipients that are auris-interna acceptable.

Also disclosed herein are methods and compositions for the treatment of otic diseases or conditions associated with an imbalance in aural pressure by administration of controlled release formulations comprising aural pressure modulating agents. In some embodiments, the otic disease or condition associated with an imbalance in aural pressure is a fluid homeostasis disorder. Also disclosed herein is the local delivery of controlled release aural pressure modulating compositions and formulations to suppress or ameliorate auditory and vestibular impairment as a result of an imbalance in aural pressure and/or imbalance in fluid homeostasis in the ear, such as Meniere's disease. In another aspect, the composition is administered so that the composition is in contact with the crista fenestrae cochleae, the round window or the tympanic cavity.

Disclosed herein are controlled release formulations for delivering an aural pressure modulating agent to the ear. In some embodiments, the target portion of the ear is the middle ear or auris media. In some embodiments, the target portion of the ear is the inner ear, or auris interna. In other embodiments, the target portion of the ear is both the auris media and the auris interna.

The auris formulations and therapeutic methods described herein have numerous advantages that overcome the previously-unrecognized limitations of formulations and therapeutic methods described in prior art.

Sterility

The environment of the inner ear is an isolated environment. The endolymph and the perilymph are static fluids and are not in contiguous contact with the circulatory system. The blood—labyrinth—barrier (BLB), which includes a blood-endolymph barrier and a blood-perilymph barrier, consists of tight junctions between specialized epithelial cells in the labyrinth spaces (i.e., the vestibular and cochlear spaces). The presence of the BLB limits delivery of active agents (e.g., aural pressure modulators) to the isolated microenvironment of the inner ear. Auris hair cells are bathed in endolymphatic or perilymphatic fluids and cochlear recycling of potassium ions is important for hair cell function. When the inner ear is infected, there is an influx of leukocytes and/or immunoglobins (e.g. in response to a microbial infection) into the endolymph and/or the perilymph and the delicate ionic composition of inner ear fluids is upset by the influx of leukocytes and/or immunoglobins. In certain instances, a change in the ionic composition of inner ear fluids results in hearing loss, loss of balance and/or ossification of auditory structures. In certain instances, even trace amounts of pyrogens and/or microbes can trigger infections and related physiological changes in the isolated microenvironment of the inner ear.

Due to the susceptibilty of the inner ear to infections, auris formulations require a level of sterility (e.g., low bioburden) that has not been recognized hitherto in prior art. Provided herein are auris formulations that are manufactured with low bioburden or sterilized with stringent sterilty requirements and are suitable for administration to the middle and/or inner ear. In some embodiments, the auris compatible compositions described herein are substantially free of pyrogens and/or microbes.

Compatibility with Inner Ear Environment

Described herein are otic formulations with an ionic balance that is compatible with the perilymph and/or the endolymph and does not cause any change in cochlear potential. In specific embodiments, osmolarity/osmolality of the present formulations is adjusted, for example, by the use of appropriate salt concentrations (e.g., concentration of sodium salts) or the use of tonicity agents which renders the formulations endolymph-compatible and/or perilymph-compatible (i.e. isotonic with the endolymph and/or perilymph). In some instances, the endolymph-compatible and/or perilymph-compatible formulations described herein cause minimal disturbance to the environment of the inner ear and cause minimum discomfort (e.g, vertigo) to a mammal (e.g., a human) upon administration. Further, the formulations comprise polymers that are biodegradable and/or dispersable, and/or otherwise non-toxic to the inner ear environment. In some embodiments, the formulations described herein are free of preservatives and cause minimal disturbance (e.g., change in pH or osmolarity, irritation) in auditory structures. In some embodiments, the formulations described herein comprise antioxidants that are non-irritating and/or non-toxic to otic structures.

Dosing Frequency

The current standard of care for auris formulations requires multiple administrations of drops or injections (e.g. intratympanic injections) over several days (e.g., up to two weeks), including schedules of receiving multiple injections per day. In some embodiments, auris formulations described herein are controlled release formulations, and are administered at reduced dosing frequency compared to the current standard of care. In certain instances, when an auris formulation is administered via intratympanic injection, a reduced frequency of administration alleviates discomfort caused by multiple intratympanic injections in individuals undergoing treatment for a middle and/or inner ear disease, disorder or condition. In certain instances, a reduced frequency of administration of intratympanic injections reduces the risk of permanent damage (e.g., perforation) to the ear drum. The formulations described herein provide a constant, sustained, extended, delayed or pulsatile rate of release of an active agent into the inner ear environment and thus avoid any variability in drug exposure in treatment of otic disorders.

Therapeutic Index

Auris formulations described herein are administered into the ear canal, or in the vestibule of the ear. Access to, for example, the vestibular and cochlear apparatus will occur through the auris media including the round window membrane, the oval window/stapes footplate, the annular ligament and through the otic capsule/temporal bone. Otic administration of the formulations described herein avoids toxicity associated with systemic administration (e.g., hepatotoxicity, cardiotoxicity, gastrointestinal side effects, renal toxicity) of the active agents. In some instances, localized administration in the ear allows an active agent to reach a target organ (e.g., inner ear) in the absence of systemic accumulation of the active agent. In some instances, local administration to the ear provides a higher therapeutic index for an active agent that would otherwise have dose-limiting systemic toxicity.

Prevention of Drainage into Eustachian Tube

In some instances, a disadvantage of liquid formulations is their propensity to drip into the eustachian tube and cause rapid clearance of the formulation from the inner ear. Provided herein, in certain embodiments, are auris formulations comprising polymers that gel at body temperature and remain in contact with the target auditory surfaces (e.g., the round window) for extended periods of time. In some embodiments, the formulations further comprise mucoadhesives that allow the formulations to adhere to otic mucosal surfaces. In some instances, the auris formulations described herein avoid attenuation of therapeutic benefit due to drainage or leakage of active agents via the eustachian tube.

Description of Certain Embodiments

Described herein are controlled release compositions and devices for treating otic disorders comprising a therapeutically-effective amount of an aural pressure modulating agent, a controlled release auris-acceptable excipient and an auris-acceptable vehicle. In one aspect, the controlled release auris-acceptable excipient is chosen from an auris-acceptable polymer, an auris-acceptable viscosity enhancing agent, an auris-acceptable gel, an auris-acceptable paint, an auris-acceptable foam, an auris-acceptable microsphere or microparticle, an auris-acceptable hydrogel, an auris-acceptable in situ forming spongy material, an auris-acceptable actinic radiation curable gel, an auris-acceptable liposome, an auris-acceptable nanocapsule or nanosphere, an auris-acceptable thermoreversible gel or combinations thereof. In further embodiments, the auris-acceptable viscosity enhancing agent is a cellulose, a cellulose ether, alginate, polyvinylpyrrolidone, a gum, a cellulosic polymer or combinations thereof. In yet another embodiment, the auris-acceptable viscosity enhancing agent is present in an amount sufficient to provide a viscosity of between about 1000 to about 1,000,000 centipoise. In still another aspect, the auris-acceptable viscosity enhancing agent is present in an amount sufficient to provide a viscosity of between about 50,000 to about 1,000,000 centipoise. In some embodiments, the aural pressure modulating formulations or compositions are optimal for osmolality or osmolarity of the target auris structure to ensure homeostasis is maintained.

In some embodiments, the compositions are formulated for pH, and a practical osmolality or osmolarity to ensure that homeostasis of the target auris structure is maintained. A perilymph-suitable osmolarity/osmolality is a practical/deliverable osmolarity/osmolality that maintains the homeostasis of the target auris structure during administration of the pharmaceutical formulations described herein.

For example, the osmolarity of the perilymph is between about 270-300 mOsm/L, and the compositions described herein are optionally formulated to provide a practical osmolarity of about 150 to about 1000 mOsm/L. In certain embodiments, the formulations described herein provide a practical and/or deliverable osmolarity within about 150 to about 500 mOsm/L at the target site of action (e.g., the inner ear and/or the perilymph and/or the endolymph). In certain embodiments, the formulations described herein provide a practical osmolarity within about 200 to about 400 mOsm/L at the target site of action (e.g., the inner ear and/or the perilymph and/or the endolymph). In certain embodiments, the formulations described herein provide a practical osmolarity within about 250 to about 320 mOsm/L at the target site of action (e.g., the inner ear and/or the perilymph and/or the endolymph). In certain embodiments, the formulations described herein provide a perilymph-suitable osmolarity within about 150 to about 500 mOsm/L, about 200 to about 400 mOsm/L or about 250 to about 320 mOsm/L at the target site of action (e.g., the inner ear and/or the perilymph and/or the endolymph). In certain embodiments, the formulations described herein provide a perilymph-suitable osmolality within about 150 to about 500 mOsm/kg, about 200 to about 400 mOsm/kg or about 250 to about 320 mOsm/kg at the target site of action (e.g., the inner ear and/or the perilymph and/or the endolymph). Similarly, the pH of the perilymph is about 7.2-7.4, and the pH of the present formulations is formulated (e.g., with the use of buffers) to provide a perilymph-suitable pH of about 5.5 to about 9.0, about 6.0 to about 8.0 or about 7.0 to about 7.6. In certain embodiments, the pH of the formulations is within about 6.0 to about 7.6. In certain instances, the pH of the endolymph is about 7.2-7.9, and the pH of the present formulations is formulated (e.g., with the use of buffers) to be within about 5.5 to about 9.0, within about 6.5 to about 8.0 or within about 7.0 to about 7.6.

In some aspects, the controlled-release auris-acceptable excipient is biodegradable. In some aspects the controlled release auris-acceptable excipient is bioeliminated (e.g., degraded and/or eliminated through urine, feces or other routes of elimination). In another aspect, the controlled release composition further comprises an auris-acceptable mucoadhesive, an auris-acceptable penetration enhancer or an auris-acceptable bioadhesive.

In one aspect, the controlled release aural pressure modulating agent composition is delivered using a drug delivery device, which is a needle and syringe, a pump, a microinjection device or combinations thereof. In some embodiments, the aural pressure modulator of the controlled release composition has limited or no systemic release, is toxic when administered systemically, has poor pK characteristics or combinations thereof. In some aspects, the aural pressure modulator is a small molecule agent. In other aspects, the aural pressure modulator is an antibody. In some embodiments, the aural pressure modulator is a vasopressin receptor modulator, a prostaglandin receptor modulator or an estrogen-related receptor modulator. In additional aspects, the vasopressin receptor modulator specifically acts on vasopressin receptor 2 (VP2).

Also disclosed herein is a method for treating an otic disorder comprising administering at least once every 3, 4, 5, 6, 7, 8, 9, 10, 11, 12, 13, 14, or 15 days, at least once a week, once every two weeks, once every three weeks, once every four weeks, once every five weeks, or once every six weeks; or once a month, once every two months, once every three months, once every four months, once every five months, once every six months, once every seven months, once every eight months, once every nine months, once every ten months, once every eleven months, or once every twelve months with the compositions and formulations disclosed herein. In particular embodiments, the controlled release formulations described herein provide a sustained dose of aural pressure modulating agent to the inner ear between subsequent doses of the controlled release formulation. That is, taking one example only, if new doses of the aural pressure modulating agent controlled release formulation are administered via intratympanic injection to the round window membrane every 10 days, then the controlled release formulation provides an effective dose of aural pressure modulating agent to the inner ear (e.g., across the round window membrane) during that 10-day period.

In one aspect, the composition is administered so that the composition is in contact with the crista fenestrae cochleae, the round window membrane or the tympanic cavity. In one aspect the composition is administered by intratympanic injection.

Provided herein is a pharmaceutical composition or device comprising an amount of an aural pressure modulating agent that is therapeutically effective for treating an otic disease or condition associated with an imbalance in aural pressure, the pharmaceutical composition or device comprising substantially low degradation products of the auris pressure modulating agent, the pharmaceutical composition or device further comprising two or more characteristics selected from:
  (i) between about 0.1% to about 10% by weight of the aural pressure modulating agent, or pharmaceutically acceptable prodrug or salt thereof;
  (ii) between about 14% to about 21% by weight of a polyoxyethylene-polyoxypropylene triblock copolymer of general formula E106 P70 E106;
  (iii) sterile water, q.s., buffered to provide a pH between about 5.5 and about 8.0;
  (iv) multiparticulate aural pressure modulating agent;
  (v) a gelation temperature between about 19° C. to about 42° C.;
  (vi) less than about 50 colony forming units (cfu) of microbiological agents per gram of formulation, and
  (vii) less than about 5 endotoxin units (EU) per kg of body weight of a subject.

In some embodiments, a pharmaceutical composition or device described herein comprises:
  (i) between about 0.1% to about 10% by weight of the aural pressure modulating agent, or pharmaceutically acceptable prodrug or salt thereof;
  (ii) between about 14% to about 21% by weight of a polyoxyethylene-polyoxypropylene triblock copolymer of general formula E106 P70 E106; and
  (iii) multiparticulate aural pressure modulating agent.

In some embodiments, a pharmaceutical composition or device described herein comprises:
  (i) between about 0.1% to about 10% by weight of the aural pressure modulating agent, or pharmaceutically acceptable prodrug or salt thereof;
  (ii) between about 14% to about 21% by weight of a polyoxyethylene-polyoxypropylene triblock copolymer of general formula E106 P70 E106;
  (iii) multiparticulate aural pressure modulating agent; and
  (iv) a gelation temperature between about 19° C. to about 42° C.

In some embodiments a pharmaceutical composition or device described above provides a practical osmolarity between about 150 and 500 mOsm/L. In some embodiments a pharmaceutical composition or device described above provides a practical osmolarity between about 200 and 400 mOsm/L. In some embodiments a pharmaceutical composition or device described above provides a practical osmolarity between about 250 and 320 mOsm/L.

In some embodiments, the aural pressure modulating agent is released from the pharmaceutical composition or device described above for a period of at least 3 days. In some embodiments, the aural pressure modulating agent is released from the pharmaceutical composition or device described above for a period of at least 5 days. In some embodiments, the aural pressure modulating agent is released from the pharmaceutical composition or device described above for a period of at least 10 days. In some embodiments, the aural pressure modulating agent is released from the pharmaceutical composition or device described above for a period of at least 14 days. In some embodiments, the aural pressure modulating agent is released from the pharmaceutical composition or device described above for a period of at least one month.

In some embodiments, a pharmaceutical composition or device described above comprises aural pressure modulating agent as a neutral compound, a free acid, a free base, a salt or a prodrug. In some embodiments, a pharmaceutical composition or device described above comprises aural pressure modulating agent as a neutral compound, a free acid, a free base, a salt or a prodrug, or a combination thereof.

In some embodiments, a pharmaceutical composition or device described above is an auris-acceptable thermoreversible gel. In some embodiments of the pharmaceutical composition or device, the polyoxyethylene-polyoxypropylene triblock copolymer is bioeliminated.

In some embodiments the pharmaceutical composition or device further comprises a penetration enhancer. In some embodiments, the pharmaceutical composition or device further comprises a dye.

In some embodiments of the pharmaceutical composition or device described above, the aural pressure modulating agent inhibits vasopressin receptor function, prostaglandin receptor function or estrogen-related receptor beta function, or combinations thereof.

In some embodiments, the pharmaceutical composition or device further comprises the aural pressure modulating agent, or pharmaceutically acceptable salt thereof, prodrug or combination thereof as an immediate release agent.

In some embodiments of the pharmaceutical composition or device the aural pressure modulating agent comprises multiparticulates. In some embodiments of the pharmaceutical composition or device the aural pressure modulating agent is essentially in the form of micronized particles. In some embodiments of the pharmaceutical composition or device, the aural pressure modulating agent is in the form of micro-aural pressure modulating agent powder.

In some embodiments, a pharmaceutical composition or device described above comprises aural pressure modulating agent as multiparticulates. In some embodiments, a pharmaceutical composition or device described above comprises aural pressure modulating agent in the form of micronized particles. In some embodiments, a pharmaceutical composition or device described above comprises aural pressure modulating agent as micronized powder.

In some embodiments, a pharmaceutical composition or device described above comprises about 10% of a polyoxyethylene-polyoxypropylene triblock copolymer of general formula E106 P70 E106 by weight of the composition. In some embodiments, a pharmaceutical composition or device described above comprises about 15% of a polyoxyethylene-polyoxypropylene triblock copolymer of general formula E106 P70 E106 by weight of the composition. In some embodiments, a pharmaceutical composition or device described above comprises about 20% of a polyoxyethylene-polyoxypropylene triblock copolymer of general formula E106 P70 E106 by weight of the composition. In some embodiments, a pharmaceutical composition or device described above comprises about 25% of a polyoxyethylene-polyoxypropylene triblock copolymer of general formula E106 P70 E106 by weight of the composition.

In some embodiments, a pharmaceutical composition or device described above comprises about 0.01% of an aural pressure modulating agent, or pharmaceutically acceptable prodrug or salt thereof, by weight of the composition. In some embodiments, a pharmaceutical composition or device described above comprises about 0.05% of an aural pressure modulating agent, or pharmaceutically acceptable prodrug or salt thereof, by weight of the composition. In some embodiments, a pharmaceutical composition or device described above comprises about 0.1% of an aural pressure modulating agent, or pharmaceutically acceptable prodrug or salt thereof, by weight of the composition. In some embodiments, a pharmaceutical composition or device described above comprises about 1% of an aural pressure modulating agent, or pharmaceutically acceptable prodrug or salt thereof, by weight of the composition. In some embodiments, a pharmaceutical composition or device described above comprises about 2.5% of an aural pressure modulating agent, or pharmaceutically acceptable prodrug or salt thereof, by weight of the composition. In some embodiments, a pharmaceutical composition or device described above comprises about 5% of an aural pressure modulating agent, or pharmaceutically acceptable prodrug or salt thereof, by weight of the composition. In some embodiments, a pharmaceutical composition or device described above comprises about 10% of an aural pressure modulating agent, or pharmaceutically acceptable prodrug or salt thereof, by weight of the composition. In some embodiments, a pharmaceutical composition or device described above comprises about 20% of an aural pressure modulating agent, or pharmaceutically acceptable prodrug or salt thereof, by weight of the composition. In some embodiments, a pharmaceutical composition or device described above comprises about 30% of an aural pressure modulating agent, or pharmaceutically acceptable prodrug or salt thereof, by weight of the composition. In some embodiments, a pharmaceutical composition or device described above comprises about 40% of an aural pressure modulating agent, or pharmaceutically acceptable prodrug or salt thereof, by weight of the composition. In some embodiments, a pharmaceutical composition or device described above comprises about 50% of an aural pressure modulating agent, or pharmaceutically acceptable prodrug or salt thereof, by weight of the composition.

In some embodiments, a pharmaceutical composition or device described above has a pH between about 5.5 to about 8.0. In some embodiments, a pharmaceutical composition or device described above has a pH between about 6.0 to about 8.0. In some embodiments, a pharmaceutical composition or device described above has a pH between about 6.0 to about 7.6. In some embodiments, a pharmaceutical composition or device described above has a pH between about 7.0 to about 7.6.

In some embodiments, a pharmaceutical composition or device described above contains less than 100 colony forming units (cfu) of microbiological agents per gram of formulation. In some embodiments, a pharmaceutical composition or device described above contains less than 50 colony forming units (cfu) of microbiological agents per gram of formulation. In some embodiments, a pharmaceutical composition or device described above contains less than 10 colony forming units (cfu) of microbiological agents per gram of formulation.

In some embodiments, a pharmaceutical composition or device described above contains less than 5 endotoxin units (EU) per kg of body weight of a subject. In some embodiments, a pharmaceutical composition or device described above contains less than 4 endotoxin units (EU) per kg of body weight of a subject.

In some embodiments a pharmaceutical composition or device described above provides a gelation temperature between about between about 19° C. to about 42° C. In some embodiments a pharmaceutical composition or device described above provides a gelation temperature between about between about 19° C. to about 37° C. In some embodiments a pharmaceutical composition or device described above provides a gelation temperature between about between about 19° C. to about 30° C.

In some embodiments, the pharmaceutical composition or device is an auris-acceptable thermoreversible gel. In some embodiments, the polyoxyethylene-polyoxypropylene triblock copolymer is biodegradable and/or bioeliminated (e.g., the copolymer is eliminated from the body by a biodegradation process, e.g., elimination in the urine, the feces or the like). In some embodiments, a pharmaceutical composition or device described herein further comprises a mucoadhesive. In some embodiments, a pharmaceutical composition or device described herein further comprises a penetration enhancer. In some embodiments, a pharmaceutical composition or device described herein further comprises a thickening agent. In some embodiments, a pharmaceutical composition or device described herein further comprises a dye.

In some embodiments, a pharmaceutical composition or device described herein further comprises a drug delivery device selected from a needle and syringe, a pump, a microinjection device, a wick, an in situ forming spongy material or combinations thereof.

In some embodiments, a pharmaceutical composition or device described herein is a pharmaceutical composition or device wherein the aural pressure modulating agent, or pharmaceutically acceptable salt thereof, has limited or no systemic release, systemic toxicity, poor PK characteristics, or combinations thereof. In some embodiments of the pharmaceutical compositions or devices described herein, the aural pressure modulating agent is in the form of a neutral molecule, free base, a free acid, a salt, a prodrug, or a combination thereof. In some embodiments of the pharmaceutical compositions or devices described herein, the aural pressure modulating agent is administered in the form of a phosphate or ester prodrug. In some embodiments pharmaceutical compositions or devices described herein comprise one or more aural pressure modulating agent, or pharmaceutically acceptable salt thereof, prodrug or combination thereof as an immediate release agent.

In some embodiments, pharmaceutical compositions or devices described herein further comprise an additional therapeutic agent. In some embodiments, the additional therapeutic agent is a diuretic, an anti-emetic agent, an anti-vertigo agent, a local acting anesthetic agent, an anti-anxiety agent, a corticosteroid, an anti-histamine, or combinations thereof. In some embodiments, the additional therapeutic agent is an otoprotectant, a Na/K ATPase modulator, a KCNQ channel modulator, or combinations thereof.

In some embodiments, pharmaceutical compositions or devices described herein are pharmaceutical compositions or devices wherein the pH of the pharmaceutical composition or device is between about 6.0 to about 7.6.

In some embodiments of the pharmaceutical compositions or devices described herein, the ratio of a polyoxyethylene-polyoxypropylene triblock copolymer of general formula E106 P70 E106 to a thickening agent is from about 40:1 to about 5:1. In some embodiments, the thickening agent is carboxymethyl cellulose, hydroxypropyl cellulose or hydroxypropyl methylcellulose.

In some embodiments, the otic disease or condition is Meniere's disease, sudden sensorineural hearing loss, noise induced hearing loss, age related hearing loss, auto immune ear disease or tinnitus.

Also provided herein is a method of treating an otic disease or condition associated with an imbalance in aural pressure comprising administering to an individual in need thereof an intratympanic composition or device comprising a therapeutically effective amount of aural pressure modulating agent, the composition or device comprising substantially low degradation products of aural pressure modulating agent, the composition or device further comprising two or more characteristics selected from:
  (i) between about 0.1% to about 10% by weight of the aural pressure modulating agent, or pharmaceutically acceptable prodrug or salt thereof;
  (ii) between about 14% to about 21% by weight of a polyoxyethylene-polyoxypropylene triblock copolymer of general formula E106 P70 E106;
  (iii) sterile water, q.s., buffered to provide a pH between about 5.5 and about 8.0;
  (iv) multiparticulate aural pressure modulating agent;
  (v) a gelation temperature between about 19° C. to about 42° C.;
  (vi) less than about 50 colony forming units (cfu) of microbiological agents per gram of formulation, and
  (vii) less than about 5 endotoxin units (EU) per kg of body weight of a subject.

In some embodiments of the methods described herein, the aural pressure modulating agent is released from the composition or device for a period of at least 3 days. In some embodiments of the methods described herein, the aural pressure modulating agent is released from the composition or device for a period of at least 5 days. In some embodiments of the methods described herein, the aural pressure modulating agent is released from the composition or device for a period of at least 10 days. In some embodiments of the method described above, the aural pressure modulating agent is essentially in the form of micronized particles.

In some embodiments of the methods described herein, the composition is administered across the round window. In some embodiments of the methods described herein, the otic disease or condition is Meniere's disease, sudden sensorineural hearing loss, noise induced hearing loss, age related hearing loss, auto immune ear disease or tinnitus.

DETAILED DESCRIPTION OF THE INVENTION

Figure 1:
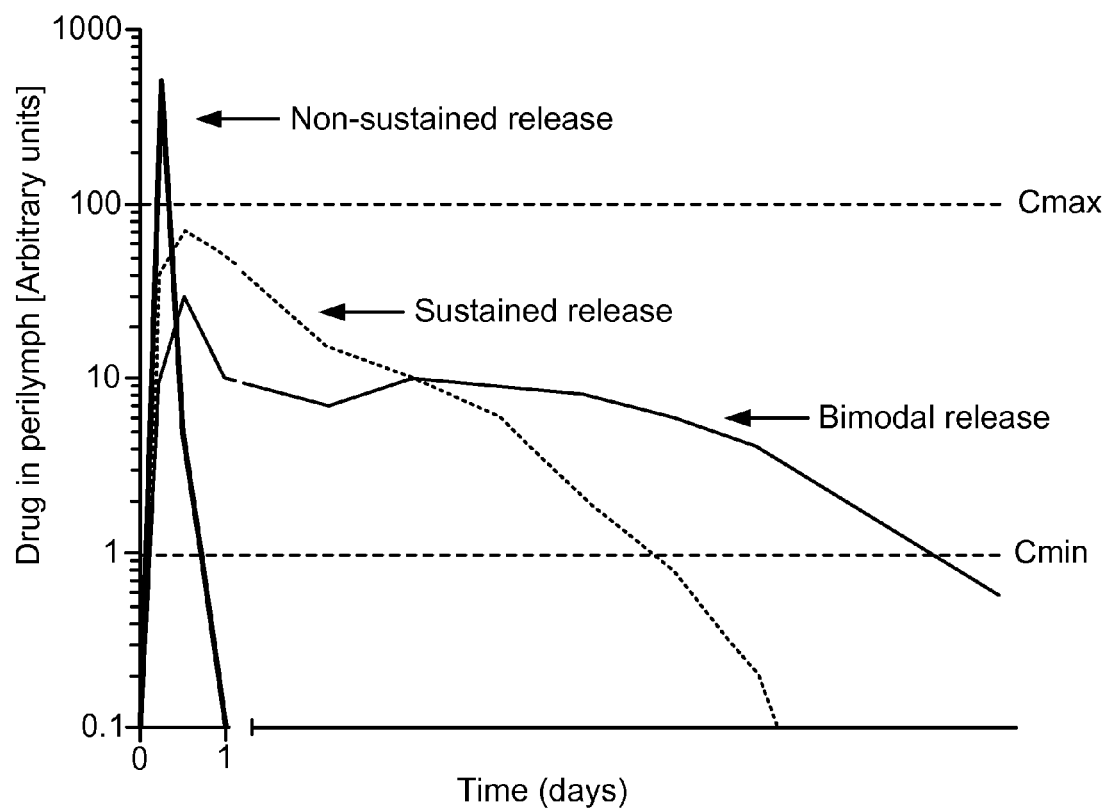
FIG. 1. illustrates a comparison of non-sustained release and sustained release formulations.
Figure 2:
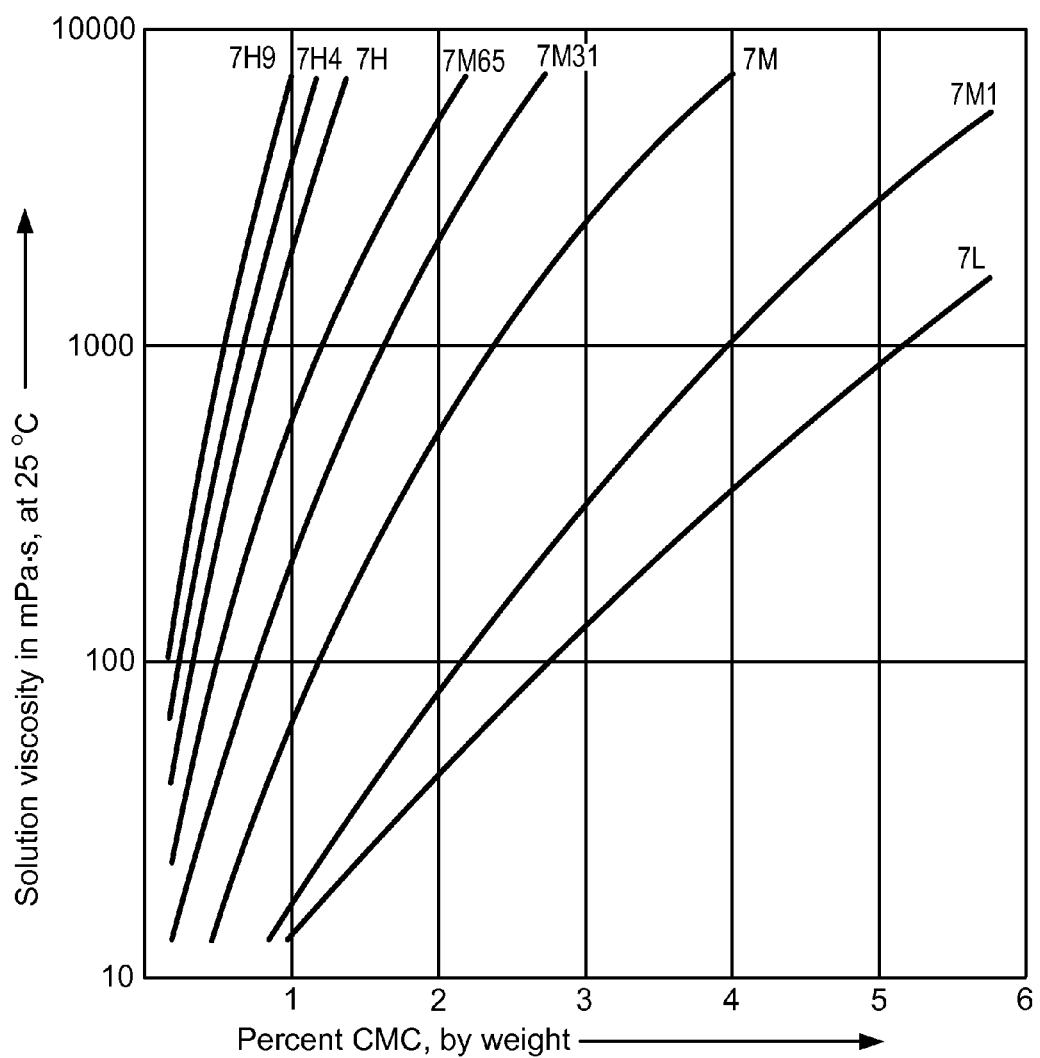
FIG. 2 illustrates the effect of concentration on the viscosity of aqueous solutions of Blanose refined CMC.
Figure 3:
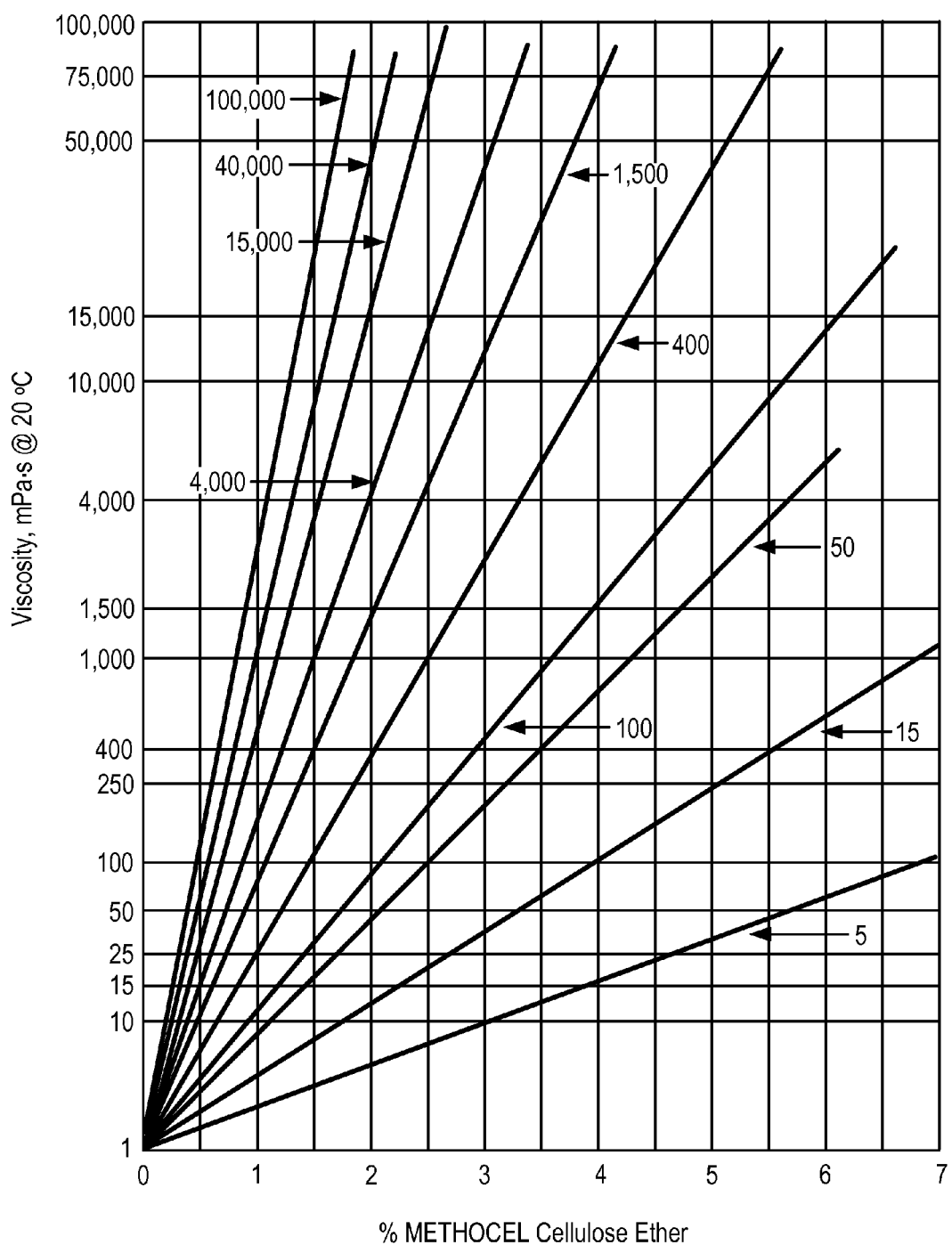
FIG. 3 illustrates the effect of concentration on the viscosity of aqueous solutions of Methocel.

Provided herein are controlled release aural pressure modulating compositions and formulations to treat otic diseases or conditions associated with an imbalance in aural pressure (e.g., fluid homeostasis disorders of the ear), including Meniere's Disease, endolymphatic hydrops, progressive hearing loss, dizziness, vertigo, tinnitus and similar conditions. In some instances, an imbalance in aural pressure in the ear is a result of an imbalance in fluid homeostasis control in the inner ear, or auris interna. In some instances, an imbalance in aural pressure is a result of an imbalance in fluid homeostasis control in the middle ear, or auris media. In some instances, an imbalance in aural pressure in the ear causes a feeling of fullness in the ear. In some instances, an imbalance in aural pressure in the ear causes nausea and/or vertigo and/or tinnitus.

Systemic routes via oral, intravenous or intramuscular routes are currently used to deliver aural pressure modulating therapeutic agents. Systemic drug administration may create a potential inequality in drug concentration with higher circulating levels in the serum, and lower levels in the target auris interna organ structures. As a result, fairly large amounts of drug are required to overcome this inequality in order to deliver sufficient, therapeutically effective quantities to the inner ear. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic. Systemic administration of aural pressure modulators may result in the unwanted modulation of other organ systems where water homeostasis is vital, such as the cardiovascular or renal system. For example, administration of the vasopressin antagonist conivaptan is indicated in patients with hypervolemic hyponatremia arising from an underlying cause, such as congestive heart failure. Systemic administration of a vasopressin antagonist to a patient suffering only from fluid homeostasis disorders of the ear could result in hypovolemia, hypernatremia or hypotension in the patient, due to systemic effects of vasopressin antagonists on the renal system.

To overcome the toxic and attendant side effects of systemic delivery, disclosed herein are methods and compositions for local delivery of aural pressure modulators to auris interna structures. Access to, for example, the vestibular and cochlear apparatus occurs through the auris media, including the oval window/stapes footplate, the annular ligament and through the otic capsule/temporal bone, and the round window membrane of the auris interna.

In addition, localized treatment of the auris interna also affords the use of previously undesired therapeutic agents, including agents with poor pK profiles, poor uptake, low systemic release and/or toxicity issues. Because of the localized targeting of the aural pressure modulating formulations and compositions, as well as the biological blood barrier present in the auris interna, the risk of adverse effects will be reduced as a result of treatment with previously characterized toxic or ineffective aural pressure modulators. Accordingly, also contemplated within the scope of the embodiments herein is the use of aural pressure modulating agents in the treatment of fluid homeostasis otic disorders that have been previously rejected by practitioners because of adverse effects or ineffectiveness of the aural pressure modulators (e.g., vasopressin receptor modulators).

Also included within the embodiments disclosed herein is the use of additional auris interna agents in combination with the aural pressure modulating formulations and compositions disclosed herein. When used, such agents assist in the treatment of hearing or equilibrium loss or dysfunction as a result of a fluid homeostasis disorder, including vertigo, tinnitus, hearing loss, balance disorders or combinations thereof. Accordingly, agents that ameliorate or reduce the effects of vertigo, tinnitus, hearing loss, balance disorders, or combinations thereof are also contemplated to be used in combination with the aural pressure modulators, including steroids, anti-emetic agents, corticosteroids, local acting anesthetic agents, chemotherapeutic agents, including cytoxan, azathiaprine or methotrexate; and combinations thereof.

In addition, the aural pressure modulating pharmaceutical compositions or formulations included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the auris interna. Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, aural pressure modulating pharmaceutical compositions or formulations disclosed herein are optionally targeted to distinct regions of the auris interna, including but not limited to the vestibular bony and membranous labyrinths, cochlear bony and membranous labyrinths and other anatomical or physiological structures located within the auris interna.

In some instances, systemic drug administration creates a potential inequality in drug concentration with higher circulating levels in the serum, and lower levels in the target auris media and auris interna organ structures. As a result, fairly large amounts of drug are required to overcome this inequality in order to deliver sufficient, therapeutically effective quantities to the inner ear. In addition, systemic drug administration may increase the likelihood of systemic toxicities and adverse side effects as a result of the high serum amounts required to effectuate sufficient local delivery to the target site. Systemic toxicities may also occur as a result of liver breakdown and processing of the therapeutic agents, forming toxic metabolites that effectively erase any benefit attained from the administered therapeutic.

To overcome the toxic and attendant side effects of systemic delivery, disclosed herein are methods and compositions and devices for local delivery of therapeutic agents to targeted auris structures. Access to, for example, the vestibular and cochlear apparatus will occur through the auris media including round window membrane, the oval window/stapes footplate, the annular ligament and through the otic capsule/temporal bone.

Intratympanic injection of therapeutic agents is the technique of injecting a therapeutic agent behind the tympanic membrane into the auris media and/or auris interna. Despite early success with this technique (Schuknecht, Laryngoscope (1956) 66, 859-870) some challenges do remain. For example, access to the round window membrane, the site of drug absorption into the auris interna, can be challenging.

However, intra-tympanic injections create several unrecognized problems not addressed by currently available treatment regimens, such as changing the osmolarity and pH of the perilymph and endolymph, and introducing pathogens and endotoxins that directly or indirectly damage inner ear structures. One of the reasons the art may not have recognized these problems is that there are no approved intra-tympanic compositions: the inner ear provides sui generis formulation challenges. Thus, compositions developed for other parts of the body have little to no relevance for an intra-tympanic composition.

There is no guidance in the prior art regarding requirements (e.g., level of sterility, pH, osmolarity) for otic formulations that are suitable for administration to humans. There is wide anatomical disparity between the ears of animals across species. A consequence of the inter-species differences in auditory structures is that animal models of inner ear disease are often unreliable as a tool for testing therapeutics that are being developed for clinical approval.

Provided herein are otic formulations that meet stringent criteria for pH, osmolarity, ionic balance, sterility, endotoxin and/or pyrogen levels. The auris compositions described herein are compatible with the microenvironment of the inner ear (e.g., the perilymph) and are suitable for administration to humans. In some embodiments, the formulations described herein comprise dyes and aid visualization of the administered compositions obviating the need for invasive procedures (e.g., removal of perilymph) during preclinical and/or clinical development of intratympanic therapeutics.

Provided herein are controlled release aural pressure modulating agent formulations and compositions to locally treat targeted auris structures, thereby avoiding side effects as a result of systemic administration of the aural pressure modulating agent formulations and compositions. The locally applied aural pressure modulating agent formulations and compositions and devices are compatible with the targeted auris structures, and administered either directly to the desired targeted auris structure, e.g. the cochlear region, the tympanic cavity or the external ear, or administered to a structure in direct communication with areas of the auris interna, including but not limited to the round window membrane, the crista fenestrae cochleae or the oval window membrane. By specifically targeting an auris structure, adverse side effects as a result of systemic treatment are avoided. Moreover, clinical studies have shown the benefit of having long term exposure of drug to the perilymph of the cochlea, for example with improved clinical efficacy of sudden hearing loss when the therapeutic agent is given on multiple occasions. Thus, by providing a controlled release aural pressure modulating agent formulation or composition to treat otic disorders, a constant, variable and/or extended source of aural pressure modulating agent is provided to the individual or patient suffering from an otic disorder, reducing or eliminating variabilities in treatment. Accordingly, one embodiment disclosed herein is to provide a composition that enables at least one aural pressure modulating agent to be released in therapeutically effective doses either at variable or constant rates such as to ensure a continuous release of the at least one agent. In some embodiments, the aural pressure modulating agents disclosed herein are administered as an immediate release formulation or composition. In other embodiments, the aural pressure modulating agents are administered as a sustained release formulation, released either continuously, variably or in a pulsatile manner, or variants thereof. In still other embodiments, aural pressure modulating agent formulation is administered as both an immediate release and sustained release formulation, released either continuously, variably or in a pulsatile manner, or variants thereof. The release is optionally dependent on environmental or physiological conditions, for example, the external ionic environment (see, e.g. Oros® release system, Johnson & Johnson).

In addition, localized treatment of the targeted auris structure also affords the use of previously undesired therapeutic agents, including agents with poor pK profiles, poor uptake, low systemic release and/or toxicity issues. Because of the localized targeting of the aural pressure modulating agent formulations and compositions and devices, as well as the biological blood barrier present in the auris interna, the risk of adverse effects will be reduced as a result of treatment with previously characterized toxic or ineffective aural pressure modulating agents. Accordingly, also contemplated within the scope of the embodiments herein is the use of aural pressure modulating agents in the treatment of homeostasis-related otic disorders that have been previously rejected by practitioners because of adverse effects or ineffectiveness of the aural pressure modulating agent.

Also included within the embodiments disclosed herein is the use of additional auris-compatible agents in combination with the aural pressure modulating agent formulations and compositions and devices disclosed herein. When used, such agents assist in the treatment of hearing or equilibrium loss or dysfunction as a result of an autoimmune disorder, including vertigo, tinnitus, hearing loss, balance disorders, infections, or combinations thereof. Accordingly, agents that ameliorate or reduce the effects of vertigo, tinnitus, hearing loss, balance disorders, infections, inflammatory response or combinations thereof are also contemplated to be used in combination with the aural pressure modulating agent(s), including a diuretic, an anti-emetic agent, an anti-vertigo agent, a local acting anesthetic agent, an anti-anxiety agent, a corticosteroid, an anti-histamine an otoprotectant, a Na/K ATPase modulator, a KCNQ channel modulator, or combinations thereof.

In addition, the auris-acceptable controlled-release aural pressure modulating agent formulations and treatments described herein are provided to the target ear region of the individual in need, including the inner ear, and the individual in need is additionally administered an oral dose of aural pressure modulating agent. In some embodiments, the oral dose of aural pressure modulating agent is administered prior to administration of the auris-acceptable controlled-release aural pressure modulating agent formulation, and then the oral dose is tapered off over the period of time that the auris-acceptable controlled-release aural pressure modulating agent formulation is provided. Alternatively, the oral dose of aural pressure modulating agent is administered during administration of the auris-acceptable controlled-release aural pressure modulating agent formulation, and then the oral dose is tapered off over the period of time that the auris-acceptable controlled-release aural pressure modulating agent formulation is provided. Alternatively, the oral dose of aural pressure modulating agent is administered after administration of the auris-acceptable controlled-release aural pressure modulating agent formulation has been initiated, and then the oral dose is tapered off over the period of time that the auris-acceptable controlled-release aural pressure modulating agent formulation is provided.

In addition, the aural pressure modulating agent pharmaceutical compositions or formulations or devices included herein also include carriers, adjuvants, such as preserving, stabilizing, wetting or emulsifying agents, solution promoters, salts for regulating the osmotic pressure, and/or buffers. Such carriers, adjuvants, and other excipients will be compatible with the environment in the targeted auris structure(s). Accordingly, specifically contemplated are carriers, adjuvants and excipients that lack ototoxicity or are minimally ototoxic in order to allow effective treatment of the otic disorders contemplated herein with minimal side effects in the targeted regions or areas. To prevent ototoxicity, aural pressure modulating agent pharmaceutical compositions or formulations or devices disclosed herein are optionally targeted to distinct regions of the targeted auris structures, including but not limited to the tympanic cavity, vestibular bony and membranous labyrinths, cochlear bony and membranous labyrinths and other anatomical or physiological structures located within the auris interna.

Certain Definitions

The term "auris-acceptable" with respect to a formulation, composition or ingredient, as used herein, includes having no persistent detrimental effect on the auris interna (or inner ear) of the subject being treated. By "auris-pharmaceutically acceptable," as used herein, refers to a material, such as a carrier or diluent, which does not abrogate the biological activity or properties of the compound in reference to the auris interna (or inner ear), and is relatively or is reduced in toxicity to the auris interna (or inner ear), i.e., the material is administered to an individual without causing undesirable biological effects or interacting in a deleterious manner with any of the components of the composition in which it is contained.

As used herein, amelioration or lessening of the symptoms of a particular otic disease, disorder or condition by administration of a particular compound or pharmaceutical composition refers to any decrease of severity, delay in onset, slowing of progression, or shortening of duration, whether permanent or temporary, lasting or transient that is attributed to or associated with administration of the compound or composition.

As used herein, the terms "aural pressure modulating agent" or "aural pressure modulator" are used as synonyms and do not define the degree of efficacy. The aural pressure modulator also includes compounds that modulate the expression or post-transcriptional processing of a fluid homeostasis protein, including vasopressin and estrogen-related receptor beta protein. Additionally, vasopressin receptor or estrogen-related receptor beta modulators include compounds that influence vasopressin receptor or estrogen-related receptor beta signalling or downstream functions under the control of the vasopressin receptor or estrogen-related receptor beta, such as aquaporin function. Vasopressin receptor or estrogen-related receptor beta modulating agents includes compounds that increase and/or decrease vasopressin receptor or estrogen-related receptor beta function, including antagonists, inhibitors, agonists, partial agonists and the like.

"Antioxidants" are auris-pharmaceutically acceptable antioxidants, and include, for example, butylated hydroxytoluene (BHT), sodium ascorbate, ascorbic acid, sodium metabisulfite and tocopherol. In certain embodiments, antioxidants enhance chemical stability where required. Antioxidants are also used to counteract the ototoxic effects of certain therapeutic agents, including agents that are used in combination with the aural pressure modulating agents disclosed herein.

"Auris interna" refers to the inner ear, including the cochlea and the vestibular labyrinth, and the round window that connects the cochlea with the middle ear.

"Auris-interna bioavailability" refers to the percentage of the administered dose of compounds disclosed herein that becomes available in the inner ear of the animal or human being studied.

"Auris media" refers to the middle ear, including the tympanic cavity, auditory ossicles and oval window, which connects the middle ear with the inner ear.

"Blood plasma concentration" refers to the concentration of compounds provided herein in the plasma component of blood of a subject.

"Carrier materials" are excipients that are compatible with the aural pressure modulator, the auris interna and the release profile properties of the auris-acceptable pharmaceutical formulations. Such carrier materials include, e.g., binders, suspending agents, disintegration agents, filling agents, surfactants, solubilizers, stabilizers, lubricants, wetting agents, diluents, and the like. "Auris-pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphatidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like.

The term "diluent" refers to chemical compounds that are used to dilute the aural pressure modulator prior to delivery and which are compatible with the auris interna.

"Dispersing agents," and/or "viscosity modulating agents" are materials that control the diffusion and homogeneity of the aural pressure modulator through liquid media. Examples of diffusion facilitators/dispersing agents include but are not limited to hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also used as dispersing agents. Dispersing agents useful in liposomal dispersions and self-emulsifying dispersions of the aural pressure modulators disclosed herein are dimyristoyl phosphatidyl choline, natural phosphatidyl choline from eggs, natural phosphatidyl glycerol from eggs, cholesterol and isopropyl myristate.

"Drug absorption" or "absorption" refers to the process of movement of the aural pressure modulating agents from the localized site of administration, by way of example only, the round window membrane of the inner ear, and across a barrier (the round window membranes, as described below) into the auris interna or inner ear structures. The terms "co-administration" or the like, as used herein, are meant to encompass administration of the aural pressure modulating agents to a single patient, and are intended to include treatment regimens in which the aural pressure modulating agents are administered by the same or different route of administration or at the same or different time.

The terms "effective amount" or "therapeutically effective amount," as used herein, refer to a sufficient amount of the aural pressure modulating agent being administered that would be expected to relieve to some extent one or more of the symptoms of the disease or condition being treated. For example, the result of administration of the aural pressure modulating agents disclosed herein is reduction and/or alleviation of the signs, symptoms, or causes of improper fluid homeostasis in the inner ear. For example, an "effective amount" for therapeutic use is the amount of the aural pressure modulator, including a formulation as disclosed herein required to provide a decrease or amelioration in disease symptoms without undue adverse side effects. The term "therapeutically effective amount" includes, for example, a prophylactically effective amount. An "effective amount" of an aural pressure modulator composition disclosed herein is an amount effective to achieve a desired pharmacologic effect or therapeutic improvement without undue adverse side effects. It is understood that "an effective amount" or "a therapeutically effective amount" varies, in some embodiments, from subject to subject, due to variation in metabolism of the compound administered, age, weight, general condition of the subject, the condition being treated, the severity of the condition being treated, and the judgment of the prescribing physician. It is also understood that "an effective amount" in an extended release dosing format may differ from "an effective amount" in an immediate release dosing format based upon pharmacokinetic and pharmacodynamic considerations.

The terms "enhance" or "enhancing" refers to an increase or prolongation of either the potency or duration of a desired effect of the aural pressure modulators or a diminution of any adverse symptomatology that is consequent upon the administration of the aural pressure modulating agent. Thus, in regard to enhancing the effect of the aural pressure modulators disclosed herein, the term "enhancing" refers to the ability to increase or prolong, either in potency or duration, the effect of other therapeutic agents that are used in combination with the aural pressure modulators disclosed herein. An "enhancing-effective amount," as used herein, refers to an amount of aural pressure modulator or other therapeutic agent that is adequate to enhance the effect of another therapeutic agent or aural pressure modulator in a desired system. When used in a patient, amounts effective for this use will depend on the severity and course of the disease, disorder or condition, previous therapy, the patient's health status and response to the drugs, and the judgment of the treating physician.

The term "inhibiting" includes preventing, slowing, or reversing the development of a condition, for example, improper inner ear fluid homeostasis, or advancement of a condition in a patient necessitating treatment.

The terms "kit" and "article of manufacture" are used as synonyms.

The term "modulate" includes the interaction of a ligand with a receptor, the fluid homeostasis, or other direct or indirect targets that alter the activity of the fluid homeostasis, including, by way of example only, to inhibit the activity of vasopressin peptide, to inhibit the expression or post-transcriptional processing of the vasopression receptor protein. Additionally, modulation includes influencing the signalling or downstream functions under the control of, for example, vasopressin receptor or estrogen-related receptor beta, such as aquaporin function.

"Pharmacodynamics" refers to the factors which determine the biologic response observed relative to the concentration of drug at the desired site within the auris media and/or auris interna.

"Pharmacokinetics" refers to the factors which determine the attainment and maintenance of the appropriate concentration of drug at the desired site within the auris media and/or auris interna.

In prophylactic applications, compositions containing the aural pressure modulator described herein are administered to a patient susceptible to or otherwise at risk of a particular disease, disorder or condition, for example, a disorder of inner ear fluid homeostasis, or patients that are suffering from a disease or symptoms known to be characteristic of a disorder of inner ear fluid homeostasis, including by way of example only, Meniere's Disease, endolymphatic hydrops, progressive hearing loss, dizziness, vertigo, and tinnitus. Such an amount is defined to be a "prophylactically effective amount or dose." In this use, the precise amounts also depend on the patient's state of health, weight, and the like.

As used herein, a "pharmaceutical device" includes any composition described herein that, upon administration to an ear, provides a reservoir for extended release of an active agent described herein.

A "prodrug" refers to an aural pressure modulating agent that is converted into the parent drug in vivo. In certain embodiments, a prodrug is enzymatically metabolized by one or more steps or processes to the biologically, pharmaceutically or therapeutically active form of the compound. To produce a prodrug, a pharmaceutically active compound is modified such that the active compound will be regenerated upon in vivo administration. In one embodiment, the prodrug is designed to alter the metabolic stability or the transport characteristics of a drug, to mask side effects or toxicity, or to alter other characteristics or properties of a drug. Compounds provided herein, in some embodiments, are derivatized into suitable prodrugs.

"Solubilizers" refer to auris-acceptable compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethyl-pyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like that assist or increase the solubility of the aural pressure modulators disclosed herein.

"Stabilizers" refers to compounds such as any antioxidation agents, buffers, acids, preservatives and the like that are compatible with the environment of the auris interna. Stabilizers include but are not limited to agents that will do any of (1) improve the compatibility of excipients with a container, or a delivery system, including a syringe or a glass bottle, (2) improve the stability of a component of the composition, or (3) improve formulation stability.

"Steady state," as used herein, is when the amount of drug administered to the auris interna is equal to the amount of drug eliminated within one dosing interval resulting in a plateau or constant levels of drug exposure within the targeted structure.

As used herein, the term "subject" is used to mean an animal, preferably a mammal, including a human or non-human. The terms patient and subject may be used interchangeably.

"Surfactants" refer to compounds that are auris-acceptable, such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants are included to enhance physical stability or for other purposes.

The terms "treat," "treating" or "treatment," as used herein, include alleviating, abating or ameliorating a disease or condition, for example a disorder of inner ear fluid homeostasis, symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Other objects, features, and advantages of the methods and compositions described herein will become apparent from the following detailed description. It should be understood, however, that the detailed description and the specific examples, while indicating specific embodiments, are given by way of illustration only.

Anatomy of the Ear

Figure 4:
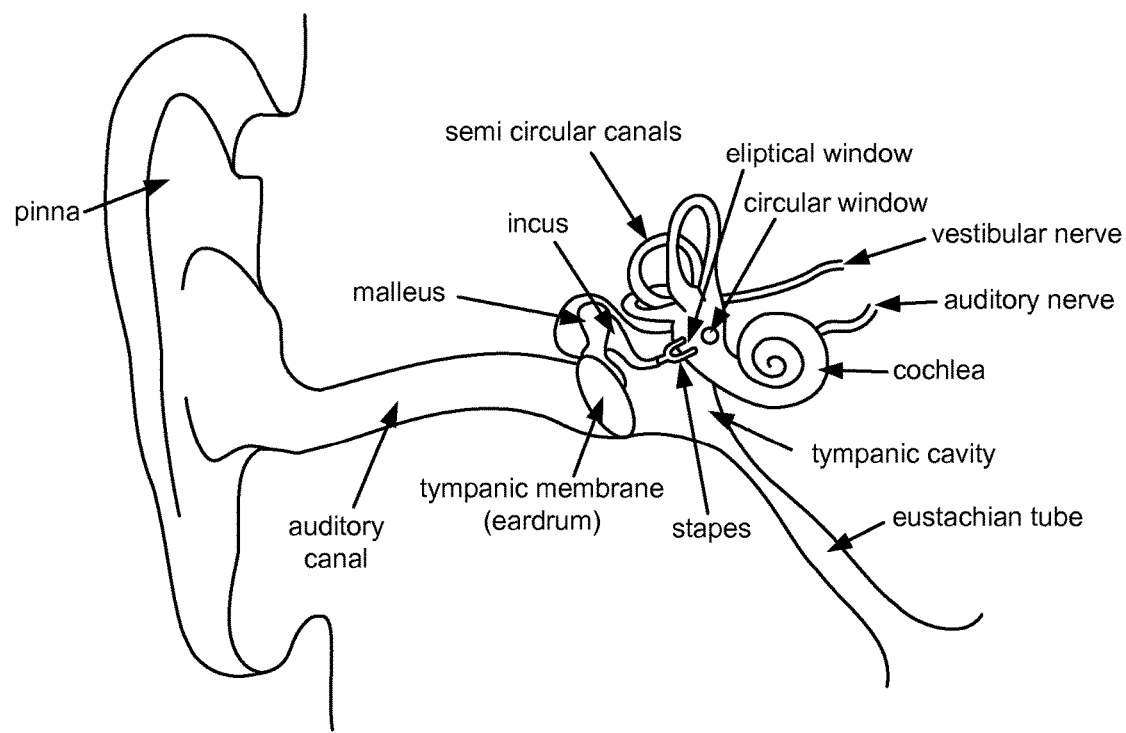
FIG. 4 illustrates the anatomy of the ear

As shown FIG. 4, the outer ear is the external portion of the organ and is composed of the pinna (auricle), the auditory canal (external auditory meatus) and the outward facing portion of the tympanic membrane, also known as the ear drum. The pinna, which is the fleshy part of the external ear that is visible on the side of the head, collects sound waves and directs them toward the auditory canal. Thus, the function of the outer ear, in part, is to collect and direct sound waves towards the tympanic membrane and the middle ear.

The middle ear is an air-filled cavity, called the tympanic cavity, behind the tympanic membrane. The tympanic membrane, also known as the ear drum, is a thin membrane that separates the external ear from the middle ear. The middle ear lies within the temporal bone, and includes within this space the three ear bones (auditory ossicles): the malleus, the incus and the stapes. The auditory ossicles are linked together via tiny ligaments, which form a bridge across the space of the tympanic cavity. The malleus, which is attached to the tympanic membrane at one end, is linked to the incus at its anterior end, which in turn is linked to the stapes. The stapes is attached to the oval window, one of two windows located within the tympanic cavity. A fibrous tissue layer, known as the annular ligament connects the stapes to the oval window. Sound waves from the outer ear first cause the tympanic membrane to vibrate. The vibration is transmitted across to the cochlea through the auditory ossicles and oval window, which transfers the motion to the fluids in the auris interna. Thus, the auditory ossicles are arranged to provide a mechanical linkage between the tympanic membrane and the oval window of the fluid-filled auris interna, where sound is transformed and transduced to the auris interna for further processing. Stiffness, rigidity or loss of movement of the auditory ossicles, tympanic membrane or oval window leads to hearing loss, e.g. otosclerosis, or rigidity of the stapes bone.

The tympanic cavity also connects to the throat via the eustachian tube. The eustachian tube provides the ability to equalize the pressure between the outside air and the middle ear cavity. The round window, a component of the auris interna but which is also accessible within the tympanic cavity, opens into the cochlea of the auris interna. The round window is covered by round window membrane, which consists of three layers: an external or mucous layer, an intermediate or fibrous layer, and an internal membrane, which communicates directly with the cochlear fluid. The round window, therefore, has direct communication with the auris interna via the internal membrane.

Movements in the oval and round window are interconnected, i.e. as the stapes bone transmits movement from the tympanic membrane to the oval window to move inward against the auris interna fluid, the round window (round window membrane) is correspondingly pushed out and away from the cochlear fluid. This movement of the round window allows movement of fluid within the cochlea, which leads in turn to movement of the cochlear inner hair cells, allowing hearing signals to be transduced. Stiffness and rigidity in round window membrane leads to hearing loss because of the lack of ability of movement in the cochlear fluid. Recent studies have focused on implanting mechanical transducers onto the round window, which bypasses the normal conductive pathway through the oval window and provides amplified input into the cochlear chamber.

Auditory signal transduction takes place in the auris interna. The fluid-filled auris interna, or inner ear, consists of two major components: the cochlear and the vestibular apparatus. The auris interna is located in part within the osseous or bony labyrinth, an intricate series of passages in the temporal bone of the skull. The vestibular apparatus is the organ of balance and consists of the three semi-circular canals and the vestibule. The three semi-circular canals are arranged relative to each other such that movement of the head along the three orthogonal planes in space can be detected by the movement of the fluid and subsequent signal processing by the sensory organs of the semi-circular canals, called the crista ampullaris. The crista ampullaris contains hair cells and supporting cells, and is covered by a dome-shaped gelatinous mass called the cupula. The hairs of the hair cells are embedded in the cupula. The semi-circular canals detect dynamic equilibrium, the equilibrium of rotational or angular movements.

When the head turns rapidly, the semicircular canals move with the head, but endolymph fluid located in the membranous semi-circular canals tends to remain stationary. The endolymph fluid pushes against the cupula, which tilts to one side. As the cupula tilts, it bends some of the hairs on the hair cells of the crista ampullaris, which triggers a sensory impulse. Because each semicircular canal is located in a different plane, the corresponding crista ampullaris of each semi-circular canal responds differently to the same movement of the head. This creates a mosaic of impulses that are transmitted to the central nervous system on the vestibular branch of the vestibulocochlear nerve. The central nervous system interprets this information and initiates the appropriate responses to maintain balance. Of importance in the central nervous system is the cerebellum, which mediates the sense of balance and equilibrium.

The vestibule is the central portion of the auris interna and contains mechanoreceptors bearing hair cells that ascertain static equilibrium, or the position of the head relative to gravity. Static equilibrium plays a role when the head is motionless or moving in a straight line. The membranous labyrinth in the vestibule is divided into two sac-like structures, the utricle and the saccule. Each structure in turn contains a small structure called a macula, which is responsible for maintenance of static equilibrium. The macula consists of sensory hair cells, which are embedded in a gelatinous mass (similar to the cupula) that covers the macula. Grains of calcium carbonate, called otoliths, are embedded on the surface of the gelatinous layer.

When the head is in an upright position, the hairs are straight along the macula. When the head tilts, the gelatinous mass and otoliths tilts correspondingly, bending some of the hairs on the hair cells of the macula. This bending action initiates a signal impulse to the central nervous system, which travels via the vestibular branch of the vestibulocochlear nerve, which in turn relays motor impulses to the appropriate muscles to maintain balance.

The cochlea is the portion of the auris interna related to hearing. The cochlea is a tapered tube-like structure which is coiled into a shape resembling a snail. The inside of the cochlea is divided into three regions, which is further defined by the position of the vestibular membrane and the basilar membrane. The portion above the vestibular membrane is the scala vestibuli, which extends from the oval window to the apex of the cochlea and contains perilymph fluid, an aqueous liquid low in potassium and high in sodium content. The basilar membrane defines the scala tympani region, which extends from the apex of the cochlea to the round window and also contains perilymph. The basilar membrane contains thousands of stiff fibers, which gradually increase in length from the round window to the apex of the cochlea. The fibers of the basement membrane vibrate when activated by sound. In between the scala vestibuli and the scala tympani is the cochlear duct, which ends as a closed sac at the apex of the cochlea. The cochlear duct contains endolymph fluid, which is similar to cerebrospinal fluid and is high in potassium.

The organ of Corti, the sensory organ for hearing, is located on the basilar membrane and extends upward into the cochlear duct. The organ of Corti contains hair cells, which have hairlike projections that extend from their free surface, and contacts a gelatinous surface called the tectorial membrane. Although hair cells have no axons, they are surrounded by sensory nerve fibers that form the cochlear branch of the vestibulocochlear nerve (cranial nerve VIII).

As discussed, the oval window, also known as the elliptical window communicates with the stapes to relay sound waves that vibrate from the tympanic membrane. Vibrations transferred to the oval window increases pressure inside the fluid-filled cochlea via the perilymph and scala vestibuli/scala tympani, which in turn causes the round window membrane to expand in response. The concerted inward pressing of the oval window/outward expansion of the round window allows for the movement of fluid within the cochlea without a change of intra-cochlear pressure. However, as vibrations travel through the perilymph in the scala vestibuli, they create corresponding oscillations in the vestibular membrane. These corresponding oscillations travel through the endolymph of the cochlear duct, and transfer to the basilar membrane. When the basilar membrane oscillates, or moves up and down, the organ of Corti moves along with it. The hair cell receptors in the Organ of Corti then move against the tectorial membrane, causing a mechanical deformation in the tectorial membrane. This mechanical deformation initiates the nerve impulse which travels via the vestibulocochlear nerve to the central nervous system, mechanically transmitting the sound wave received into signals that are subsequently processed by the central nervous system.

Diseases

Otic disorders, including auris interna disorders, produce symptoms which include but are not limited to hearing loss, nystagmus, feeling of fullness in ear, vertigo, tinnitus, inflammation, and congestion.

Meniere's Disease

Meniere's Disease is an idiopathic condition characterized by sudden attacks of vertigo, nausea and vomiting that may last for 3 to 24 hours, and may subside gradually. Progressive hearing loss, tinnitus and a sensation of pressure in the ears accompanies the disease through time. Meniere's disease appears linked to defective fluid homeostasis in the inner ear, including an increase in production or a decrease in reabsorption of inner ear fluid.

The vasopressin (VP) aquaporin 2 (AQP2) system in the inner ear, and in particular VP, has a role in regulating endolymph production, thereby increasing pressure in the vestibular and cochlear structures. VP levels are upregulated in patients with endolymphatic hydrops (Meniere's Disease), and chronic administration of VP in guinea pigs induces endolymphatic hydrops. Treatment with VP antagonists, including infusion of OPC-31260 (a competitive antagonist of $V_2$-R) into the scala tympani resulted in a marked reduction of Meniere's disease symptoms. Other VP antagonists include WAY-140288, CL-385004, tolvaptan, conivaptan, SR 121463A and VPA 985. (Sanghi et al. *Eur. Heart J.* (2005) 26:538-543; Palm et al. *Nephrol. Dial Transplant* (1999) 14:2559-2562).

Other treatments are aimed at dealing with the immediate symptoms and prevention of recurrence. Low-sodium diets, avoidance of caffeine, alcohol, and tobacco have been advocated. Medications that temporarily relieve vertigo attacks include antihistamines (including meclizine (Antivert®, Bonine®, Dramamine®, Driminate), betahistine and other antihistamines), and central nervous system agents, including barbiturates and/or benzodiazepines, including lorazepam or diazepam. Other examples of drugs that are useful in relieving symptoms include nerve blocking agents (e.g., atropine), muscarinic antagonists, including scopolamine. Nausea and vomiting are relieved by suppositories containing antipsychotic agents, including the phenothiazine agent prochlorperazine (Compazine®, Buccastem, Stemetil and Phenotil).

Surgical procedures that have been used to relieve symptoms include the destruction of vestibular and/or cochlear function to relieve vertigo symptoms. These procedures aim to either reduce fluid pressure in the inner ear and/or to destroy inner ear balance function. An endolymphatic shunt procedure, which relieves fluid pressure, is placed in the inner ear to relieve symptoms of vestibular dysfunction. Other treatments include gentamicin application, which when injected into the eardrum relieves fullness in the ear. However, gentamicin destroys sensory hair cell function, thereby eradicating inner ear balance function and causing permanent balance impairment. Severing of the vestibular nerve may also be employed, which while preserving hearing, may control vertigo.

Meniere's Syndrome

Meniere's Syndrome, which displays similar symptoms as Meniere's disease, is attributed as a secondary affliction to an unrelated disease process, e.g. thyroid disease or inner ear inflammation due to syphilis infection. Meniere's syndrome, thus, are secondary effects to various process that interfere with normal production or resorption of endolymph, including endocrine abnormalities, electrolyte imbalance, autoimmune dysfunction, medications, infections (e.g. parasitic infections) or hyperlipidemia. Treatment of patients afflicted with Meniere's Syndrome is similar to Meniere's Disease.

Vestibular Neuronitis

Vestibular neuronitis is characterized by sudden vertigo attacks, and may be caused by inflammation of the nerve to the semicircular canals likely caused by a virus. The first attack of vertigo is usually severe, leading to nystagmus, a condition characterized by the flickering of the eyes involuntarily toward the affected side. Hearing loss does not usually occur. Diagnosis of vestibular neuronitis usually involves tests for nystagmus using electronystamography, a method of electronically recording eye movements. Magnetic resonance imaging may also be performed to determine if other causes may play a role in the vertigo symptoms.

Treatment of vertigo is identical to Meniere's disease, and may include meclizine, lorazepam, prochlorperazine or scopolamine. Fluids and electrolytes may also be intravenously administered if the vomiting is severe.

Postural Vertigo

Postural vertigo, otherwise known as positional vertigo, is characterized by sudden violent vertigo that is triggered by certain head positions. This condition may be caused by damaged semicircular canals caused by physical injury to the inner ear, otitis media, ear surgery or blockage of the artery to the inner ear.

Vertigo onset in patients with postural vertigo usually develops when a person lies on one ear or tilts the head back to look up. Vertigo may be accompanied by nystagmus. Treatment of postural vertigo involves the same treatment as in Meniere's disease. In severe cases of postural vertigo, the vestibular nerve is severed to the affected semicircular canal.

Ramsay Hunt's Syndrome (Herpes Zoster Infection)

Ramsay Hunt's syndrome is caused by a herpes zoster infection of the auditory nerve. The infection may cause severe ear pain, hearing loss, vertigo, as well as blisters on the outer ear, in the ear canal, and on the skin of the face or neck supplied by the nerves. Facial muscles may also become paralyzed if the facial nerves are compressed by the swelling. Hearing loss may be temporary or permanent, with vertigo symptoms usually lasting from several days to weeks.

Treatment of Ramsay Hunt's syndrome includes administration of antiviral agents, including acyclovir. Other antiviral agents include famciclovir and valacyclovir. Combination of antiviral and corticosteroid therapy may also be employed to ameliorate herpes zoster infection. Analgesics or narcotics may also be administered to relieve the pain, and diazempam or other central nervous system agents to suppress vertigo. Capsaicin, lidocaine patches and nerve blocks may also be used. Surgery may also be performed on compressed facial nerves to relieve facial paralysis.

Sensorineural Hearing Loss

Sensorineural hearing loss occurs when the components of the inner ear or accompanying neural components are affected, and may contain a neural, i.e. when the auditory nerve or auditory nerve pathways in the brain are affected, or sensory component. Sensory hearing loss may be hereditary, or it may be caused by acoustic trauma (i.e. very loud noises), a viral infection, drug-induced or Meniere's disease. Neural hearing loss may occur as a result of brain tumors, infections, or various brain and nerve disorders, such as stroke. In some instances hearing loss is age related hearing loss. Some hereditary diseases, such as Refsum's disease (defective accumulation of branched fatty acids), may also cause neural disorders affecting hearing loss. Auditory nerve pathways may be damaged by demyelinating diseases, e.g. idiopathic inflammatory demyelinating disease (including multiple sclerosis), transverse myelitis, Devic's disease, progressive multifocal leukoencephalopathy, Guillain-Barre syndrome, chronic inflammatory demyelinating polyneuropathy and anti-MAG perpheral neuropathy.

The incidence of sudden deafness, or sensorineural hearing loss, occurs in about 1 in 5000 individuals, and may be caused by viral or bacterial infections, e.g. mumps, measles, influenza, chickenpox, cytomegalovirus, syphillis or infectious mononucleosis, or physical injury to the inner ear organ. In some cases, no cause can be identified. Tinnitus and vertigo may accompany sudden deafness, which subsides gradually. Oral corticosteroids are frequently prescribed to treat sensorineural hearing loss. In some cases, surgical intervention may be necessary.

Hearing Loss from Excessive Noise

Noise induced hearing loss may occur from prolonged exposure to loud noises, acoustic trauma such as loud music, heavy equipment or machinery, airplanes, gunfire or other human-based noises. The hearing loss occurs as result of destruction of hair cell receptors in the inner ear. This hearing loss is often accompanied by tinnitus. Permanent damage to hearing loss is often diagnosed.

Although there is currently no treatment for noise-induced hearing loss, several treatment regimens have been experimentally developed, including treatment with insulin-like growth factor 1 (IGF-1). Lee et al. *Otol. Neurotol.* (2007) 28:976-981).

Hereditary Disorders

Hereditary disorders, including Scheibe, Mondini-Michelle, Waardenburg's, Michel, Alexander's ear deformity, hypertelorism, Jervell-Lange Nielson, Refsum's and Usher's sydromes, are found in approximately 20% of patients with sensorineural hearing loss. Congenital ear malformations may result from defects in the development of the membranous labyrinthine, the osseous labyrinthine, or both. Along with profound hearing loss and vestibular function abnormalities, hereditary deformities may also be associated with other dysfunctions, including development of recurring meningitis, cerebral spinal fluid (CSF) leaks, as well as perilymphatic fistulas. Treatment of chronic infections may be necessitated in hereditary disorder patients.

Autoimmune Inner Ear Disease

Autoimmune inner ear disease (AIED) is one of the few reversible causes of sensorineural hearing loss. It is a rare disorder appearing in both adults and children that often involves a bilateral disturbance of the audio and vestibular functions of the auris interna. In many cases, AIED occurs without systemic autoimmune symptoms, but up to one-third of patients also suffer from a systemic autoimmune illness, such as inflammatory bowel disease, rheumatoid arthritis, Ankylosing spondylitis, Systemic Lupus Erythematosus (SLE), Sjögren's Syndrome, Cogan's disease, ulcerative colitis, Wegener's granulomatosis and scleroderma. Behget's disease, a multisystem disease, also commonly has audiovestibular problems. There is some evidence for food-related allergies as a cause for cochlear and vestibular autoimmunity, but there is presently no agreement as to its importance in the aetiology of the disease. A classification scheme for AIED has been developed (Harris and Keithley, (2002) Autoimmune inner ear disease, in *Otorhinolaryngology Head and Neck Surgery.* 91, 18-32).

The immune system normally performs a crucial role in protecting the inner ear from invasive pathogens such as bacteria and viruses. However, in AIED the immune system itself begins to damage the delicate inner ear tissues. The inner ear is fully capable of mounting a localized immune response to foreign antigens. When a foreign antigen enters the inner ear, it is first processed by immunocompetent cells which reside in and around the endolymphatic sac. Once the foreign antigen has been processed by these immunocompetent cells, these cells secrete various cytokines which modulate the immune response of the inner ear. One result of this cytokine release is to facilitate the influx of inflammatory cells which are recruited from the systemic circulation. These systemic inflammatory cells enter the cochlea via diapedesis through the spiral modiolar vein and its tributaries, and begin to participate in antigen uptake and deregulation just as it occurs in other parts of the body. Interleukin 1 (IL-1) plays an important role in modulating the innate (nonspecific) immune response and is a known activator of resting T helper cells and B-cells. T helper cells, once activated by IL-1, produce IL-2. IL-2 secretion results in differentiation of pluripotent T-cells into helper, cytotoxic and suppressor T-cell subtypes. IL-2 also assists T helper cells in the activation of B lymphocytes and probably plays a pivotal role in the immunoregulation of the immune response of the vestibular and cochlear regions. IL-2 is within the perilymph of the auris interna as early as 6 h after antigen challenge with peak levels at 18 h after antigen challenge. The perilymphatic levels of IL-2 then dissipate, and it is no longer present within the perilymph at 120 hours post antigen challenge.

Pharmaceutical Agents

Provided herein are aural pressure modulating compositions or formulations that ameliorate or lessen otic disorders, including disorders of inner ear fluid homeostasis, and their attendant symptoms, which include but are not limited to hearing loss, nystagmus, vertigo, tinnitus, and inflammation. Otic disorders have causes and symptoms that are responsive to the pharmaceutical agents disclosed herein, or other pharmaceutical agents. Aural pressure modulating agents which are not disclosed herein but which are useful for the amelioration or eradication of otic disorders are expressly included and intended within the scope of the embodiments presented.

Moreover, pharmaceutical agents which have been previously shown to be toxic, harmful or non-effective during systemic or localized application in other organ systems, for example through toxic metabolites formed after hepatic processing, toxicity of the drug in particular organs, tissues or systems, through high levels needed to achieve efficacy, through the inability to be released through systemic pathways or through poor pK characteristics, are useful in some embodiments herein. Accordingly, pharmaceutical agents which have limited or no systemic release, systemic toxicity, poor pK characteristics or combinations thereof are contemplated within the scope of the embodiments disclosed herein.

The aural pressure modulating formulations disclosed herein are optionally targeted directly to otic structures where treatment is needed; for example, one embodiment contemplated is the direct application of the aural pressure modulating formulations disclosed herein onto the round window membrane or the crista fenestrae cochlea of the auris interna, allowing direct access and treatment of the auris interna, or inner ear components. In other embodiments, the aural pressure modulating formulation disclosed herein is applied directly to the oval window. In yet other embodiments, direct access is obtained through microinjection directly into the auris interna, for example, through cochlear microperfusion. Such embodiments also optionally comprise a drug delivery device, wherein the drug delivery device delivers the aural pressure modulating formulations through use of a needle and syringe, a pump, a microinjection device, an in situ forming spongy material or any combination thereof.

Some pharmaceutical agents, either alone or in combination, are ototoxic. For example, gentamicin is an antibiotic that is useful in treatment of imbalance in aural pressure but is associated with ototoxicity. In some instances, the combination of an ototoxic drug (e.g., an ototoxic aural pressure modulator) in combination with an otoprotectant is protective by lessening the ototoxic effects of the drug. The localized application of a potentially ototoxic drug also lessens the toxic effects that otherwise occur through systemic application through the use of lower amounts with maintained efficacy, or the use of targeted amounts for a shorter period of time.

Moreover, some pharmaceutical excipients, diluents or carriers are potentially ototoxic. For example, benzalkonium chloride, a common preservative, is ototoxic at certain concentrations and therefore potentially harmful if introduced into the vestibular or cochlear structures. In formulating a controlled release aural pressure modulating formulation, it is advised to avoid or combine the appropriate excipients, diluents or carriers to lessen or eliminate potential ototoxic components from the formulation, or to decrease the amount of such excipients, diluents or carriers. Optionally, a controlled release aural pressure modulating formulation includes otoprotective components, such as antioxidants, alpha lipoic acid, calicum, fosfomycin or iron chelators, to counteract potential ototoxic effects that may arise from the use of specific therapeutic agents or excipients, diluents or carriers.

Vasopressin and the Vasopressin Receptor

Vasopressin (VP) is a hormone that plays an important part in circulatory and water homoeostasis. This hormone is synthesised by neurosecretory cells located predominantly in two specific hypothalamic nuclei—the supraoptic nucleus and the paraventricular nucleus. These neurons have axons that terminate in the neural lobe of the posterior pituitary gland (neurohypophysis) in which they release vasopressin. The three vasopressin receptor subtypes (VP1a, VP1b and VP2) all belong to the G-protein coupled receptor family and have differing tissue distributions. The VP1a receptor is predominantly located in the vascular smooth muscle, hepatocytes and blood platelets. The VP1b receptors are found in the anterior pituitary. The VP2 receptors are localized in the collecting duct of the kidney and regulate the presentation of aquaporin-2 channels at the apical cell surface. The effect of modulation of the VP2 subtype provides readily observed changes in urine volume and electrolyte levels to determine the pharmacological effects of anti-diuresis.

Vasopressin regulates systemic osmolality by controlling urinary volume and composition. Vasopressin is secreted in response to increases in plasma tonicity (very sensitive stimulus) or to decreases in plasma volume (less sensitive stimulus). Vasopressin mainly regulates urinary volume by binding to the VP receptor in the collecting duct of the kidney. The VP receptor also exists in the inner ear of rodents, and aquaporin-2 (AQP2), a VP mediated water channel protein, is also expressed (Kitano et al. Neuroreport (1997), 8:2289-92). Water homeostasis of the inner ear fluid was confirmed to be regulated using the VP-AQP2 system (Takeda et al. Hear Res (2000), 140:1-6; Takeda et al. Hear Res. (2003), 182:9-18). A recent study looked at tissue expression of VP2 and AQP2 in human endolymphatic sac by immunohistochemistry and noted that VP2 and AQP2 were located in the epithelial layer of the endolymphatic sac but not in surrounding connective tissue (Taguchi et al, Laryngoscope (2007), 117:695-698). Studies on the systemic administration of vasopressio in the guinea pig showed the development of endolymphatic hydrops (Takeda et al. Hear Res (2000), 140:1-6). Additionally, the aquaporin-4 knockout mouse, while otherwise healthy, is deaf (Beitz et al., Cellular and Molecular Neurobiology (2003) 23(3):315-29). This suggests that transport of water and solutes in a manner similar to that of the kidney may play a role in fluid homeostasis of the endolymphatic sac.

Vasopressin Receptor Modulators

Vasopressin receptor modulators can be differentiated based upon their efficacy relative to the vasopressin peptide hormone. A vasopressin receptor full agonist is a mimic of the native peptide. A vasopressin receptor antagonist blocks the effect of the native peptide. A partial agonist can serve as a mimic of the native peptide and induce a partial response, or in the presence of elevated levels of the native peptide, a partial agonist competes with the native peptide for receptor occupancy and provides a reduction in efficacy, relative to the native peptide alone. For a vasopressin receptor with constitutive activity, an inverse agonist serves to reverse the activity of the receptor.

Agonists of the VP2 receptor are known, including OPC-51803 and related analogs (Kondo et al., J. Med. Chem. (2000) 43:4388; Nakamura et al., Br. J. Pharmacol. (2000) 129(8):1700; Nakamure et al., J. Pharmacol. Exp. Ther. (2000) 295(3):1005) and WAY-VNA-932 (Caggiano, Drugs Gut (2002) 27(3):248). Antagonists of the VP2 receptor include lixivaptan, tolvaptan, conivaptan, SR-121463 and OPC-31260 (Martin et al., J. Am. Soc. Nephrol. (1999) 10(10):2165; Gross et al., Exp. Physiol. (2000) 85: Spec No 253S; Wong et al., Gastroent April 2000, vol 118, 4 Suppl. 2, Part 1); Norman et al., Drugs Fut. (2000), 25(11):1121; Inoue et al., Clin. Pharm. Therap. (1998) 63(5):561). In testing against the constitutively activated D136A mutant VP2 receptor, SR-1211463 and OPC-31260 behaved as inverse agonist (Morin et al., FEBS Letters (1998) 441(3): 470-75).

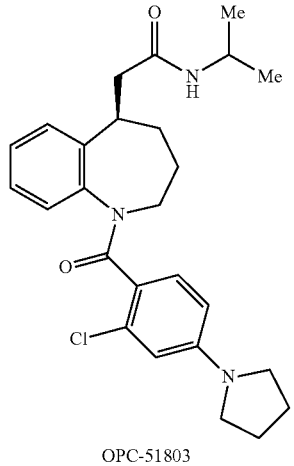

OPC-51803

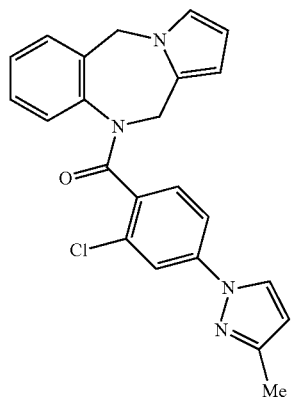

WAY-VNA-932

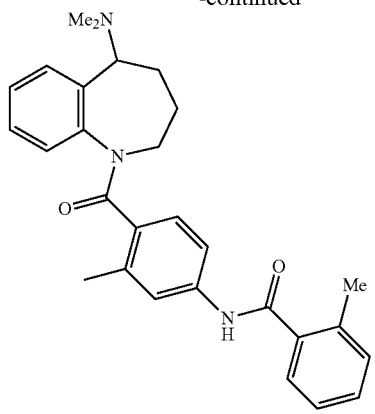

OPC-31260

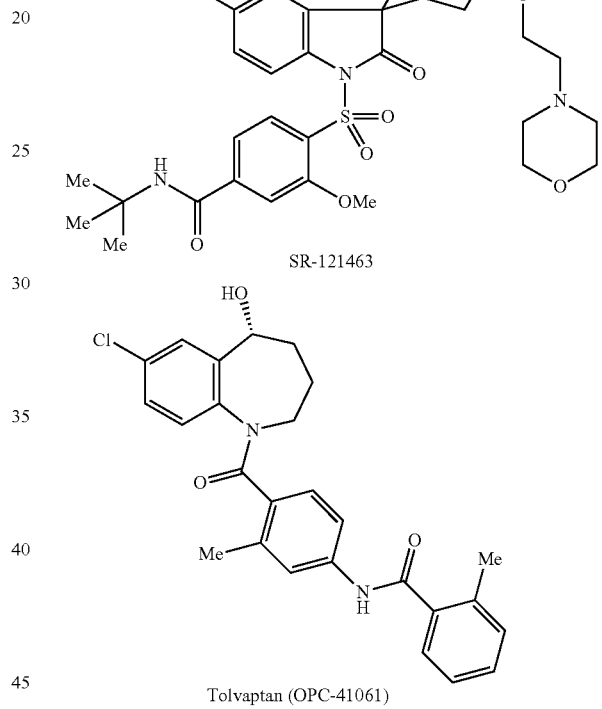

SR-121463

Tolvaptan (OPC-41061)

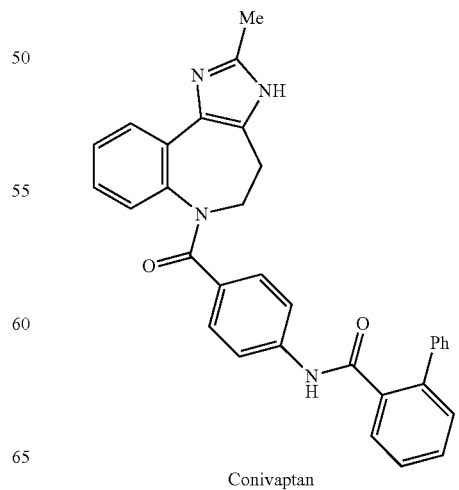

Conivaptan

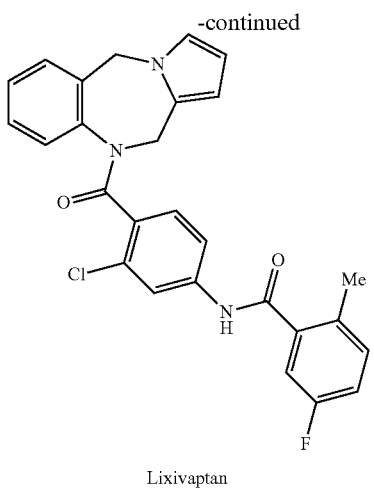

Lixivaptan

Prostaglandins

Prostaglandins are members of a group of fatty-acid derived compounds and depending upon the subtype, participate in a variety of functions, including control of constriction or dilation in vascular smooth muscle cells, aggregation or disaggregation of platelets, sensitization of spinal neurons to pain, increase or decrease in intraocular pressure, regulation of inflammatory mediation, regulation of calcium movement, control of hormone regulation and control of hormonal regulation. Prostaglandins have both paracrine and autocrine functions, and are a subclass of eicosanoid compounds.

Prostaglandin analogues, such as latanoprost, travoprost, unoprostone, minprostin F2 alpha and bimtoprost, have been shown to reduce intra-ocular pressure in glaucoma patients by enhancing the uveoscleral outflow, possibly through vasodilation mechanisms, in addition to effects on the trabecular meshwork. In sensorineural hearing loss animal models, noise exposure induces 8-isoprostaglandin F2α production in the cochlea, concomitant with an increase in vasoconstriction and reduced blood flow. Treatment with SQ29548, a specific antagonist of 8-isoprostaglandin F2α, prevents these noise-induced changes in cochlear blood flow and vascular conductance Inhibition of prostaglandin F2α function also reduces tinnitus in patients suffering from Meniere's disease, as well as improvements in hearing and vertigo. Finally, prostaglandins have been implicated in chronic inflammation associated with otitis media.

Accordingly, one embodiment disclosed herein is the use of prostaglandin modulators, including latanoprost, travoprost, unoprostone, minprostin F2-alpha, bimtoprost and SQ29548, to ameliorate or decrease inner ear and middle ear disorders, including Meniere's disease, tinnitus, vertigo, hearing loss and otitis media.

Estrogen-Related Receptor Beta Modulators

Estrogen-related receptor beta (ERR-beta; also known as Nr3b2), an orphan nuclear receptor, is specifically expressed in and controls the development of the endolymph-producing cells of the innter ear: the strial marginal cells in the cochlea and the vestibular dark cells in the ampulla and utricle. (Chen et al. *Dev. Cell*. (2007) 13:325-337). Nr3b2 expression has been localized in the endolymph-secreting strial marginal cells and vestibular dark cells of the cochlea and vestibular apparatus, respectively. Studies in knockout mice have shown that strial marginal cells in these animals fail to express multiple ion channel and transporter genes, suggesting a role in the development and/or function of endolymph producing epithelia. Moreover, conditional knockout of the Nr3b2 gene results in deafness and diminished endolymphatic fluid volume.

Other studies suggest a role for estrogen-related receptor β/NR3B2 (ERR/Nr3b2) in regulating endolymph production, and therefore pressure in the vestibular/cochlear apparatus. Treatment with antagonists to ERR/Nr3b2 may assist in reducing endolymphatic volume, and thus alter pressure in the auris interna structures. Accordingly, agents which antagonize ERR/Nr3b2 expression, protein production or protein function are contemplated as useful with the formulations disclosed herein.

Osmotic Diuretics

Contemplated for use with the compositions disclosed herein, are agents which regulate aural pressure. Accordingly, some embodiments comprise osmotic diuretics. An osmotic diuretic is a substance that produces an osmotic gradient between two spaces. In certain instances, an osmotic diuretic produces an osmotic gradient between the endolymphatic and perilymphatic spaces. In certain instances, an osmotic gradient between the endolymphatic and perilymphatic spaces exerts a dehydrating effect on the endolymphatic space. In certain instances, dehydrating the endolymphatic space decreases aural pressure.

Accordingly, in some embodiments of the compositions and formulations disclosed herein, the aural pressure modulator is an osmotic diuretic. In some embodiments, the osmotic diuretic is erythritol, mannitol, glucose, isosorbide, glycerol; urea; or combinations thereof.

Calcium Channel Blockers

Contemplated for use with the formulations disclosed herein are agents that modulate fluid homeostasis in the ear. Accordingly, some embodiments incorporate the use of ion channel modulators (e.g., potassium, sodium or calcium channel modulators, Na/K ATPase modulators, or KCNQ channel modulators) in the compositions described herein. In some instances, $Ca^{2+}$ concentration is critical for cochlear homeostasis and sensory transduction in the cochlea. Calcium channels are channels formed in the plasma membrane of neurons (amongst other cells) by integral membrane proteins. These channels conduct $Ca^+$ through a cell's plasma membrane. In neurons, the flow of $Ca^{2+}$ is partly responsible for creating and propagating action potentials in neurons. It can also be responsible for the release of certain neurotransmitters.

In some embodiments, calcium channel antagonists modulate fluid homeostasis in the ear. In some embodiments, the calcium channel antagonist is lomerizine, cinnarizine, flunarizine, or nimodipine. In some embodiments, the calcium channel antagonist is cinnarizine. In some embodiments, the calcium channel antagonist is flunarizine. In some embodiments, the calcium channel antagonist is nimodipine. In some embodiments, the calcium channel antagonist is lomerizine.

Antibiotics

Contemplated for use with the formulations disclosed herein are agents that alleviate a feeling of fullness in the ear. Accordingly, some embodiments incorporate the use of antibacterial agents including, but not limited to, amikacin, gentamicin, kanamycin, neomycin, netilmicin, streptomycin, tobramycin, paromomycin, geldanmycin, herbimycin, loracarbef, ertapenem, doripenem, imipenem, cilastatin, meropenem, cefadroxil, cefazolin, cefalotin, cefalexin, cefaclor, cefamandole, cefoxitin, defprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, teicoplanin, vancomycin, azithromycin, clarithromycin, dirithromycin, erythromycin, roxithromycin, troleandomycin, telithromycin, spectinomycin, aztreonam, amoxicillin, ampicillin, azlocillin, carbenicillin, cloxacillin, dicloxacillin, flucloxacillin, mezlocillin, meticillin, nafcillin, oxacillin, penicillin, piperacillin, ticarcillan, bacitracin, colistin, polymyxin B, ciprofloxacin, enoxacin, gatifloxacin, levofloxacin, lomefloxacin, moxifloxacin, norfloxacin, ofloxacin, trovfloxacin, mafenide, prontosil, sulfacetamide, sulfamethizole, sulfanimilimde, sulfsalazine, sulfsioxazole, trimethoprim, demeclocycline, doxycycline, minocycline, oxetracycline, tetracycline, arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinuspristin/dalfopristin, rifampin, timidazole, and combinations thereof.

RNAi

In some embodiments, where inhibition or down-regulation of a target is desired (e.g. genes ERR, and Nr3b2), RNA interference may be utilized. In some embodiments, the agent that inhibits or down-regulates the target is an siRNA molecule. In certain instances, the siRNA molecule inhibits the transcription of a target by RNA interference (RNAi). In some embodiments, a double stranded RNA (dsRNA) molecule with sequences complementary to a target is generated (e.g by PCR). In some embodiments, a 20-25 bp siRNA molecule with sequences complementary to a target is generated. In some embodiments, the 20-25 bp siRNA molecule has 2-5 bp overhangs on the 3' end of each strand, and a 5' phosphate terminus and a 3' hydroxyl terminus. In some embodiments, the 20-25 bp siRNA molecule has blunt ends. For techniques for generating RNA sequences see Molecular Cloning: A Laboratory Manual, second edition (Sambrook et al., 1989) and Molecular Cloning: A Laboratory Manual, third edition (Sambrook and Russel, 2001), jointly referred to herein as "Sambrook"); Current Protocols in Molecular Biology (F. M. Ausubel et al., eds., 1987, including supplements through 2001); Current Protocols in Nucleic Acid Chemistry John Wiley & Sons, Inc., New York, 2000) which are hereby incorporated by reference for such disclosure.

In some embodiments, the dsRNA or siRNA molecule is incorporated into a controlled-release auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the inner ear. In some embodiments, the auris-acceptable microsphere or microparticle, hydrogel, liposome, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

In certain instances, after administration of the dsRNA or siRNA molecule, cells at the site of administration (e.g. the cells of cochlea, organ of Corti, and/or the vestibular labyrinth) are transformed with the dsRNA or siRNA molecule. In certain instances following transformation, the dsRNA molecule is cleaved into multiple fragments of about 20-25 bp to yield siRNA molecules. In certain instances, the fragments have about 2 bp overhangs on the 3' end of each strand.

In certain instances, an siRNA molecule is divided into two strands (the guide strand and the anti-guide strand) by an RNA-induced Silencing Complex (RISC). In certain instances, the guide strand is incorporated into the catalytic component of the RISC (i.e. argonaute). In certain instances, the guide strand binds to a complementary target mRNA sequence. In certain instances, the RISC cleaves the target mRNA. In certain instances, the expression of the target gene is down-regulated.

In some embodiments, a sequence complementary to a target is ligated into a vector. In some embodiments, the sequence is placed between two promoters. In some embodiments, the promoters are orientated in opposite directions. In some embodiments, the vector is contacted with a cell. In certain instances, a cell is transformed with the vector. In certain instances following transformation, sense and anti-sense strands of the sequence are generated. In certain instances, the sense and anti-sense strands hybridize to form a dsRNA molecule which is cleaved into siRNA molecules. In certain instances, the strands hybridize to form an siRNA molecule. In some embodiments, the vector is a plasmid (e.g pSUPER; pSUPER.neo; pSUPER.neo+gfp).

In some embodiments, the vector is incorporated into a controlled-release auris-acceptable microsphere or microparticle, hydrogel, liposome, or thermoreversible gel. In some embodiments, the auris-acceptable microsphere, hydrogel, xerogel, liposome, paint, foam, in situ forming spongy material, nanocapsule or nanosphere or thermoreversible gel is injected into the inner ear. In some embodiments, the auris-acceptable microsphere or microparticle, hydrogel, liposome, actinic radiation curable gel, or thermoreversible gel. In some embodiments, the auris-acceptable microsphere, hydrogel, liposome, paint, foam, in situ forming spongy material, nanocapsule or nanosphere or thermoreversible gel is injected into the cochlea, the organ of Corti, the vestibular labyrinth, or a combination thereof.

In some embodiments, the compositions described herein have a concentration of active pharmaceutical ingredient between about 0.01% to about 90%, between about 0.01% to about 50%, between about 0.1% to about 70%, between about 0.1% to about 50%, between about 0.1% to about 40%, between about 0.1% to about 30%, between about 0.1% to about 20%, between about 0.1% to about 10%, or between about 0.1% to about 5%, of the active ingredient, or pharmaceutically acceptable prodrug or salt thereof, by weight of the composition. In some embodiments, the compositions described herein have a concentration of active pharmaceutical agent between about 1% to about 50%, between about 5% to about 50%, between about 10% to about 40%, or between about 10% to about 30%, of the active ingredient, or pharmaceutically acceptable prodrug or salt thereof, by weight of the composition. In some embodiments, formulations described herein comprise about 70% by weight of an aural pressure modulating agent by weight of the formulation. In some embodiments, formulations described herein comprise about 60% by weight of an aural pressure modulating agent by weight of the formulation. In some embodiments, formulations described herein comprise about 50% by weight of an aural pressure modulating agent by weight of the formulation. In some embodiments, formulations described herein comprise about 40% by weight of an aural pressure modulating agent by weight of the formulation. In some embodiments, formulations described herein comprise about 30% by weight of an aural pressure modulating agent by weight of the formulation. In some embodiments, formulations described herein comprise about 20% by weight of an aural pressure modulating agent by weight of the formulation. In some embodiments, formulations described herein comprise about 15% by weight of an aural pressure modulating agent, or pharmaceutically acceptable prodrug or salt thereof, by weight of the formulation. In some embodiments, formulations described herein comprise about 10% by weight of an aural pressure modulating agent by weight of the formulation. In some embodiments, formulations described herein comprise about 5% by weight of an aural pressure modulating agent, or pharmaceutically acceptable prodrug or salt thereof, by weight of the formulation. In some embodiments, formulations described herein comprise about 2.5% by weight of an aural pressure modulating agent, or pharmaceutically acceptable prodrug or salt thereof, by weight of the formulation. In some embodiments, formulations described herein comprise about 1% by weight of an aural pressure modulating agent, or pharmaceutically acceptable prodrug or salt thereof, by weight of the formulation. In some embodiments, formulations described herein comprise about 0.5% by weight of an aural pressure modulating agent, or pharmaceutically acceptable prodrug or salt thereof, by weight of the formulation. In some embodiments, formulations described herein comprise about 0.1% by weight of an aural pressure modulating agent, or pharmaceutically acceptable prodrug or salt thereof, by weight of the formulation. In some embodiments, formulations described herein comprise about 0.01% by weight of an aural pressure modulating agent, or pharmaceutically acceptable prodrug or salt thereof, by weight of the formulation. In some embodiments, the formulations described herein have a concentration of active pharmaceutical ingredient, or pharmaceutically acceptable prodrug or salt thereof, between about 0.1 to about 70 mg/mL, between about 0.5 mg/mL to about 70 mg/mL, between about 0.5 mg/mL to about 50 mg/mL, between about 0.5 mg/mL to about 20 mg/mL, between about 1 mg to about 70 mg/mL, between about 1 mg to about 50 mg/mL, between about 1 mg/mL and about 20 mg/mL, between about 1 mg/mL to about 10 mg/mL, or between about 1 mg/mL to about 5 mg/mL, of the active agent, or pharmaceutically acceptable prodrug or salt thereof, by volume of the formulation.

Combination Therapy

In some embodiments, the compositions disclosed herein further comprise an additional therapeutic agent. In some embodiments, the additional therapeutic agent is a diuretic, an anti-TNF agent, an anti-emetic agent, an anti-vertigo agent, a local acting anesthetic agent, an anti-anxiety agent, a corticosteroid, an anti-histamine, or combinations thereof. In some embodiments, the additional therapeutic agent is an otoprotectant, a Na/K ATPase modulator, a KCNQ channel modulator, or combinations thereof. Any combination of one or more pharmaceutical agents (e.g., aural pressure modulators) and one or more additional therapeutic agents is compatible with the compositions and devices described herein.

Diuretic Agents

Contemplated for use in combination with the aural pressure modulating formulations disclosed herein are diuretic agents. A diuretic agent is a drug that elevates the rate of urination. Such diuretics include triamterene, amiloride, bendroflumethiazide, hydrochlorothiazide, furosemide, torsemide, bumetanide, acetazolamide, dorzolamide and combinations thereof.

Anti-TNF Agents

Contemplated for use in combination with the aural pressure modulating formulations disclosed herein are anti-TNF agents which reduce or ameliorate symptoms or effects (e.g., aural pressure) as a result of an autoimmune disease and/or inflammatory disorder, including AIED. Autoimmune deficiencies may be a contributing factor to otic disorders such as Meniere's disease. Accordingly, some embodiments incorporate the use of agents which block the effects of TNF-α, including anti-TNF agents. By way of example only, anti-TNF agents include etanercept (ENBREL®), infliximab (REMICADE®), adalimumab (HUMIRA®), and golimumab (CNTO 148) or combinations thereof. Infliximab and adalimumab are anti-TNF monoclonal antibodies, and etanercept is a fusion protein designed to bind specifically to the TNF protein. All are currently approved for use in the treatment of rheumatoid arthritis. Golimumab, which is currently in Phase 3 clinical trials for rheumatoid arthritis, psoriatic arthritis and ankylosing spondylitis, is a fully-humanized anti-TNF-alpha IgG1 monoclonal antibody that targets and neutralizes both the soluble and the membrane-bound form of TNF. Other antagonists to TNF, by way of example only, include TNF receptors (pegylated soluble TNF receptor type 1; Amgen); TNF binding factors (Onercept; Serono); TNF antibodies (US Patent App. No. 2005/0123541; US Patent App. No. 2004/0185047); single domain antibodies against the p55 TNF receptor (US Patent App. No. 2008/00088713); soluble TNF receptors (US Patent App. No. 2007/0249538); fusion polypeptides binding to TNF (US Patent App. No. 2007/0128177); TNF-α converting enzyme inhibitors (Skotnicki et al., Annual Reports in Medicinal Chemistry (2003), 38, 153-162); IKK inhibitors (Karin et al., Nature Reviews Drug Discovery (2004), 3, 17-26) and flavone derivatives (US Patent App. No. 2006/0105967), all of which are incorporated by reference for such disclosure. The use of onercept, a soluble TNF p55 receptor, was discontinued in 2005. Three phase-III clinical trials reported patients diagnosed with fatal sepsis. A risk to benefit analysis was subsequently performed, resulting in the discontinuation of the clinical trials. As discussed above, the embodiments herein specifically contemplate the use of anti-TNF agents which have been previously shown to have limited or no systemic release, systemic toxicity, poor pK characteristics of combinations thereof.

It is contemplated that the localized application of the anti-TNF agents in combination with aural pressure modulators to the target otic structures for treatment of autoimmune and/or inflammatory disorders will result in the reduction or elimination of these adverse side effects experienced with systemic treatment. Moreover, localized treatment with the anti-TNF agents contemplated herein will also reduce the amount of agent needed for effective treatment of the targeted disorder due, for example, to the existence of the biological blood barrier in the auris interna.

Corticosteroids

Contemplated for use in combination with the aural pressure modulating agent formulations disclosed herein are corticosteroid agents which reduce or ameliorate symptoms or effects (e.g., sensation of fullness in the ear) as a result of an autoimmune disease and/or inflammatory disorder, including AIED. Such autoimmune response may be a contributing factor to otic disorders such as Meniere's disease. In some instances, corticosteroids alleviate aural fullness. In some embodiments, corticosteroids are contemplated as monotherapy. Such steroids include prednisolone, dexamethasone, dexamethasone phosphate, beclomethasone, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide and combinations thereof.

Anti-Emetic Agents/Central Nervous System Agents

Anti-Emetic agents are optionally used in combination with the aural pressure modulator formulations disclosed herein. Anti-emetic agents include antihistamines and central nervous agents, including anti-psychotic agents, barbiturates, benzodiazepines and phenothiazines. Other anti-emetic agents include the serotonin receptor antagonists, which include dolasetron, granisetron, ondansetron, tropisetron, palonosetron, and combinations thereof; dopamine antagonists, including domperidone, properidol, haloperidol, chlorpromazine, promethazine, prochlorperazine and combinations thereof; cannabinoids, including dronabinol, nabilone, sativex, and combinations thereof; anticholinergics, including scopolamine; and steroids, including dexamethasone; trimethobenzamine, emetrol, propofol, muscimol, and combinations thereof.

Optionally, Central Nervous System agents and barbiturates are useful in the treatment of nausea and vomiting symptoms that accompany an otic disorder. When used, an appropriate barbiturate and/or central nervous system agent is selected to relieve or ameliorate specific symptoms without possible side effects, including ototoxicity. Moreover, as discussed above, targeting of the drugs to the round window membrane of the auris interna reduces possible side effects and toxicity caused by systemic administration of these drugs. Barbiturates, which act as a central nervous system depressant, include allobarbital, alphenal, amobarbital, aprobarbital, barnexaclone, barbital, brallobarbital, butabarbital, butalbital, butallylonal, butobarbital, corvalol, crotylbarbital, cyclobarbital, cyclopal, ethallobarbital, febarbamate, heptabarbital, hexethal, hexobarbital, metharbital, methohexital, methylphenobarbital, narcobarbital, nealbarbital, pentobarbital, phenobarbital, primidone, probarbital, propallylonal, proxibarbital, reposal, secobarbital, sigmodal, sodium thiopental, talbutal, thialbarbital, thiamylal, thiobarbital, thiobutabarbital, tuinal, valofane, vinbarbital, vinylbital, and combinations thereof.

Other central nervous system agents which are optionally used in conjunction with the aural pressure modulator formulations disclosed herein include benzodiazepines or phenothiazines. Useful benzodiazepines include, but are not limited to diazepam, lorazepam, oxazepam, prazepam, alprazolam, bromazepam, chlordiazepoxide, clonazepam, clorazepate, brotizolam, estazolam, flunitrazepam, flurazepam, loprazolam, lormetazepam, midazolam, nimetazepam, nitrazepam, ternazepam, triazolam, and combinations thereof. Examples of phenothiazines include prochlorperazine, chlorpromazine, promazine, triflupromazine, levopromazine, methotrimepramazine, mesoridazine, thiroridazine, fluphenazine, perphenazine, flupentixol, trifluoperazine, and combinations thereof. In some embodiments, nerve blocking agents (e.g., atropine) are used in conjunction with the aural pressure modulator formulations disclosed herein. In some instances, CNS modulators relieve pressure in the ear.

Antihistamines, or histamine antagonists, act to inhibit the release or action of histamine. Antihistamines that target the H1 receptor are useful in the alleviation or reduction of nausea and vomiting symptoms that are associated with otic disorders. Such antihistamines include, but are not limited to, meclizine, diphenhydramine, loratadine and quetiapine. Other antihistamines include mepyramine, piperoxan, antazoline, carbinoxamine, doxylamine, clemastine, dimenhydrinate, pheniramine, chlorphenamine, chlorpheniramine, dexchlorpheniramine, brompheniramine, triprolidine, cyclizine, chlorcyclizine, hydroxyzine, promethazine, alimemazine, trimeprazine, cyproheptadine, azatadine, ketotifen, oxatomide and combinations thereof.

Otoprotectants

In some embodiments, any otic formulation described herein further comprises otoprotectants that reduce, inhibit or ameliorate the ototoxicity of aural pressure modulating agents such as vasopressin modulators or antibiotics as described herein. Examples of otoprotectants include, and are not limited to, thiols and/or thiol derivatives and/or pharmaceutically acceptable salts, or derivatives (e.g. pro-drugs) thereof (e.g., D-methionine, L-methionine, ethionine, hydroxylmethionine, methioninol, amifostine, mesna (sodium 2-sulfanylethanesulfonate), a mixture of D and L methionine, normethionine, homomethionine, S-adenosyl-L-methionine), diethyldithiocarbamate, ebselen (2-phenyl-1,2-benzisoselenazol-3(2H)-one), sodium thiosulfate, AM-111 (a cell permeable JNK inhibitor, (Laboratoires Auris SAS)), leucovorin, leucovorin calcium, dexrazoxane, piracetam, Oxiracetam, Aniracetam, Pramiracetam, Phenylpiracetam (Carphedon), Etiracetam, Levetiracetam, Nefiracetam, Nicoracetam, Rolziracetam, Nebracetam, Fasoracetam, Coluracetam, Dimiracetam, Brivaracetam, Seletracetam, Rolipramand or combinations thereof. Otoprotectants allow for the administration of otic agents (e.g., aural pressure modulators described herein) at doses that are higher than conventional doses; the otic agents would otherwise be systemically administered at lower doses because of associated ototoxicity.

Presented below (Table 1) are examples of active agents contemplated for use with the formulations and devices disclosed herein. One or more active agents are used in any of the formulations or devices described herein.

Active Agents (including pharmaceutically acceptable salts of these active agents) for use with the Formulations Disclosed Herein

TABLE 1

| Auris Condition | Therapeutic Agent |
| --- | --- |
| Benign Paroxysmal Positional Vertigo | Diphenhydramine |
| Benign Paroxysmal Positional Vertigo | Lorazepam |
| Benign Paroxysmal Positional Vertigo | Meclizine |
| Benign Paroxysmal Positional Vertigo | Oldansetron |
| Hearing Loss | Estrogen |
| AIED | lixivaptan |
| AIED | tovaptan |
| Hearing Loss | Estrogen and progesterone (E + P) |
| Hearing Loss | Folic acid |
| Hearing Loss | Lactated Ringer's with 0.03% Ofloxacin |
| Hearing Loss | Methotrexate |
| Hearing Loss | N-acetyl cysteine |
| Meniere's Disease | Betahistine |
| Meniere's Disease | Sildenafil |
| Meniere's Disease | conivaptan |
| Middle Ear Effusion | Pneumonococcal vaccine |

TABLE 1-continued

| Auris Condition | Therapeutic Agent |
| --- | --- |
| Otitis Externa | Diclofenac sodium; dexotc |
| Otitis Externa, Acute | AL-15469A/AL-38905 |
| Otitis Media | Amoxicillin/clavulanate |
| Otitis Media | Dornase alfa |
| Otitis Media | Echinacea purpurea |
| Otitis Media | Faropenem medoxomil |
| Otitis Media | Levofloxacin |
| Otitis Media | PNCRM9 |
| Otitis Media | Pneumococcal vaccine |
| Otitis Media | Telithromycin |
| Otitis Media | Zmax |
| Otitis Media with Effusion | Lansoprazole |
| Otitis Media, Acute | AL-15469A; AL-38905 |
| Otitis Media, Acute | Amoxicillin |
| Auris Condition | Therapeutic Agent |
| Otitis Media, Acute | Amoxicillin-clavulanate |
| Otitis Media, Acute | Azithromycin |
| Otitis Media, Acute | Azithromycin SR |
| Otitis Media, Acute | Cefdinir |
| Otitis Media, Acute | Hyland's earache drops |
| Otitis Media, Acute | Montelukast |
| Otitis Media, Acute | Pneumonococcal vaccine |
| Otitis Media, Acute with Typanostomy Tubes | AL-15469A/AL38905 |
| Otitis Media, Chronic | Sulfamethoxazole-trimethoprim |
| Otitis Media, Suppurative | Azithromycin |
| Otitis Media, Suppurative | Telithromycin |
| Otosclerosis | Acetylcysteine |
| Ototoxicity | Aspirin |
| Tinnitus | Acamprosate |
| Tinnitus | Gabapentin |
| Tinnitus | Modafinil |
| Tinnitus | Neramexane |
| Tinnitus | Neramexane mesylate |
| Tinnitus | Piribedil |
| Tinnitus | Vardenafil |
| Tinnitus | Vestipitant + Paroxetine |
| Tinnitus | Vestiplitant |
| Tinnitus | Zinc sulfate |

General Methods of Sterilization

Provided herein are otic compositions that ameliorate or lessen otic disorders described herein. Further provided herein are methods comprising the administration of said otic compositions. In some embodiments, the compositions or devices are sterilized. Included within the embodiments disclosed herein are means and processes for sterilization of a pharmaceutical composition or device disclosed herein for use in humans. The goal is to provide a safe pharmaceutical product, relatively free of infection causing micro-organisms. The U.S. Food and Drug Administration has provided regulatory guidance in the publication "Guidance for Industry: Sterile Drug Products Produced by Aseptic Processing" available at: http://www.fda.gov/cder/guidance/5882fn-1.htm, which is incorporated herein by reference in its entirety.

As used herein, sterilization means a process used to destroy or remove microorganisms that are present in a product or packaging. Any suitable method available for sterilization of objects and compositions is used. Available methods for the inactivation of microorganisms include, but are not limited to, the application of extreme heat, lethal chemicals, or gamma radiation. In some embodiments is a process for the preparation of an otic therapeutic formulation comprising subjecting the formulation to a sterilization method selected from heat sterilization, chemical sterilization, radiation sterilization or filtration sterilization. The method used depends largely upon the nature of the device or composition to be sterilized. Detailed descriptions of many methods of sterilization are given in Chapter 40 of Remington: The Science and Practice of Pharmacy published by Lippincott, Williams & Wilkins, and is incorporated by reference with respect to this subject matter.

Sterilization by Heat

Many methods are available for sterilization by the application of extreme heat. One method is through the use of a saturated steam autoclave. In this method, saturated steam at a temperature of at least 121° C. is allowed to contact the object to be sterilized. The transfer of heat is either directly to the microorganism, in the case of an object to be sterilized, or indirectly to the microorganism by heating the bulk of an aqueous solution to be sterilized. This method is widely practiced as it allows flexibility, safety and economy in the sterilization process.

Dry heat sterilization is a method which is used to kill microorganisms and perform depyrogenation at elevated temperatures. This process takes place in an apparatus suitable for heating HEPA-filtered microorganism-free air to temperatures of at least 130-180° C. for the sterilization process and to temperatures of at least 230-250° C. for the depyrogenation process. Water to reconstitute concentrated or powdered formulations is also sterilized by autoclave. In some embodiments, the formulations described herein comprise micoronized aural pressure modulating agents (e.g., micro-lixivaptan) that are sterilized by dry heating, e.g., heating for about 7-11 hours at internal powder temperatures of 130-140° C., or for 1-2 hours at internrnal tempearatures of 150-180° C.

Chemical Sterilization

Chemical sterilization methods are an alternative for products that do not withstand the extremes of heat sterilization. In this method, a variety of gases and vapors with germicidal properties, such as ethylene oxide, chlorine dioxide, formaldehyde or ozone are used as the anti-apoptotic agents. The germicidal activity of ethylene oxide, for example, arises from its ability to serve as a reactive alkylating agent. Thus, the sterilization process requires the ethylene oxide vapors to make direct contact with the product to be sterilized.

Radiation Sterilization

One advantage of radiation sterilization is the ability to sterilize many types of products without heat degradation or other damage. The radiation commonly employed is beta radiation or alternatively, gamma radiation from a $^{60}Co$ source. The penetrating ability of gamma radiation allows its use in the sterilization of many product types, including solutions, compositions and heterogeneous mixtures. The germicidal effects of irradiation arise from the interaction of gamma radiation with biological macromolecules. This interaction generates charged species and free radicals. Subsequent chemical reactions, such as rearrangements and cross-linking processes, result in the loss of normal function for these biological macromolecules. The formulations described herein are also optionally sterilized using beta irradiation.

Filtration

Filtration sterilization is a method used to remove but not destroy microorganisms from solutions. Membrane filters are used to filter heat-sensitive solutions. Such filters are thin, strong, homogenous polymers of mixed cellulosic esters (MCE), polyvinylidene fluoride (PVF; also known as PVDF), or polytetrafluoroethylene (PTFE) and have pore sizes ranging from 0.1 to 0.22 µm. Solutions of various characteristics are optionally filtered using different filter membranes. For example, PVF and PTFE membranes are well suited to filtering organic solvents while aqueous solutions are filtered through PVF or MCE membranes. Filter apparatus are available for use on many scales ranging from the single point-of-use disposable filter attached to a syringe up to commercial scale filters for use in manufacturing plants. The membrane filters are sterilized by autoclave or chemical sterilization. Validation of membrane filtration systems is performed following standardized protocols (Microbiological Evaluation of Filters for Sterilizing Liquids, Vol 4, No. 3. Washington, D.C: Health Industry Manufacturers Association, 1981) and involve challenging the membrane filter with a known quantity (ca. $10^{71}$ cm$^2$) of unusually small microorganisms, such as Brevundimonas diminuta (ATCC 19146).

Pharmaceutical compositions are optionally sterilized by passing through membrane filters. Formulations comprising nanoparticles (U.S. Pat. No. 6,139,870) or multilamellar vesicles (Richard et al., International Journal of Pharmaceutics (2006), 312(1-2):144-50) are amenable to sterilization by filtration through 0.22 μm filters without destroying their organized structure.

In some embodiments, the methods disclosed herein comprise sterilizing the formulation (or components thereof) by means of filtration sterilization. In another embodiment the auris-acceptable otic therapeutic agent formulation comprises a particle wherein the particle formulation is suitable for filtration sterilization. In a further embodiment said particle formulation comprises particles of less than 300 nm in size, of less than 200 nm in size, of less than 100 nm in size. In another embodiment the auris-acceptable formulation comprises a particle formulation wherein the sterility of the particle is ensured by sterile filtration of the precursor component solutions. In another embodiment the auris-acceptable formulation comprises a particle formulation wherein the sterility of the particle formulation is ensured by low temperature sterile filtration. In a further embodiment, low temperature sterile filtration is carried out at a temperature between 0 and 30° C., between 0 and 20° C., between 0 and 10° C., between 10 and 20° C., or between 20 and 30° C.

In another embodiment is a process for the preparation of an auris-acceptable particle formulation comprising: filtering the aqueous solution containing the particle formulation at low temperature through a sterilization filter; lyophilizing the sterile solution; and reconstituting the particle formulation with sterile water prior to administration. In some embodiments, a formulation described herein is manufactured as a suspension in a single vial formulation containing the micronized active pharmaceutical ingredient. A single vial formulation is prepared by aseptically mixing a sterile poloxamer solution with sterile micronized active ingredient (e.g., lixivaptan) and transferring the formulation to sterile pharmaceutical containers. In some embodiments, a single vial containing a formulation described herein as a suspension is resuspended before dispensing and/or administration.

In specific embodiments, filtration and/or filling procedures are carried out at about 5° C. below the gel temperature (Tgel) of a formulation described herein and with viscosity below a theoretical value of 100 cP to allow for filtration in a reasonable time using a peristaltic pump.

In another embodiment the auris-acceptable otic therapeutic agent formulation comprises a nanoparticle formulation wherein the nanoparticle formulation is suitable for filtration sterilization. In a further embodiment the nanoparticle formulation comprises nanoparticles of less than 300 nm in size, of less than 200 nm in size, or of less than 100 nm in size. In another embodiment the auris-acceptable formulation comprises a microsphere formulation wherein the sterility of the microsphere is ensured by sterile filtration of the precursor organic solution and aqueous solutions. In another embodiment the auris-acceptable formulation comprises a thermoreversible gel formulation wherein the sterility of the gel formulation is ensured by low temperature sterile filtration. In a further embodiment, the low temperature sterile filtration occurs at a temperature between 0 and 30° C., or between 0 and 20° C., or between 0 and 10° C., or between 10 and 20° C., or between 20 and 30° C. In another embodiment is a process for the preparation of an auris-acceptable thermoreversible gel formulation comprising: filtering the aqueous solution containing the thermoreversible gel components at low temperature through a sterilization filter; lyophilizing the sterile solution; and reconstituting the thermoreversible gel formulation with sterile water prior to administration.

In certain embodiments, the active ingredients are dissolved in a suitable vehicle (e.g. a buffer) and sterilized separately (e.g. by heat treatment, filtration, gamma radiation). In some embodiments, the active ingredients are sterilized separately in a dry state. In some instances, the active ingredients are sterilized as a suspension or as a colloidal suspension. The remaining excipients (e.g., fluid gel components present in auris formulations) are sterilized in a separate step by a suitable method (e.g. filtration and/or irradiation of a cooled mixture of excipients); the two solutions that are separately sterilized are then mixed aseptically to provide a final auris formulation. In some instances, the final aseptic mixing is performed just prior to administration of a formulation described herein.

In some instances, conventionally used methods of sterilization (e.g., heat treatment (e.g., in an autoclave), gamma irradiation, filtration) lead to irreversible degradation of polymeric components (e.g., thermosetting, gelling or mucoadhesive polymer components) and/or the active agent in the formulation. In some instances, sterilization of an auris formulation by filtration through membranes (e.g., 0.2 μM membranes) is not possible if the formulation comprises thixotropic polymers that gel during the process of filtration.

Accordingly, provided herein are methods for sterilization of auris formulations that prevent degradation of polymeric components (e.g., thermosetting and/or gelling and/or mucoadhesive polymer components) and/or the active agent during the process of sterilization. In some embodiments, degradation of the active agent (e.g., any therapeutic otic agent described herein) is reduced or eliminated through the use of specific pH ranges for buffer components and specific proportions of gelling agents in the formulations. In some embodiments, the choice of an appropriate gellling agent and/or thermosetting polymer allows for sterilization of formulations described herein by filtration. In some embodiments, the use of an appropriate thermosetting polymer and an appropriate copolymer (e.g., a gelling agent) in combination with a specific pH range for the formulation allows for high temperature sterilization of formulations described with substantially no degradation of the therapeutic agent or the polymeric excipients. An advantage of the methods of sterilization provided herein is that, in certain instances, the formulations are subjected to terminal sterilization via autoclaving without any loss of the active agent and/or excipients and/or polymeric components during the sterilization step and are rendered substantially free of microbes and/or pyrogens.

Microorganisms

Provided herein are auris-acceptable compositions or devices that ameliorate or lessen otic disorders described herein. Further provided herein are methods comprising the administration of said otic compositions. In some embodiments, the compositions or devices are substantially free of microorganisms. Acceptable bioburden or sterility levels are based on applicable standards that define therapeutically acceptable compositions, including but not limited to United States Pharmacopeia Chapters <1111> et seq. For example, acceptable sterility (e.g., bioburden) levels include about 10 colony forming units (cfu) per gram of formulation, about 50 cfu per gram of formulation, about 100 cfu per gram of formulation, about 500 cfu per gram of formulation or about 1000 cfu per gram of formulation. In some embodiments, acceptable bioburden levels or sterility for formulations include less than 10 cfu/mL, less that 50 cfu/mL, less than 500 cfu/mL or less than 1000 cfu/mL microbial agents. In addition, acceptable bioburden levels or sterility include the exclusion of specified objectionable microbiological agents. By way of example, specified objectionable microbiological agents include but are not limited to *Escherichia coli* (*E. coli*), *Salmonella* sp., *Pseudomonas aeruginosa* (*P. aeruginosa*) and/or other specific microbial agents.

Sterility of the auris-acceptable otic therapeutic agent formulation is confirmed through a sterility assurance program in accordance with United States Pharmacopeia Chapters <61>, <62> and <71>. A key component of the sterility assurance quality control, quality assurance and validation process is the method of sterility testing. Sterility testing, by way of example only, is performed by two methods. The first is direct inoculation wherein a sample of the composition to be tested is added to growth medium and incubated for a period of time up to 21 days. Turbidity of the growth medium indicates contamination. Drawbacks to this method include the small sampling size of bulk materials which reduces sensitivity, and detection of microorganism growth based on a visual observation. An alternative method is membrane filtration sterility testing. In this method, a volume of product is passed through a small membrane filter paper. The filter paper is then placed into media to promote the growth of microorganisms. This method has the advantage of greater sensitivity as the entire bulk product is sampled. The commercially available Millipore Steritest sterility testing system is optionally used for determinations by membrane filtration sterility testing. For the filtration testing of creams or ointments Steritest filter system No. TLHVSL210 are used. For the filtration testing of emulsions or viscous products Steritest filter system No. TLAREM210 or TDAREM210 are used. For the filtration testing of pre-filled syringes Steritest filter system No. TTHASY210 are used. For the filtration testing of material dispensed as an aerosol or foam Steritest filter system No. TTHVA210 are used. For the filtration testing of soluble powders in ampoules or vials Steritest filter system No. TTHADA210 or TTHADV210 are used.

Testing for *E. coli* and *Salmonella* includes the use of lactose broths incubated at 30-35° C. for 24-72 hours, incubation in MacConkey and/or EMB agars for 18-24 hours, and/or the use of Rappaport medium. Testing for the detection of *P. aeruginosa* includes the use of NAC agar. United States Pharmacopeia Chapter <62> further enumerates testing procedures for specified objectionable microorganisms.

In certain embodiments, any controlled release formulation described herein has less than about 60 colony forming units (CFU), less than about 50 colony forming units, less than about 40 colony forming units, or less than about 30 colony forming units of microbial agents per gram of formulation. In certain embodiments, the otic fomulations described herein are formulated to be isotonic with the endolymph and/or the perilymph.

Endotoxins

Provided herein are otic compositions that ameliorate or lessen otic disorders described herein. Further provided herein are methods comprising the administration of said otic compositions. In some embodiments, the compositions or devices are substantially free of endotoxins. An additional aspect of the sterilization process is the removal of by-products from the killing of microorganisms (hereinafter, "Product"). The process of depyrogenation removes pyrogens from the sample. Pyrogens are endotoxins or exotoxins which induce an immune response. An example of an endotoxin is the lipopolysaccharide (LPS) molecule found in the cell wall of gram-negative bacteria. While sterilization procedures such as autoclaving or treatment with ethylene oxide kill the bacteria, the LPS residue induces a proinflammatory immune response, such as septic shock. Because the molecular size of endotoxins can vary widely, the presence of endotoxins is expressed in "endotoxin units" (EU). One EU is equivalent to 100 picograms of *E. coli* LPS. Humans can develop a response to as little as 5 EU/kg of body weight. The bioburden (e.g., microbial limit) and/or sterility (e.g., endotoxin level) is expressed in any units as recognized in the art. In certain embodiments, otic compositions described herein contain lower endotoxin levels (e.g. <4 EU/kg of body weight of a subject) when compared to conventionally acceptable endotoxin levels (e.g., 5 EU/kg of body weight of a subject). In some embodiments, the auris-acceptable otic therapeutic agent formulation has less than about 5 EU/kg of body weight of a subject. In other embodiments, the auris-acceptable otic therapeutic agent formulation has less than about 4 EU/kg of body weight of a subject. In additional embodiments, the auris-acceptable otic therapeutic agent formulation has less than about 3 EU/kg of body weight of a subject. In additional embodiments, the auris-acceptable otic therapeutic agent formulation has less than about 2 EU/kg of body weight of a subject.

In some embodiments, the auris-acceptable otic therapeutic agent formulation or device has less than about 5 EU/kg of formulation. In other embodiments, the auris-acceptable otic therapeutic agent formulation has less than about 4 EU/kg of formulation. In additional embodiments, the auris-acceptable otic therapeutic agent formulation has less than about 3 EU/kg of formulation. In some embodiments, the auris-acceptable otic therapeutic agent formulation has less than about 5 EU/kg Product. In other embodiments, the auris-acceptable otic therapeutic agent formulation has less than about 1 EU/kg Product. In additional embodiments, the auris-acceptable otic therapeutic agent formulation has less than about 0.2 EU/kg Product. In some embodiments, the auris-acceptable otic therapeutic agent formulation has less than about 5 EU/g of unit or Product. In other embodiments, the auris-acceptable otic therapeutic agent formulation has less than about 4 EU/g of unit or Product. In additional embodiments, the auris-acceptable otic therapeutic agent formulation has less than about 3 EU/g of unit or Product. In some embodiments, the auris-acceptable otic therapeutic agent formulation has less than about 5 EU/mg of unit or Product. In other embodiments, the auris-acceptable otic therapeutic agent formulation has less than about 4 EU/mg of unit or Product. In additional embodiments, the auris-acceptable otic therapeutic agent formulation has less than about 3 EU/mg of unit or Product. In certain embodiments, otic compositions described herein contain from about 1 to about 5 EU/mL of formulation. In certain embodiments, otic compositions described herein contain from about 2 to about 5 EU/mL of formulation, from about 3 to about 5 EU/mL of formulation, or from about 4 to about 5 EU/mL of formulation.

In certain embodiments, otic compositions or devices described herein contain lower endotoxin levels (e.g. <0.5 EU/mL of formulation) when compared to conventionally acceptable endotoxin levels (e.g., 0.5 EU/mL of formulation). In some embodiments, the auris-acceptable otic therapeutic agent formulation or device has less than about 0.5 EU/mL of formulation. In other embodiments, the auris-acceptable otic therapeutic agent formulation has less than about 0.4 EU/mL of formulation. In additional embodiments, the auris-acceptable otic therapeutic agent formulation has less than about 0.2 EU/mL of formulation.

Pyrogen detection, by way of example only, is performed by several methods. Suitable tests for sterility include tests described in United States Pharmacopoeia (USP)<71> Sterility Tests (23rd edition, 1995). The rabbit pyrogen test and the *Limulus amebocyte* lysate test are both specified in the United States Pharmacopeia Chapters <85> and <151> (USP23/NF 18, Biological Tests, The United States Pharmacopeial Convention, Rockville, Md., 1995). Alternative pyrogen assays have been developed based upon the monocyte activation-cytokine assay. Uniform cell lines suitable for quality control applications have been developed and have demonstrated the ability to detect pyrogenicity in samples that have passed the rabbit pyrogen test and the *Limulus amebocyte* lysate test (Taktak et al, J. Pharm. Pharmacol. (1990), 43:578-82). In an additional embodiment, the auris-acceptable otic therapeutic agent formulation is subject to depyrogenation. In a further embodiment, the process for the manufacture of the auris-acceptable otic therapeutic agent formulation comprises testing the formulation for pyrogenicity. In certain embodiments, the formulations described herein are substantially free of pyrogens.

pH and Practical Osmolarity

As used herein, "practical osmolarity" means the osmolarity of a formulation that is measured by including the active agent and all excipients except the gelling and/or the thickening agent (e.g., polyoxyethylene-polyooxypropylene copolymers, carboxymethylcellulose or the like). The practical osmolarity of a formulation described herein is measured by any suitable method, e.g., a freezing point depression method as described in Viegas et. al., *Int. J. Pharm.*, 1998, 160, 157-162. In some instances, the practical osmolarity of a composition described herein is measured by vapor pressure osmometry (e.g., vapor pressure depresssion method) that allows for determination of the osmolarity of a composition at higher temperatures. In some instances, vapor pressure depression method allows for determination of the osmolarity of a formulation comprising a gelling agent (e.g., a thermoreversible polymer) at a highter temperature wherein the gelling agent is in the form of a gel. The practical osmolality of an otic formulation described herein is from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L.

In some embodiments, the osmolarity at a target site of action (e.g., the perilymph) is about the same as the delivered osmolarity (i.e., osmolarity of materials that cross or penetrate the round window membrane) of any formulation described herein. In some embodiments, the formulations described herein have a delieverable osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L.

The main cation present in the endolymph is potassium. In addition the endolymph has a high concentration of positively charged amino acids. The main cation present in the perilymph is sodium. In certain instances, the ionic composition of the endolymph and perilymph regulate the electrochemical impulses of hair cells. In certain instances, any change in the ionic balance of the endolymph or perilymph results in a loss of hearing due to changes in the conduction of electrochemical impulses along otic hair cells. In some embodiments, a composition disclosed herein does not disrupt the ionic balance of the perilymph. In some embodiments, a composition disclosed herein has an ionic balance that is the same as or substantially the same as the perilymph. In some embodiments, a composition disclosed herein does not disrupt the ionic balance of the endolymph. In some embodiments, a composition disclosed herein has an ionic balance that is the same as or substantially the same as the endolymph. In some embodiments, an otic formulation described herein is formulated to provide an ionic balance that is compatible with inner ear fluids (e.g., endolymph and/or perilymph).

The endolymph and the perilymph have a pH that is close to the physiological pH of blood. The endolymph has a pH range of about 7.2-7.9; the perilymph has a pH range of about 7.2-7.4. The in situ pH of the proximal endolymph is about 7.4 while the pH of distal endolymph is about 7.9.

In some embodiments, the pH of a composition described herein is adjusted (e.g., by use of a buffer) to an endolymph-compatible pH range of about 5.5 to 9.0. In specific embodiments, the pH of a composition described herein is adjusted to a perilymph-suitable pH range of about 5.5 to about 9.0. In some embodiments, the pH of a composition described herein is adjusted to a perilymph-suitable range of about 5.5 to about 8.0, about 6 to about 8.0 or about 6.6 to about 8.0. In some embodiments, the pH of a composition described herein is adjusted to a perilymph-suitable pH range of about 7.0-7.6.

In some embodiments, useful formulations also include one or more pH adjusting agents or buffering agents. Suitable pH adjusting agents or buffers include, but are not limited to acetate, bicarbonate, ammonium chloride, citrate, phosphate, pharmaceutically acceptable salts thereof and combinations or mixtures thereof.

In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the body's natural buffering system.

In one embodiment, diluents are also used to stabilize compounds because they can provide a more stable environment. Salts dissolved in buffered solutions (which also can provide pH control or maintenance) are utilized as diluents in the art, including, but not limited to a phosphate buffered saline solution.

In some embodiments, any gel formulation described herein has a pH that allows for sterilization (e.g, by filtration or aseptic mixing or heat treatment and/or autoclaving (e.g., terminal sterilization) of a gel formulation without degradation of the pharmaceutical agent (e.g., aural pressure modulating agent) or the polymers comprising the gel. In order to reduce hydrolysis and/or degradation of the otic agent and/or the gel polymer during sterilization, the buffer pH is designed to maintain pH of the formulation in the 7-8 range during the process of sterilization (e.g., high temperature autoclaving).

In specific embodiments, any gel formulation described herein has a pH that allows for terminal sterilization (e.g, by heat treatment and/or autoclaving) of a gel formulation without degradation of the pharmaceutical agent (e.g., aural pressure modulating agent) or the polymers comprising the gel. For example, in order to reduce hydrolysis and/or degradation of the otic agent and/or the gel polymer during autoclaving, the buffer pH is designed to maintain pH of the formulation in the 7-8 range at elevated temperatures. Any appropriate buffer is used depending on the otic agent used in the formulation. In some instances, since $pK_a$ of TRIS decreases as temperature increases at approximately $-0.03/°$ C. and $pK_a$ of PBS increases as temperature increases at approximately $0.0031°$ C., autoclaving at $250°$ F. ($121°$ C.) results in a significant downward pH shift (i.e. more acidic) in the TRIS buffer whereas a relatively much less upward pH shift in the PBS buffer and therefore much increased hydrolysis and/or degradation of an otic agent in TRIS than in PBS. Degradation of an otic agent is reduced by the use of an appropriate combination of a buffer and polymeric additives (e.g. CMC) as described herein.

In some embodiments, a formulation pH of between about 5.0 and about 9.0, between about 5.5 and about 8.5, between about 6.0 and about 7.6, between about 7 and about 7.8, between about 7.0 and about 7.6, between about 7.2 and 7.6, or between about 7.2 and about 7.4 is suitable for sterilization (e.g, by filtration or aseptic mixing or heat treatment and/or autoclaving (e.g., terminal sterilization)) of auris formulations described herein. In specific embodiments a formulation pH of about 6.0, about 6.5, about 7.0, about 7.1, about 7.2, about 7.3, about 7.4, about 7.5, or about 7.6 is suitable for sterilization (e.g, by filtration or aseptic mixing or heat treatment and/or autoclaving (e.g., terminal sterilization)) of any composition descibed herein.

In some embodiments, the formulations have a pH as described herein, and include a thickening agent (e.g, a vicosity enhancing agent) such as, by way of non-limiting example, a cellulose based thickening agent described herein. In some instances, the addition of a secondary polymer (e.g., a thickening agent) and a pH of formulation as described herein, allows for sterilization of a formulation described herein without any substantial degradation of the otic agent and/or the polymer components in the otic formulation. In some embodiments, the ratio of a thermoreversible poloxamer to a thickening agent in a formulation that has a pH as described herein, is about 40:1, about 35:1, about 30:1, about 25:1, about 20:1, about 15:1 about 10:1, or about 5:1. For example, in certain embodiments, a sustained and/or extended release formulation described herein comprises a combination of poloxamer 407 (pluronic F127) and carboxymethylcellulose (CMC) in a ratio of about 40:1, about 35:1, about 30:1, about 25:1, about 20:1, about 15:1, about 10:1 or about 5:1.

In some embodiments, the amount of thermoreversible polymer in any formulation described herein is about 10%, about 15%, about 20%, about 25%, about 30%, about 35% or about 40% of the total weight of the formulation. In some embodiments, the amount of thermoreversible polymer in any formulation described herein is about 10%, about 11%, about 12%, about 13%, about 14%, about 15%, about 16%, about 17%, about 18%, about 19%, about 20%, about 21%, about 22%, about 23%, about 24% or about 25% of the total weight of the formulation. In some embodiments, the amount of thermoreversible polymer (e.g., pluronic F127) in any formulation described herein is about 7.5% of the total weight of the formulation. In some embodiments, the amount of thermoreversible polymer (e.g., pluronic F127) in any formulation described herein is about 10% of the total weight of the formulation. In some embodiments, the amount of thermoreversible polymer (e.g., pluronic F127) in any formulation described herein is about 11% of the total weight of the formulation. In some embodiments, the amount of thermoreversible polymer (e.g., pluronic F127) in any formulation described herein is about 12% of the total weight of the formulation. In some embodiments, the amount of thermoreversible polymer (e.g., pluronic F127) in any formulation described herein is about 13% of the total weight of the formulation. In some embodiments, the amount of thermoreversible polymer (e.g., pluronic F127) in any formulation described herein is about 14% of the total weight of the formulation. In some embodiments, the amount of thermoreversible polymer (e.g., pluronic F127) in any formulation described herein is about 15% of the total weight of the formulation. In some embodiments, the amount of thermoreversible polymer (e.g., pluronic F127) in any formulation described herein is about 16% of the total weight of the formulation. In some embodiments, the amount of thermoreversible polymer (e.g., pluronic F127) in any formulation described herein is about 17% of the total weight of the formulation. In some embodiments, the amount of thermoreversible polymer (e.g., pluronic F127) in any formulation described herein is about 18% of the total weight of the formulation. In some embodiments, the amount of thermoreversible polymer (e.g., pluronic F127) in any formulation described herein is about 19% of the total weight of the formulation. In some embodiments, the amount of thermoreversible polymer (e.g., pluronic F127) in any formulation described herein is about 20% of the total weight of the formulation. In some embodiments, the amount of thermoreversible polymer (e.g., pluronic F127) in any formulation described herein is about 21% of the total weight of the formulation. In some embodiments, the amount of thermoreversible polymer (e.g., pluronic F127) in any formulation described herein is about 23% of the total weight of the formulation. In some embodiments, the amount of thermoreversible polymer (e.g., pluronic F127) in any formulation described herein is about 25% of the total weight of the formulation.

In some embodiments, the amount of thickening agent (e.g., a gelling agent) in any formulation described herein is about 1%, about 5%, about 10%, or about 15% of the total weight of the formulation. In some embodiments, the amount of thickening agent (e.g., a gelling agent) in any formulation described herein is about 0.5%, about 1%, about 1.5%, about 2%, about 2.5%, about 3%, about 3.5%, about 4%, about 4.5%, or about 5% of the total weight of the formulation.

In some embodiments, the pharmaceutical formulations described herein are stable with respect to pH over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 1 month, at least about 2 months, at least about 3 months, at least about 4 months, at least about 5 months, or at least about 6 months. In other embodiments, the formulations described herein are stable with respect to pH over a period of at least about 1 week. Also described herein are formulations that are stable with respect to pH over a period of at least about 1 month.

Tonicity Agents

In general, the endolymph has a higher osmolality than the perilymph. For example, the endolymph has an osmolality of about 304 mOsm/kg $H_2O$ while the perilymph has an osmolality of about 294 mOsm/kg $H_2O$. In certain embodiments, tonicity agents are added to the formulations described herein in an amount as to provide a practical osmolality of an otic formulation of about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 350 mOsm/kg or from about 280 mOsm/kg to about 320 mOsm/kg. In some embodiments, the formulations described herein have a practical osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 280 mOsm/L to about 320 mOsm/L or about 250 mOsm/L to about 320 mOsm/L.

In some embodiments, the deliverable osmolarity of any formulation described herein is designed to be isotonic with the targeted otic structure (e.g., endolymph, perilymph or the like). In specific embodiments, auris compositions described herein are formulated to provide a delivered perilymph-suitable osmolarity at the target site of action of about 250 to about 320 mOsm/L; and preferably about 270 to about 320 mOsm/L. In specific embodiments, auris compositions described herein are formulated to provide a delivered perilymph-suitable osmolality at the target site of action of about 250 to about 320 mOsm/kg $H_2O$; or an osmolality of about 270 to about 320 mOsm/kg $H_2O$. In specific embodiments, the deliverable osmolarity/osmolality of the formulations (i.e., the osmolarity/osmolality of the formulation in the absence of gelling or thickening agents (e.g., thermoreversible gel polymers) is adjusted, for example, by the use of appropriate salt concentrations (e.g., concentration of potassium or sodium salts) or the use of tonicity agents which renders the formulations endolymph-compatible and/or perilymph-compatible (i.e. isotonic with the endolymph and/or perilymph) upon delivery at the target site. The osmolarity of a formulation comprising a thermoreversible gel polymer is an unreliable measure due to the association of varying amounts of water with the monomeric units of the polymer. The practical osmolarity of a formulation (i.e., osmolarity in the absence of a gelling or thickening agent (e.g. a thermoreversible gel polymer) is a reliable measure and is measured by any suitable method (e.g., freezing point depression method, vapor depression method). In some instances, the formulations described herein provide a deliverable osmolarity (e.g., at a target site (e.g., perilymph) that causes minimal disturbance to the environment of the inner ear and causes minimum discomfort (e.g., vertigo and/or nausea) to a mammal upon administration.

In some embodiments, any formulation described herein is isotonic with the perilymph and/or endolymph. Isotonic formulations are provided by the addition of a tonicity agent. Suitable tonicity agents include, but are not limited to any pharmaceutically acceptable sugar, salt or any combinations or mixtures thereof, such as, but not limited to dextrose, glycerin, mannitol, sorbitol, sodium chloride, and other electrolytes.

Useful auris compositions include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the formulations described herein have a pH and/or practical osmolarity as described herein, and have a concentration of active pharmaceutical ingredient between about 1 µM and about 10 µM, between about 1 mM and about 100 mM, between about 0.1 mM and about 100 mM, between about 0.1 mM and about 100 nM. In some embodiments, the formulations described herein have a pH and/or practical osmolarity as described herein, and have a concentration of active pharmaceutical ingredient between about 0.01%-about 20%, between about 0.01%-about 10%, between about 0.01%-about 7.5%, between about 0.01%-6%, between about 0.01-5%, between about 0.1-about 10%, or between about 0.1-about 6% of the active ingredient by weight of the formulation. In some embodiments, the formulations described herein have a pH and/or practical osmolarity as described herein, and have a concentration of active pharmaceutical ingredient between about 0.1 and about 70 mg, between about 1 mg and about 70 mg/mL, between about 1 mg and about 50 mg/mL, between about 1 mg/mL and about 20 mg/mL, between about 1 mg/mL to about 10 mg/mL, between about 1 mg/mL to about 5 mg/mL, or between about 0.5 mg/mL to about 5 mg/mL of the active agent by volume of the formulation. In some embodiments, the formulations described herein have a pH and/or practical osmolarity as described herein, and have a concentration of active pharmaceutical ingredient between about 1 µg/mL and about 500 mg/mL, between about 1 µg/mL and about 250 µg/mL, between about 1 mg and about 100 µg/mL, between about 1 µg/mL and about 50 µg/mL, or between about 1 µg/mL and about 20 µg/mL of the active agent by volume of the formulation.

Particle Size

Size reduction is used to increase surface area and/or modulate formulation dissolution properties. It is also used to maintain a consistent average particle size distribution (PSD) (e.g., micrometer-sized particles, nanometer-sized particles or the like) for any formulation described herein. In some embodiments, any formulation described herein comprises multiparticulates, i.e., a plurality of particle sizes (e.g., micronized particles, nano-sized particles, non-sized particles, colloidal particles); i.e, the formulation is a multiparticulate formulation. In some embodiments, any formulation described herein comprises one or more multiparticulate (e.g., micronized) therapeutic agents. Micronization is a process of reducing the average diameter of particles of a solid material. Micronized particles are from about micrometer-sized in diameter to about nanometer-sized in diameter. In some embodiments, the average diameter of particles in a micronized solid is from about 0.5 µm to about 500 µm. In some embodiments, the average diameter of particles in a micronized solid is from about 1 µm to about 200 µm. In some embodiments, the average diameter of particles in a micronized solid is from about 2 μm to about 100 μm. In some embodiments, the average diameter of particles in a micronized solid is from about 3 μm to about 50 μm. In some embodiments, a particulate micronized solid comprises particle sizes of less than about 5 microns, less than about 20 microns and/or less than about 100 microns. In some embodiments, the use of particulates (e.g., micronized particles) of aural pressure modulating agent allows for extended and/or sustained release of the aural pressure modulating agent from any formulation described herein compared to a formulation comprising non-multiparticulate (e.g, non-micronized) aural pressure modulating agent. In some instances, formulations containing multiparticulate (e.g. micronized) aural pressure modulating agent are ejected from a 1 mL syringe adapted with a 27G needle without any plugging or clogging.

In some instances, any particle in any formulation described herein is a coated particle (e.g., a coated micronized particle, nano-particle) and/or a microsphere and/or a liposomal particle. Particle size reduction techniques include, by way of example, grinding, milling (e.g., air-attrition milling (jet milling), ball milling), coacervation, complex coacervation, high pressure homogenization, spray drying and/or supercritical fluid crystallization. In some instances, particles are sized by mechanical impact (e.g., by hammer mills, ball mill and/or pin mills). In some instances, particles are sized via fluid energy (e.g., by spiral jet mills, loop jet mills, and/or fluidized bed jet mills). In some embodiments formulations described herein comprise crystalline particles and/or isotropic particles. In some embodiments, formulations described herein comprise amorphous particles and/or anisotropic particles. In some embodiments, formulations described herein comprise therapeutic agent particles wherein the therapeutic agent is a free base, or a salt, or a prodrug of a therapeutic agent, or any combination thereof.

In some embodiments, a formulation described herein comprises one or more aural pressure modulating agents wherein the aural pressure modulating agent comprises nanoparticulates. In some embodiments, a formulation described herein comprises aural pressure modulating agent beads (e.g., conivaptan beads) that are optionally coated with controlled release excipients. In some embodiments, a formulation described herein comprises a aural pressure modulating agent that is granulated and/or reduced in size and coated with controlled release excipients; the granulated coated aural pressure modulating agent particulates are then optionally micronized and/or formulated in any of the compositions described herein.

In some instances, a combination of an aural pressure modulating agent as a neutral molecule, free acid or free base and a salt of the aural pressure modulating agent is used to prepare pulsed release otic agent formulations using the procedures described herein. In some formulations, a combination of a micronized aural pressure modulating agent (and/or salt or prodrug thereof) and coated particles (e.g., nanoparticles, liposomes, microspheres) is used to prepare pulsed release otic agent formulations using any procedure described herein. Alternatively, a pulsed release profile is achieved by solubilizing up to 20% of the delivered dose of the aural pressure modulating agent (e.g., micronized aural pressure modulating agent, free base, free acid or salt or prodrug thereof multiparticulate aural pressure modulating agent, free base, free acid or salt or prodrug thereof) with the aid of cyclodextrins, surfactants (e.g., poloxamers (407, 338, 188), tween (80, 60, 20, 81), PEG-hydrogenated castor oil, cosolvents like N-methyl-2-Pyrrolidone or the like and preparing pulsed release formulations using any procedure described herein.

In specific embodiments, any auris-compatible formulation described herein comprises one or more micronized pharmaceutical agents (e.g., aural pressure modulating agents). In some of such embodiments, a micronized pharmaceutical agent comprises micronized particles, coated (e.g., with an extended release coat) micronized particles, or a combination thereof. In some of such embodiments, a micronized pharmaceutical agent comprising micronized particles, coated micronized particles, or a combination thereof, comprises an aural pressure modulating agent as a neutral molecule, a free acid, a free base, a salt, a prodrug or any combination thereof. In certain embodiments, a pharmaceutical composition described herein comprises an aural pressure modulating agent as a micronized powder. In certain embodiments, a pharmaceutical composition described herein comprises an aural pressure modulating agent in the form of a micro-aural pressure modulating agent powder.

The multiparticulates and/or micronized aural pressure modulating agents described herein are delivered to an auris structure (e.g., inner ear) by means of any type of matrix including solid, liquid or gel matrices. In some embodiments, the multiparticulates and/or micronized aural pressure modulating agents described herein are delivered to an auris structure (e.g., inner ear) by means of any type of matrix including solid, liquid or gel matrices via intratympanic injection.

Pharmaceutical Formulations

Provided herein are pharmaceutical compositions or devices that include at least one aural pressure modulating agent and a pharmaceutically acceptable diluent(s), excipient(s), or carrier(s). In some embodiments, the pharmaceutical compositions include other medicinal or pharmaceutical agents, carriers, adjuvants, such as preserving, stabilizing, wetting or emulsifying agents, solution promoters, salts for regulating the osmotic pressure, and/or buffers. In other embodiments, the pharmaceutical compositions also contain other therapeutic substances.

In some embodiments, the compositions or devices described herein include a dye to help enhance the visualization of the gel when applied. In some embodiments, dyes that are compatible with the auris-acceptable compositions or devices described herein include Evans blue (e.g., 0.5% of the total weight of an otic formulation), Methylene blue (e.g., 1% of the total weight of an otic formulation), Isosulfan blue (e.g., 1% of the total weight of an otic formulation), Trypan blue (e.g., 0.15% of the total weight of an otic formulation), and/or indocyanine green (e.g., 25 mg/vial). Other common dyes, e.g, FD&C red 40, FD&C red 3, FD&C yellow 5, FD&C yellow 6, FD&C blue 1, FD&C blue2, FD&C green 3, fluorescence dyes (e.g., Fluorescein isothiocyanate, rhodamine, Alexa Fluors, DyLight Fluors) and/or dyes that are visualizable in conjunction with non-invasive imaging techniques such as MRI, CAT scans, PET scans or the like. Gadolinium-based MRI dyes, iodine-base dyes, barium-based dyes or the like are also contemplated for use with any otic formulation described herein. Other dyes that are compatible with any formulation or composition described herein are listed in the Sigma-Aldrich catalog under dyes (which is included herein by reference for such disclosure).

Any pharmaceutical composition or device described herein is administered by locating the composition or device in contact with the crista fenestrae cochlea, the round window, the tympanic cavity, the tympanic membrane, the auris media or the auris externa.

In one specific embodiment of the auris-acceptable controlled release aural pressure modulating agent pharmaceutical formulations described herein, the aural pressure modulating agent is provided in a gel matrix, also referred to herein as "auris acceptable gel formulations," "auris interna-acceptable gel formulations," "auris media-acceptable gel formulations," "auris externa-acceptable gel formulations", "auris gel formulations" or variations thereof. All of the other components of the gel formulation must be compatible with the targeted auris structure. Further, the gel formulations provide controlled release of the aural pressure modulating agent to the desired site within the targeted auris structure; in some embodiments, the gel formulation also has an immediate or rapid release component for delivery of the aural pressure modulating agent to the desired target site. In other embodiments, the gel formulation has a sustained release component for delivery of the aural pressure modulating agent. In some embodiments, the gel formulation comprises a multiparticulate (e.g., micronized) aural pressure modulating agent. In some embodiments, the auris gel formulations are biodegradeable. In other embodiments, the auris gel formulations include a mucoadhesive excipient to allow adhesion to the external mucous layer of the round window membrane. In yet other embodiments, the auris gel formulations include a penetration enhancer excipient; in further embodiments, the auris gel formulation contains a viscosity enhancing agent sufficient to provide a viscosity of between about 500 and 1,000,000 centipoise, between about 750 and 1,000,000 centipoise; between about 1000 and 1,000,000 centipoise; between about 1000 and 400,000 centipoise; between about 2000 and 100,000 centipoise; between about 3000 and 50,000 centipoise; between about 4000 and 25,000 centipoise; between about 5000 and 20,000 centipoise; or between about 6000 and 15,000 centipoise. In some embodiments, the auris gel formulation contains a viscosity enhancing agent sufficient to provide a viscosity of between about 50,0000 and 1,000,000 centipoise.

In other embodiments, the auris interna pharmaceutical formulations described herein further provide an auris-acceptable hydrogel; in yet other embodiments, the auris pharmaceutical formulations provide an auris-acceptable microsphere or microparticle; in still other embodiments, the auris pharmaceutical formulations provide an auris-acceptable liposome. In some embodiments, the auris pharmaceutical formulations provide an auris-acceptable foam; in yet other embodiments, the auris pharmaceutical formulations provide an auris-acceptable paint; in still further embodiments, the auris pharmaceutical formulations provide an auris-acceptable in situ forming spongy material. In some embodiments, the auris pharmaceutical formulations provide an auris-acceptable solvent release gel. In some embodiments, the auris pharmaceutical formulations provide an actinic radiation curable gel. Further embodiments include a thermoreversible gel in the auris pharmaceutical formulation, such that upon preparation of the gel at room temperature or below, the formulation is a fluid, but upon application of the gel into or near the auris interna and/or auris media target site, including the tympanic cavity, round window membrane or the crista fenestrae cochleae, the auris-pharmaceutical formulation stiffens or hardens into a gel-like substance.

In further or alternative embodiments, the auris gel formulations are capable of being administered on or near the round window membrane via intratympanic injection. In other embodiments, the auris gel formulations are administered on or near the round window or the crista fenestrae cochleae through entry via a post-auricular incision and surgical manipulation into or near the round window or the crista fenestrae cochleae area. Alternatively, the auris gel formulation is applied via syringe and needle, wherein the needle is inserted through the tympanic membrane and guided to the area of the round window or crista fenestrae cochleae. The auris gel formulations are then deposited on or near the round window or crista fenestrae cochleae for localized treatment of autoimmune otic disorders. In other embodiments, the auris gel formulations are applied via microcathethers implanted into the patient, and in yet further embodiments the formulations are administered via a pump device onto or near the round window membrane. In still further embodiments, the auris gel formulations are applied at or near the round window membrane via a microinjection device. In yet other embodiments, the auris gel formulations are applied in the tympanic cavity. In some embodiments, the auris gel formulations are applied on the tympanic membrane. In still other embodiments, the auris gel formulations are applied onto or in the auditory canal.

In further specific embodiments, any pharmaceutical composition or device described herein comprises a multiparticulate aural pressure modulating agentin a liquid matrix (e.g., a liquid composition for intratympanic injection, or otic drops). In certain embodiments, any pharmaceutical composition described herein comprises a multiparticulate aural pressure modulating agentin a solid matrix.

Controlled Release Formulations

In general, controlled release drug formulations impart control over the release of drug with respect to site of release and time of release within the body. As discussed herein, controlled release refers to immediate release, delayed release, sustained release, extended release, variable release, pulsatile release and bi-modal release. Many advantages are offered by controlled release. First, controlled release of a pharmaceutical agent allows less frequent dosing and thus minimizes repeated treatment. Second, controlled release treatment results in more efficient drug utilization and less of the compound remains as a residue. Third, controlled release offers the possibility of localized drug delivery by placement of a delivery device or formulation at the site of disease. Still further, controlled release offers the opportunity to administer and release two or more different drugs, each having a unique release profile, or to release the same drug at different rates or for different durations, by means of a single dosage unit.

Accordingly, one aspect of the embodiments disclosed herein is to provide a controlled release aural pressure modulating agent auris-acceptable composition or device for the treatment of autoimmune disorders and/or inflammatory disorders. The controlled release aspect of the compositions and/or formulations and/or devices disclosed herein is imparted through a variety of agents, including but not limited to excipients, agents or materials that are acceptable for use in the auris interna or other otic structure. By way of example only, such excipients, agents or materials include an auris-acceptable polymer, an auris-acceptable viscosity enhancing agent, an auris-acceptable gel, an auris-acceptable paint, an auris-acceptable foam, an auris-acceptable xerogel, an auris-acceptable microsphere or microparticle, an auris-acceptable hydrogel, an auris-acceptable in situ forming spongy material, an auris-acceptable actinic radiation curable gel, an auris-acceptable solvent release gel, an auris-acceptable liposome, an auris-acceptable nanocapsule or nanosphere, an auris-acceptable thermoreversible gel, or combinations thereof.

Auris-Acceptable Gels

Gels, sometimes referred to as jellies, have been defined in various ways. For example, the United States Pharmacopoeia defines gels as semisolid systems consisting of either suspensions made up of small inorganic particles or large organic molecules interpenetrated by a liquid. Gels include a single-phase or a two-phase system. A single-phase gel consists of organic macromolecules distributed uniformly throughout a liquid in such a manner that no apparent boundaries exist between the dispersed macromolecules and the liquid. Some single-phase gels are prepared from synthetic macromolecules (e.g., carbomer) or from natural gums, (e.g., tragacanth). In some embodiments, single-phase gels are generally aqueous, but will also be made using alcohols and oils. Two-phase gels consist of a network of small discrete particles.

Gels can also be classified as being hydrophobic or hydrophilic. In certain embodiments, the base of a hydrophobic gel consists of a liquid paraffin with polyethylene or fatty oils gelled with colloidal silica, or aluminum or zinc soaps. In contrast, the base of hydrophobic gels usually consists of water, glycerol, or propylene glycol gelled with a suitable gelling agent (e.g., tragacanth, starch, cellulose derivatives, carboxyvinylpolymers, and magnesium-aluminum silicates). In certain embodiments, the rheology of the compositions or devices disclosed herein is pseudo plastic, plastic, thixotropic, or dilatant.

In one embodiment the enhanced viscosity auris-acceptable formulation described herein is not a liquid at room temperature. In certain embodiments, the enhanced viscosity formulation is characterized by a phase transition between room temperature and body temperature (including an individual with a serious fever, e.g., up to about 42° C.). In some embodiments, the phase transition occurs at 1° C. below body temperature, at 2° C. below body temperature, at 3° C. below body temperature, at 4° C. below body temperature, at 6° C. below body temperature, at 8° C. below body temperature, or at 10° C. below body temperature. In some embodiments, the phase transition occurs at about 15° C. below body temperature, at about 20° C. below body temperature or at about 25° C. below body temperature. In specific embodiments, the gelation temperature (Tgel) of a formulation described herein is about 20° C., about 25° C., or about 30° C. In certain embodiments, the gelation temperature (Tgel) of a formulation described herein is about 35° C., or about 40° C. In one embodiment, administration of any formulation described herein at about body temperature reduces or inhibits vertigo associated with intratympanic administration of otic formulations. Included within the definition of body temperature is the body temperature of a healthy individual, or an unhealthy individual, including an individual with a fever (up to ~42° C.). In some embodiments, the pharmaceutical compositions or devices described herein are liquids at about room temperature and are administered at or about room temperature, reducing or ameliorating side effects such as, for example, vertigo.

Polymers composed of polyoxypropylene and polyoxyethylene form thermoreversible gels when incorporated into aqueous solutions. These polymers have the ability to change from the liquid state to the gel state at temperatures close to body temperature, therefore allowing useful formulations that are applied to the targeted auris structure(s). The liquid state-to-gel state phase transition is dependent on the polymer concentration and the ingredients in the solution.

Poloxamer 407 (PF-127) is a nonionic surfactant composed of polyoxyethylene-polyoxypropylene copolymers. Other poloxamers include 188 (F-68 grade), 237 (F-87 grade), 338 (F-108 grade). Aqueous solutions of poloxamers are stable in the presence of acids, alkalis, and metal ions. PF-127 is a commercially available polyoxyethylene-polyoxypropylene triblock copolymer of general formula E106 P70 E106, with an average molar mass of 13,000. The polymer can be further purified by suitable methods that will enhance gelation properties of the polymer. It contains approximately 70% ethylene oxide, which accounts for its hydrophilicity. It is one of the series of poloxamer ABA block copolymers, whose members share the chemical formula shown below.

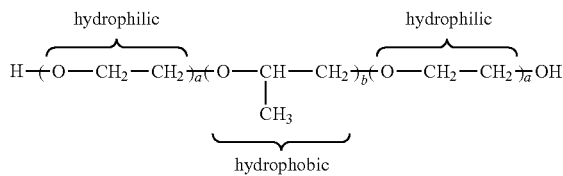

PF-127 is of particular interest since concentrated solutions (>20% w/w) of the copolymer are transformed from low viscosity transparent solutions to solid gels on heating to body temperature. This phenomenon, therefore, suggests that when placed in contact with the body, the gel preparation will form a semi-solid structure and a sustained release depot. Furthermore, PF-127 has good solubilizing capacity, low toxicity and is, therefore, considered a good medium for drug delivery systems.

In an alternative embodiment, the thermogel is a PEG-PLGA-PEG triblock copolymer (Jeong et al, Nature (1997), 388:860-2; Jeong et al, J. Control. Release (2000), 63:155-63; Jeong et al, Adv. Drug Delivery Rev. (2002), 54:37-51). The polymer exhibits sol-gel behavior over a concentration of about 5% w/w to about 40% w/w. Depending on the properties desired, the lactide/glycolide molar ratio in the PLGA copolymer ranges from about 1:1 to about 20:1. The resulting copolymers are soluble in water and form a free-flowing liquid at room temperature, but form a hydrogel at body temperature. A commercially available PEG-PLGA-PEG triblock copolymer is RESOMER RGP t50106 manufactured by Boehringer Ingelheim. This material is composed of a PGLA copolymer of 50:50 poly(DL-lactide-co-glycolide) and is 10% w/w of PEG and has a molecular weight of about 6000.

ReGel® is a tradename of MacroMed Incorporated for a class of low molecular weight, biodegradable block copolymers having reverse thermal gelation properties as described in U.S. Pat. Nos. 6,004,573, 6,117,949, 6,201,072, and 6,287,588. It also includes biodegradable polymeric drug carriers disclosed in pending U.S. patent application Ser. Nos. 09/906,041, 09/559,799 and 10/919,603. The biodegradable drug carrier comprises ABA-type or BAB-type triblock copolymers or mixtures thereof, wherein the A-blocks are relatively hydrophobic and comprise biodegradable polyesters or poly(orthoester)s, and the B-blocks are relatively hydrophilic and comprise polyethylene glycol (PEG), said copolymers having a hydrophobic content of between 50.1 to 83% by weight and a hydrophilic content of between 17 to 49.9% by weight, and an overall block copolymer molecular weight of between 2000 and 8000 Daltons. The drug carriers exhibit water solubility at temperatures below normal mammalian body temperatures and undergo reversible thermal gelation to then exist as a gel at temperatures equal to physiological mammalian body temperatures. The biodegradable, hydrophobic A polymer block comprises a polyester or poly(ortho ester), in which the polyester is synthesized from monomers selected from the group consisting of D,L-lactide, D-lactide, L-lactide, D,L-lactic acid, D-lactic acid, L-lactic acid, glycolide, glycolic acid, ε-caprolactone, ε-hydroxyhexanoic acid, γ-butyrolactone, γ-hydroxybutyric acid, δ-valerolactone, δ-hydroxyvaleric acid, hydroxybutyric acids, malic acid, and copolymers thereof and having an average molecular weight of between about 600 and 3000 Daltons. The hydrophilic B-block segment is preferably polyethylene glycol (PEG) having an average molecular weight of between about 500 and 2200 Daltons.

Additional biodegradable thermoplastic polyesters include AtriGel® (provided by Atrix Laboratories, Inc.) and/or those disclosed, e.g., in U.S. Pat. Nos. 5,324,519; 4,938,763; 5,702,716; 5,744,153; and 5,990,194; wherein the suitable biodegradable thermoplastic polyester is disclosed as a thermoplastic polymer. Examples of suitable biodegradable thermoplastic polyesters include polylactides, polyglycolides, polycaprolactones, copolymers thereof, terpolymers thereof, and any combinations thereof. In some such embodiments, the suitable biodegradable thermoplastic polyester is a polylactide, a polyglycolide, a copolymer thereof, a terpolymer thereof, or a combination thereof. In one embodiment, the biodegradable thermoplastic polyester is 50/50 poly(DL-lactide-co-glycolide) having a carboxy terminal group; is present in about 30 wt. % to about 40 wt. % of the composition; and has an average molecular weight of about 23,000 to about 45,000. Alternatively, in another embodiment, the biodegradable thermoplastic polyester is 75/25 poly (DL-lactide-co-glycolide) without a carboxy terminal group; is present in about 40 wt. % to about 50 wt. % of the composition; and has an average molecular weight of about 15,000 to about 24,000. In further or alternative embodiments, the terminal groups of the poly(DL-lactide-co-glycolide) are either hydroxyl, carboxyl, or ester depending upon the method of polymerization. Polycondensation of lactic or glycolic acid provides a polymer with terminal hydroxyl and carboxyl groups. Ring-opening polymerization of the cyclic lactide or glycolide monomers with water, lactic acid, or glycolic acid provides polymers with the same terminal groups. However, ring-opening of the cyclic monomers with a monofunctional alcohol such as methanol, ethanol, or 1-dodecanol provides a polymer with one hydroxyl group and one ester terminal groups. Ring-opening polymerization of the cyclic monomers with a diol such as 1,6-hexanediol or polyethylene glycol provides a polymer with only hydroxyl terminal groups.

Since the polymer systems of thermoreversible gels dissolve more completely at reduced temperatures, methods of solubilization include adding the required amount of polymer to the amount of water to be used at reduced temperatures. Generally after wetting the polymer by shaking, the mixture is capped and placed in a cold chamber or in a thermostatic container at about 0-10° C. in order to dissolve the polymer. The mixture is stirred or shaken to bring about a more rapid dissolution of the thermoreversible gel polymer. The aural pressure modulating agent and various additives such as buffers, salts, and preservatives are subsequently added and dissolved. In some instances the aural pressure modulating agent and/or other pharmaceutically active agent is suspended if it is insoluble in water. The pH is modulated by the addition of appropriate buffering agents. round window membrane mucoadhesive characteristics are optionally imparted to a thermoreversible gel by incorporation of round window membrane mucoadhesive carbomers, such as Carbopol® 934P, to the composition (Majithiya et al, AAPS PharmSciTech (2006), 7(3), p. E1; EP0551626, both of which is incorporated herein by reference for such disclosure).

In one embodiment are auris-acceptable pharmaceutical gel formulations which do not require the use of an added viscosity enhancing agent. Such gel formulations incorporate at least one pharmaceutically acceptable buffer. In one aspect is a gel formulation comprising an aural pressure modulating agent and a pharmaceutically acceptable buffer. In another embodiment, the pharmaceutically acceptable excipient or carrier is a gelling agent.

In other embodiments, useful aural pressure modulating agent auris-acceptable pharmaceutical formulations also include one or more pH adjusting agents or buffering agents to provide an endolymph or perilymph suitable pH. Suitable pH adjusting agents or buffers include, but are not limited to acetate, bicarbonate, ammonium chloride, citrate, phosphate, pharmaceutically acceptable salts thereof and combinations or mixtures thereof. Such pH adjusting agents and buffers are included in an amount required to maintain pH of the composition between a pH of about 5 and about 9, in one embodiment a pH between about 6.5 to about 7.5, and in yet another embodiment at a pH of about 6.5, 6.6, 6.7, 6.8, 6.9, 7.0, 7.1, 7.2, 7.3, 7.4, 7.5. In one embodiment, when one or more buffers are utilized in the formulations of the present disclosure, they are combined, e.g., with a pharmaceutically acceptable vehicle and are present in the final formulation, e.g., in an amount ranging from about 0.1% to about 20%, from about 0.5% to about 10%. In certain embodiments of the present disclosure, the amount of buffer included in the gel formulations are an amount such that the pH of the gel formulation does not interfere with the auris media or auris interna's natural buffering system, or does not interfere with the natural pH of the endolymph or perilymph: depending on where in the cochlea the aural pressure modulating agent formulation is targeted. In some embodiments, from about 10 μM to about 200 mM concentration of a buffer is present in the gel formulation. In certain embodiments, from about a 5 mM to about a 200 mM concentration of a buffer is present. In certain embodiments, from about a 20 mM to about a 100 mM concentration of a buffer is present. In one embodiment is a buffer such as acetate or citrate at slightly acidic pH. In one embodiment the buffer is a sodium acetate buffer having a pH of about 4.5 to about 6.5. In one embodiment the buffer is a sodium citrate buffer having a pH of about 5.0 to about 8.0, or about 5.5 to about 7.0.

In an alternative embodiment, the buffer used is tris (hydroxymethyl)aminomethane, bicarbonate, carbonate or phosphate at slightly basic pH. In one embodiment, the buffer is a sodium bicarbonate buffer having a pH of about 6.5 to about 8.5, or about 7.0 to about 8.0. In another embodiment the buffer is a sodium phosphate dibasic buffer having a pH of about 6.0 to about 9.0.

Also described herein are controlled release formulations or devices comprising a aural pressure modulating agent and a viscosity enhancing agent. Suitable viscosity-enhancing agents include by way of example only, gelling agents and suspending agents. In one embodiment, the enhanced viscosity formulation does not include a buffer. In other embodiments, the enhanced viscosity formulation includes a pharmaceutically acceptable buffer. Sodium chloride or other tonicity agents are optionally used to adjust tonicity, if necessary.

By way of example only, the auris-acceptable viscosity agent include hydroxypropyl methylcellulose, hydroxyethyl cellulose, polyvinylpyrrolidone, carboxymethyl cellulose, polyvinyl alcohol, sodium chondroitin sulfate, sodium hyaluronate. Other viscosity enhancing agents compatible with the targeted auris structure include, but are not limited to, acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly(methoxyethyl methacrylate), poly (methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose) or combinations thereof. In specific embodiments, the viscosity-enhancing excipient is a combination of MCC and CMC. In another embodiment, the viscosity-enhancing agent is a combination of carboxymethylated chitosan, or chitin, and alginate. The combination of chitin and alginate with the aural pressure modulating agents disclosed herein acts as a controlled release formulation, restricting the diffusion of the aural pressure modulating agents from the formulation. Moreover, the combination of carboxymethylated chitosan and alginate is optionally used to assist in increasing the permeability of the aural pressure modulating agents through the round window membrane.

In some embodiments is an enhanced viscosity formulation, comprising from about 0.1 mM and about 100 mM of a aural pressure modulating agent, a pharmaceutically acceptable viscosity agent, and water for injection, the concentration of the viscosity agent in the water being sufficient to provide a enhanced viscosity formulation with a final viscosity from about 100 to about 100,000 cP. In certain embodiments, the viscosity of the gel is in the range from about 100 to about 50,000 cP, about 100 cP to about 1,000 cP, about 500 cP to about 1500 cP, about 1000 cP to about 3000 cP, about 2000 cP to about 8,000 cP, about 4,000 cP to about 50,000 cP, about 10,000 cP to about 500,000 cP, about 15,000 cP to about 1,000,000 cP. In other embodiments, when an even more viscous medium is desired, the biocompatible gel comprises at least about 35%, at least about 45%, at least about 55%, at least about 65%, at least about 70%, at least about 75%, or even at least about 80% or so by weight of the aural pressure modulating agent. In highly concentrated samples, the biocompatible enhanced viscosity formulation comprises at least about 25%, at least about 35%, at least about 45%, at least about 55%, at least about 65%, at least about 75%, at least about 85%, at least about 90% or at least about 95% or more by weight of the aural pressure modulating agent.

In some embodiments, the viscosity of the gel formulations presented herein are measured by any means described. For example, in some embodiments, an LVDV-II+CP Cone Plate Viscometer and a Cone Spindle CPE-40 is used to calculate the viscosity of the gel formulation described herein. In other embodiments, a Brookfield (spindle and cup) viscometer is used to calculate the viscosity of the gel formulation described herein. In some embodiments, the viscosity ranges referred to herein are measured at room temperature. In other embodiments, the viscosity ranges referred to herein are measured at body temperature (e.g., at the average body temperature of a healthy human).

In one embodiment, the pharmaceutically acceptable enhanced viscosity auris-acceptable formulation comprises at least one aural pressure modulating agent and at least one gelling agent. Suitable gelling agents for use in preparation of the gel formulation include, but are not limited to, celluloses, cellulose derivatives, cellulose ethers (e.g., carboxymethylcellulose, ethylcellulose, hydroxyethylcellulose, hydroxymethylcellulose, hydroxypropylmethylcellulose, hydroxypropylcellulose, methylcellulose), guar gum, xanthan gum, locust bean gum, alginates (e.g., alginic acid), silicates, starch, tragacanth, carboxyvinyl polymers, carrageenan, paraffin, petrolatum and any combinations or mixtures thereof. In some other embodiments, hydroxypropylmethylcellulose (Methocel®) is utilized as the gelling agent. In certain embodiments, the viscosity enhancing agents described herein are also utilized as the gelling agent for the gel formulations presented herein.

In some embodiments, the otic therapeutic agents disclosed herein are dispensed as an auris-acceptable paint. As used herein, paints (also known as film formers) are solutions comprised of a solvent, a monomer or polymer, an active agent, and optionally one or more pharmaceutically-acceptable excipients. After application to a tissue, the solvent evaporates leaving behind a thin coating comprised of the monomers or polymers, and the active agent. The coating protects active agents and maintains them in an immobilized state at the site of application. This decreases the amount of active agent which may be lost and correspondingly increases the amount delivered to the subject. By way of non-limiting example, paints include collodions (e.g. Flexible Collodion, USP), and solutions comprising saccharide siloxane copolymers and a cross-linking agent. Collodions are ethyl ether/ethanol solutions containing pyroxylin (a nitrocellulose). After application, the ethyl ether/ethanol solution evaporates leaving behind a thin film of pyroxylin. In solutions comprising saccharide siloxane copolymers, the saccharide siloxane copolymers form the coating after evaporation of the solvent initiates the cross-linking of the saccharide siloxane copolymers. For additional disclosures regarding paints, see *Remington: The Science and Practice of Pharmacy* which is hereby incorporated with respect to this subject matter. The paints contemplated for use herein, are flexible such that they do not interfere with the propagation of pressure waves through the ear. Further, the paints may be applied as a liquid (i.e. solution, suspension, or emulsion), a semisolid (i.e. a gel, foam, paste, or jelly) or an aerosol.

In some embodiments, the otic therapeutic agents disclosed herein are dispensed as a controlled-release foam. Examples of suitable foamable carriers for use in the compositions disclosed herein include, but are not limited to, alginate and derivatives thereof, carboxymethylcellulose and derivatives thereof, collagen, polysaccharides, including, for example, dextran, dextran derivatives, pectin, starch, modified starches such as starches having additional carboxyl and/or carboxamide groups and/or having hydrophilic side-chains, cellulose and derivatives thereof, agar and derivatives thereof, such as agar stabilised with polyacrylamide, polyethylene oxides, glycol methacrylates, gelatin, gums such as xanthum, guar, karaya, gellan, arabic, tragacanth and locust bean gum, or combinations thereof. Also suitable are the salts of the aforementioned carriers, for example, sodium alginate. The formulation optionally further comprises a foaming agent, which promotes the formation of the foam, including a surfactant or external propellant. Examples of suitable foaming agents include cetrimide, lecithin, soaps, silicones and the like. Commercially available surfactants such as Tween® are also suitable.

In some embodiments, other gel formulations are useful depending upon the particular aural pressure modulating agent, other pharmaceutical agent or excipients/additives used, and as such are considered to fall within the scope of the present disclosure. For example, other commercially-available glycerin-based gels, glycerin-derived compounds, conjugated, or crosslinked gels, matrices, hydrogels, and polymers, as well as gelatins and their derivatives, alginates, and alginate-based gels, and even various native and synthetic hydrogel and hydrogel-derived compounds are all expected to be useful in the aural pressure modulating agent formulations described herein. In some embodiments, auris-acceptable gels include, but are not limited to, alginate hydrogels SAF®-Gel (ConvaTec, Princeton, N.J.), Duoderm® Hydroactive Gel (ConvaTec), Nu-Gel® (Johnson & Johnson Medical, Arlington, Tex.); Carrasyn® (V) Acemannan Hydrogel (Carrington Laboratories, Inc., Irving, Tex.); glycerin gels Elta® Hydrogel (Swiss-American Products, Inc., Dallas, Tex.) and K-Y® Sterile (Johnson & Johnson). In further embodiments, biodegradable biocompatible gels also represent compounds present in auris-acceptable formulations disclosed and described herein.

In some formulations developed for administration to a mammal, and for compositions formulated for human administration, the auris-acceptable gel comprises substantially all of the weight of the composition. In other embodiments, the auris-acceptable gel comprises as much as about 98% or about 99% of the composition by weight. This is desirous when a substantially non-fluid, or substantially viscous formulation is needed. In a further embodiment, when slightly less viscous, or slightly more fluid auris-acceptable pharmaceutical gel formulations are desired, the biocompatible gel portion of the formulation comprises at least about 50% by weight, at least about 60% by weight, at least about 70% by weight, or even at least about 80% or 90% by weight of the compound. All intermediate integers within these ranges are contemplated to fall within the scope of this disclosure, and in some alternative embodiments, even more fluid (and consequently less viscous) auris-acceptable gel compositions are formulated, such as for example, those in which the gel or matrix component of the mixture comprises not more than about 50% by weight, not more than about 40% by weight, not more than about 30% by weight, or even those than comprise not more than about 15% or about 20% by weight of the composition.

Auris-Acceptable Suspending Agents

In one embodiment, at least one aural pressure modulating agent is included in a pharmaceutically acceptable enhanced viscosity formulation wherein the formulation further comprises at least one suspending agent, wherein the suspending agent assists in imparting controlled release characteristics to the formulation. In some embodiments, suspending agents also serve to increase the viscosity of the auris-acceptable aural pressure modulating formulations and compositions.

Suspending agents include, by way of example only, compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), sodium carboxymethylcellulose, methylcellulose, hydroxypropylmethylcellulose (hypromellose), hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like. In some embodiments, useful aqueous suspensions also contain one or more polymers as suspending agents. Useful polymers include water-soluble polymers such as cellulosic polymers, e.g., hydroxypropyl methylcellulose, and water-insoluble polymers such as cross-linked carboxyl-containing polymers.

In one embodiment, the present disclosure provides auris-acceptable gel compositions comprising a therapeutically effective amount of an aural pressure modulating agent in a hydroxyethyl cellulose gel. Hydroxyethyl cellulose (HEC) is obtained as a dry powder which is reconstituted in water or an aqueous buffer solution to give the desired viscosity (generally about 200 cps to about 30,000 cps, corresponding to about 0.2 to about 10% HEC). In one embodiment the concentration of HEC is between about 1% and about 15%, about 1% and about 2%, or about 1.5% to about 2%.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Auris-Acceptable Actinic Radiation Curable Gel

In other embodiments, the gel is an actinic radiation curable gel, such that following administration to or near the targeted auris structure, use of actinic radiation (or light, including UV light, visible light, or infrared light) the desired gel properties are formed. By way of example only, fiber optics are used to provide the actinic radiation so as to form the desired gel properties. In some embodiments, the fiber optics and the gel administration device form a single unit. In other embodiments, the fiber optics and the gel administration device are provided separately.

Auris-Acceptable Solvent Release Gel

In some embodiments, the gel is a solvent release gel such that the desired gel properties are formed after administration to or near the targeted auris structure, that is, as the solvent in the injected gel formulation diffuses out the gel, a gel having the desired gel properties is formed. For example, a formulation that comprises sucrose acetate isobutyrate, a pharmaceutically acceptable solvent, one or more additives, and the aural pressure modulating agent is administered at or near the round window membrane: diffusion of the solvent out of the injected formulation provides a depot having the desired gel properties. For example, use of a water soluble solvent provides a high viscosity depot when the solvent diffuses rapidly out of the injected formulation. On the other hand, use of a hydrophobic solvent (e.g., benzyl benzoate) provides a less viscous depot. One example of an auris-acceptable solvent release gel formulation is the SABER™ Delivery System marketed by DURECT Corporation.

Auris-Acceptable In Situ Forming Spongy Material

Also contemplated within the scope of the embodiments is the use of a spongy material, formed in situ in the auris interna or auris media. In some embodiments, the spongy material is formed from hyaluronic acid or its derivatives. The spongy material is impregnated with a desired aural pressure modulating agent and placed within the auris media so as to provide controlled release of the aural pressure modulating agent within the auris media, or in contact with the round window membrane so as to provide controlled release of the aural pressure modulating agent into the auris interna. In some embodiments, the spongy material is biodegradable.

Round Window Membrane Mucoadhesives

Also contemplated within the scope of the embodiments is the addition of a round window membrane mucoadhesive with the aural pressure modulating agent formulations and compositions and devices disclosed herein. The term 'mucoadhesion' is used for materials that bind to the mucin layer of a biological membrane, such as the external membrane of the 3-layered round window membrane. To serve as round window membrane mucoadhesive polymers, the polymers possess some general physiochemical features such as predominantly anionic hydrophilicity with numerous hydrogen bond forming groups, suitable surface property for wetting mucus/mucosal tissue surfaces or sufficient flexibility to penetrate the mucus network.

Round window membrane mucoadhesive agents that are used with the auris-acceptable formulations include, but are not limited to, at least one soluble polyvinylpyrrolidone polymer (PVP); a water-swellable, but water-insoluble, fibrous, cross-linked carboxy-functional polymer; a cross-linked poly(acrylic acid) (e.g. Carbopol® 947P); a carbomer homopolymer; a carbomer copolymer; a hydrophilic polysaccharide gum, maltodextrin, a cross-linked alignate gum gel, a water-dispersible polycarboxylated vinyl polymer, at least two particulate components selected from the group consisting of titanium dioxide, silicon dioxide, and clay, or a mixture thereof. The round window membrane mucoadhesive agent is optionally used in combination with an auris-acceptable viscosity increasing excipient, or used alone to increase the interaction of the composition with the mucosal layer target otic component. In one non-limiting example, the mucoadhesive agent is maltodextrin. In some embodiments, the mucoadhesive agent is an alginate gum. When used, the round window membrane mucoadhesive character imparted to the composition is at a level that is sufficient to deliver an effective amount of the aural pressure modulating agent composition to, for example, the mucosal layer of round window membrane or the crista fenestrae cochleae in an amount that coats the mucosal membrane, and thereafter deliver the composition to the affected areas, including by way of example only, the vestibular and/or cochlear structures of the auris interna. When used, the mucoadhesive characteristics of the compositions provided herein are determined, and using this information (along with the other teachings provided herein), the appropriate amounts are determined. One method for determining sufficient mucoadhesiveness includes monitoring changes in the interaction of the composition with a mucosal layer, including but not limited to measuring changes in residence or retention time of the composition in the absence and presence of the mucoadhesive excipient.

Mucoadhesive agents have been described, for example, in U.S. Pat. Nos. 6,638,521, 6,562,363, 6,509,028, 6,348,502, 6,319,513, 6,306,789, 5,814,330, and 4,900,552, each of which is hereby incorporated by reference for such disclosure.

In another non-limiting example, a mucoadhesive agent is, for example, at least two particulate components selected from titanium dioxide, silicon dioxide, and clay, wherein the composition is not further diluted with any liquid prior to administration and the level of silicon dioxide, if present, is from about 3% to about 15%, by weight of the composition. Silicon dioxide, if present, includes fumed silicon dioxide, precipitated silicon dioxide, coacervated silicon dioxide, gel silicon dioxide, and mixtures thereof. Clay, if present, includes kaolin minerals, serpentine minerals, smectites, illite or a mixture thereof. For example, clay includes laponite, bentonite, hectorite, saponite, montmorillonites or a mixture thereof.

In one non-limiting example, the round window membrane mucoadhesive agent is maltodextrin. Maltodextrin is a carbohydrate produced by the hydrolysis of starch that is optionally derived from corn, potato, wheat or other plant products. Maltodextrin is optionally used either alone or in combination with other round window membrane mucoadhesive agents to impart mucoadhesive characteristics on the compositions disclosed herein. In one embodiment, a combination of maltodextrin and a carbopol polymer are used to increase the round window membrane mucoadhesive characteristics of the compositions or devices disclosed herein.

In another embodiment, the round window membrane mucoadhesive agent is an alkyl-glycoside and/or a saccharide alkyl ester. As used herein, an "alkyl-glycoside" means a compound comprising any hydrophilic saccharide (e.g. sucrose, maltose, or glucose) linked to a hydrophobic alkyl. In some embodiments, the round window membrane mucoadhesive agent is an alkyl-glycoside wherein the alkyl-glycoside comprises a sugar linked to a hydrophobic alkyl (e.g., an alkyl comprising about 6 to about 25 carbon atoms) by an amide linkage, an amine linkage, a carbamate linkage, an ether linkage, a thioether linkage, an ester linkage, a thioester linkage, a glycosidic linkage, a thioglycosidic linkage, and/or a ureide linkage. In some embodiments, the round window membrane mucoadhesive agent is a hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-maltoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-glucoside; hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-sucroside; hexyl-, heptyl-, octyl-, dodecyl-, tridecyl-, and tetradecyl-β-D-thiomaltoside; heptyl- or octyl-1-thio-α- or β-D-glucopyranoside; alkyl thiosucroses; alkyl maltotriosides; long chain aliphatic carbonic acid amides of sucrose β-amino-alkyl ethers; derivatives of palatinose or isomaltamine linked by an amide linkage to an alkyl chain and derivatives of isomaltamine linked by urea to an alkyl chain; long chain aliphatic carbonic acid ureides of sucrose β-amino-alkyl ethers and long chain aliphatic carbonic acid amides of sucrose β-amino-alkyl ethers. In some embodiments, the round window membrane mucoadhesive agent is an alkyl-glycoside wherein the alkyl glycoside is maltose, sucrose, glucose, or a combination thereof linked by a glycosidic linkage to an alkyl chain of 9-16 carbon atoms (e.g., nonyl-, decyl-, dodecyl- and tetradecyl sucroside; nonyl-, decyl-, dodecyl- and tetradecyl glucoside; and nonyl-, decyl-, dodecyl- and tetradecyl maltoside). In some embodiments, the round window membrane mucoadhesive agent is an alkyl-glycoside wherein the alkyl glycoside is dodecylmaltoside, tridecylmaltoside, and tetradecylmaltoside.

In some embodiments, the round window membrane mucoadhesive agent is an alkyl-glycoside wherein the alkyl-glycoside is a disaccharide with at least one glucose. In some embodiments, the auris acceptable penetration enhancer is a surfactant comprising α-D-glucopyranosyl-β-glycopyranoside, n-Dodecyl-4-O-α-D-glucopyranosyl-β-glycopyranoside, and/or n-tetradecyl-4-O-α-D-glucopyranosyl-β-glycopyranoside. In some embodiments, the round window membrane mucoadhesive agent is an alkyl-glycoside wherein the alkyl-glycoside has a critical miscelle concentration (CMC) of less than about 1 mM in pure water or in aqueous solutions. In some embodiments, the round window membrane mucoadhesive agent is an alkyl-glycoside wherein an oxygen atom within the alkyl-glycoside is substituted with a sulfur atom. In some embodiments, the round window membrane mucoadhesive agent is an alkyl-glycoside wherein the alkylglycoside is the β anomer. In some embodiments, the round window membrane mucoadhesive agent is an alkyl-glycoside wherein the alkylglycoside comprises 90%, 91%, 92%, 93%, 94%, 95%, 96%, 97%, 98%, 99%, 99.1%, 99.5%, or 99.9% of the β anomer.

Auris-Acceptable Controlled Release Particles

Aural pressure modulating agents and/or other pharmaceutical agents disclosed herein are optionally incorporated within controlled release particles, lipid complexes, liposomes, nanoparticles, microparticles, microspheres, coacervates, nanocapsules or other agents which enhance or facilitate the localized delivery of the aural pressure modulating agent. In some embodiments, a single enhanced viscosity formulation is used, in which at least one aural pressure modulating agent is present, while in other embodiments, a pharmaceutical formulation that comprises a mixture of two or more distinct enhanced viscosity formulations is used, in which at least one aural pressure modulating agent is present. In some embodiments, combinations of sols, gels and/or biocompatible matrices is also employed to provide desirable characteristics of the controlled release aural pressure modulating compositions or formulations. In certain embodiments, the controlled release aural pressure modulating formulations or compositions are cross-linked by one or more agents to alter or improve the properties of the composition.

Examples of microspheres relevant to the pharmaceutical formulations disclosed herein include: Luzzi, L. A., J. Pharm. Psy. 59:1367 (1970); U.S. Pat. No. 4,530,840; Lewis, D. H., "Controlled Release of Bioactive Agents from Lactides/Glycolide Polymers" in Biodegradable Polymers as Drug Delivery Systems, Chasin, M. and Langer, R., eds., Marcel Decker (1990); U.S. Pat. No. 4,675,189; Beck et al., "Poly(lactic acid) and Poly(lactic acid-co-glycolic acid) Contraceptive Delivery Systems," in Long Acting Steroid Contraception, Mishell, D. R., ed., Raven Press (1983); U.S. Pat. No. 4,758,435; U.S. Pat. No. 3,773,919; U.S. Pat. No. 4,474,572. Examples of protein therapeutics formulated as microspheres include: U.S. Pat. No. 6,458,387; U.S. Pat. No. 6,268,053; U.S. Pat. No. 6,090,925; U.S. Pat. No. 5,981,719; and U.S. Pat. No. 5,578,709, and are herein incorporated by reference for such disclosure.

Microspheres usually have a spherical shape, although irregularly-shaped microparticles are possible. Microspheres may vary in size, ranging from submicron to 1000 micron diameters. Microspheres suitable for use with the auris-acceptable formulations disclosed herein are submicron to 250 micron diameter microspheres, allowing administration by injection with a standard gauge needle. The auris-acceptable microspheres are prepared by any method which produces microspheres in a size range acceptable for use in an injectable composition. Injection is optionally accomplished with standard gauge needles used for administering liquid compositions.

Suitable examples of polymeric matrix materials for use in the auris-acceptable controlled release particles herein include poly(glycolic acid), poly-d,l-lactic acid, poly-1-lactic acid, copolymers of the foregoing, poly(aliphatic carboxylic acids), copolyoxalates, polycaprolactone, polydioxonene, poly(orthocarbonates), poly(acetals), poly(lactic acid-caprolactone), polyorthoesters, poly(glycolic acid-caprolactone), polydioxonene, polyanhydrides, polyphosphazines, and natural polymers including albumin, casein, and some waxes, such as, glycerol mono- and distearate, and the like. Various commercially available poly (lactide-co-glycolide) materials (PLGA) are optionally used in the method disclosed herein. For example, poly (d,l-lactic-co-glycolic acid) is commercially available from Boehringer-Ingelheim as RESOMER RG 503 H. This product has a mole percent composition of 50% lactide and 50% glycolide. These copolymers are available in a wide range of molecular weights and ratios of lactic acid to glycolic acid. One embodiment includes the use of the polymer poly(d,l-lactide-co-glycolide). The molar ratio of lactide to glycolide in such a copolymer includes the range of from about 95:5 to about 50:50.

The molecular weight of the polymeric matrix material is of some importance. The molecular weight should be high enough so that it forms satisfactory polymer coatings, i.e., the polymer should be a good film former. Usually, a satisfactory molecular weight is in the range of 5,000 to 500,000 daltons. The molecular weight of a polymer is also important from the point of view that molecular weight influences the biodegradation rate of the polymer. For a diffusional mechanism of drug release, the polymer should remain intact until all of the drug is released from the microparticles and then degrade. The drug is also released from the microparticles as the polymeric excipient bioerodes. By an appropriate selection of polymeric materials a microsphere formulation is made such that the resulting microspheres exhibit both diffusional release and biodegradation release properties. This is useful in affording multiphasic release patterns.

A variety of methods are known by which compounds are encapsulated in microspheres. In these methods, the aural pressure modulating agent is generally dispersed or emulsified, using stirrers, agitators, or other dynamic mixing techniques, in a solvent containing a wall-forming material. Solvent is then removed from the microspheres, and thereafter the microsphere product is obtained.

In one embodiment, controlled release aural pressure modulating formulations are made through the incorporation of the aural pressure modulating agents and/or other pharmaceutical agents into ethylene-vinyl acetate copolymer matrices. (See U.S. Pat. No. 6,083,534, incorporated herein for such disclosure). In another embodiment, aural pressure modulating agents are incorporated into poly (lactic-glycolic acid) or poly-L-lactic acid microspheres. Id. In yet another embodiment, the aural pressure modulating agents are encapsulated into alginate microspheres. (See U.S. Pat. No. 6,036,978, incorporated herein for such disclosure). Biocompatible methacrylate-based polymers to encapsulate the aural pressure modulating compounds or compositions are optionally used in the formulations and methods disclosed herein. A wide range of methacrylate-based polymer systems are commercially available, such as the EUDRAGIT polymers marketed by Evonik. One useful aspect of methacrylate polymers is that the properties of the formulation are varied by incorporating various co-polymers. For example, poly(acrylic acid-co-methylmethacrylate) microparticles exhibit enhanced mucoadhesion properties as the carboxylic acid groups in the poly(acrylic acid) form hydrogen bonds with mucin (Park et al, Pharm. Res. (1987) 4(6):457-464). Variation of the ratio between acrylic acid and methylmethacrylate monomers serves to modulate the properties of the co-polymer. Methacrylate-based microparticles have also been used in protein therapeutic formulations (Naha et al, Journal of Microencapsulation 4 Feb. 2008 (online publication)). In one embodiment, the enhanced viscosity auris-acceptable formulations described herein comprises aural pressure modulating microspheres wherein the microspheres are formed from a methacrylate polymer or copolymer. In an additional embodiment, the enhanced viscosity formulation described herein comprises aural pressure modulating microspheres wherein the microspheres are mucoadhesive. Other controlled release systems, including incorporation or deposit of polymeric materials or matrices onto solid or hollow spheres containing aural pressure modulating agents, are also explicitly contemplated within the embodiments disclosed herein. The types of controlled release systems available without significantly losing activity of the aural pressure modulating agent are determined using the teachings, examples, and principles disclosed herein An example of a conventional microencapsulation process for pharmaceutical preparations is shown in U.S. Pat. No. 3,737,337, incorporated herein by reference for such disclosure. The aural pressure modulating substances to be encapsulated or embedded are dissolved or dispersed in the organic solution of the polymer (phase A), using conventional mixers, including (in the preparation of dispersion) vibrators and high-speed stirrers, etc. The dispersion of phase (A), containing the core material in solution or in suspension, is carried out in the aqueous phase (B), again using conventional mixers, such as high-speed mixers, vibration mixers, or even spray nozzles, in which case the particle size of the microspheres will be determined not only by the concentration of phase (A), but also by the emulsate or microsphere size. With conventional techniques for the microencapsulation of aural pressure modulating agents, the microspheres form when the solvent containing an active agent and a polymer is emulsified or dispersed in an immiscible solution by stirring, agitating, vibrating, or some other dynamic mixing technique, often for a relatively long period of time.

Methods for the construction of microspheres are also described in U.S. Pat. No. 4,389,330, and U.S. Pat. No. 4,530,840, incorporated herein by reference for such disclosure. The desired aural pressure modulating agent is dissolved or dispersed in an appropriate solvent. To the agent-containing medium is added the polymeric matrix material in an amount relative to the active ingredient which gives a product of the desired loading of active agent. Optionally, all of the ingredients of the aural pressure modulating microsphere product can be blended in the solvent medium together. Suitable solvents for the agent and the polymeric matrix material include organic solvents such as acetone, halogenated hydrocarbons such as chloroform, methylene chloride and the like, aromatic hydrocarbon compounds, halogenated aromatic hydrocarbon compounds, cyclic ethers, alcohols, ethyl acetate and the like.

The mixture of ingredients in the solvent is emulsified in a continuous-phase processing medium; the continuous-phase medium being such that a dispersion of microdroplets containing the indicated ingredients is formed in the continuous-phase medium. Naturally, the continuous-phase processing medium and the organic solvent must be immiscible, and includes water although nonaqueous media such as xylene and toluene and synthetic oils and natural oils are optionally used. Optionally, a surfactant is added to the continuous-phase processing medium to prevent the microparticles from agglomerating and to control the size of the solvent microdroplets in the emulsion. A preferred surfactant-dispersing medium combination is a 1 to 10 wt. % poly (vinyl alcohol) in water mixture. The dispersion is formed by mechanical agitation of the mixed materials. An emulsion is optionally formed by adding small drops of the active agent-wall forming material solution to the continuous phase processing medium. The temperature during the formation of the emulsion is not especially critical but influences the size and quality of the microspheres and the solubility of the drug in the continuous phase. It is desirable to have as little of the agent in the continuous phase as possible. Moreover, depending on the solvent and continuous-phase processing medium employed, the temperature must not be too low or the solvent and processing medium will solidify or the processing medium will become too viscous for practical purposes, or too high that the processing medium will evaporate, or that the liquid processing medium will not be maintained. Moreover, the temperature of the medium cannot be so high that the stability of the particular agent being incorporated in the microspheres is adversely affected. Accordingly, the dispersion process is conducted at any temperature which maintains stable operating conditions, which preferred temperature being about 15° C. to 60° C., depending upon the drug and excipient selected.

The dispersion which is formed is a stable emulsion and from this dispersion the organic solvent immiscible fluid is optionally partially removed in the first step of the solvent removal process. The solvent is removed by techniques such as heating, the application of a reduced pressure or a combination of both. The temperature employed to evaporate solvent from the microdroplets is not critical, but should not be that high that it degrades the aural pressure modulating agent employed in the preparation of a given microparticle, nor should it be so high as to evaporate solvent at such a rapid rate to cause defects in the wall forming material. Generally, from 5 to 75%, of the solvent is removed in the first solvent removal step.

After the first stage, the dispersed microparticles in the solvent immiscible fluid medium are isolated from the fluid medium by any convenient means of separation. Thus, for example, the fluid is decanted from the microsphere or the microsphere suspension is filtered. Still other, various combinations of separation techniques are used if desired.

Following the isolation of the microspheres from the continuous-phase processing medium, the remainder of the solvent in the microspheres is removed by extraction. In this step, the microspheres are suspended in the same continuous-phase processing medium used in step one, with or without surfactant, or in another liquid. The extraction medium removes the solvent from the microspheres and yet does not dissolve the microspheres. During the extraction, the extraction medium with dissolved solvent is optionally removed and replaced with fresh extraction medium. This is best done on a continual basis. The rate of extraction medium replenishment of a given process is a variable which is determined at the time the process is performed and, therefore, no precise limits for the rate must be predetermined. After the majority of the solvent has been removed from the microspheres, the microspheres are dried by exposure to air or by other conventional drying techniques such as vacuum drying, drying over a desiccant, or the like. This process is very efficient in encapsulating the aural pressure modulating agent since core loadings of up to 80 wt. %, preferably up to 60 wt. % are obtained.

Alternatively, controlled release microspheres containing an aural pressure modulating agent is prepared through the use of static mixers. Static or motionless mixers consist of a conduit or tube in which is received a number of static mixing agents. Static mixers provide homogeneous mixing in a relatively short length of conduit, and in a relatively short period of time. With static mixers, the fluid moves through the mixer, rather than some part of the mixer, such as a blade, moving through the fluid.

A static mixer is optionally used to create an emulsion. When using a static mixer to form an emulsion, several factors determine emulsion particle size, including the density and viscosity of the various solutions or phases to be mixed, volume ratio of the phases, interfacial tension between the phases, static mixer parameters (conduit diameter; length of mixing element; number of mixing elements), and linear velocity through the static mixer. Temperature is a variable because it affects density, viscosity, and interfacial tension. The controlling variables are linear velocity, sheer rate, and pressure drop per unit length of static mixer.

In order to create microspheres containing an aural pressure modulating agent using a static mixer process, an organic phase and an aqueous phase are combined. The organic and aqueous phases are largely or substantially immiscible, with the aqueous phase constituting the continuous phase of the emulsion. The organic phase includes an aural pressure modulating agent as well as a wall-forming polymer or polymeric matrix material. The organic phase is prepared by dissolving an aural pressure modulating agent in an organic or other suitable solvent, or by forming a dispersion or an emulsion containing the aural pressure modulating agent. The organic phase and the aqueous phase are pumped so that the two phases flow simultaneously through a static mixer, thereby forming an emulsion which comprises microspheres containing the aural pressure modulating agent encapsulated in the polymeric matrix material. The organic and aqueous phases are pumped through the static mixer into a large volume of quench liquid to extract or remove the organic solvent. Organic solvent is optionally removed from the microspheres while they are washing or being stirred in the quench liquid. After the microspheres are washed in a quench liquid, they are isolated, as through a sieve, and dried.

In one embodiment, microspheres are prepared using a static mixer. The process is not limited to the solvent extraction technique discussed above, but is used with other encapsulation techniques. For example, the process is optionally used with a phase separation encapsulation technique. To do so, an organic phase is prepared that comprises an aural pressure modulating agent suspended or dispersed in a polymer solution. The non-solvent second phase is free from solvents for the polymer and active agent. A preferred non-solvent second phase is silicone oil. The organic phase and the non-solvent phase are pumped through a static mixer into a non-solvent quench liquid, such as heptane. The semi-solid particles are quenched for complete hardening and washing. The process of microencapsulation includes spray drying, solvent evaporation, a combination of evaporation and extraction, and melt extrusion.

In another embodiment, the microencapsulation process involves the use of a static mixer with a single solvent. This process is described in detail in U.S. application Ser. No. 08/338,805, herein incorporated by reference for such disclosure. An alternative process involves the use of a static mixer with co-solvents. In this process, biodegradable microspheres comprising a biodegradable polymeric binder and an aural pressure modulating agent are prepared, which comprises a blend of at least two substantially non-toxic solvents, free of halogenated hydrocarbons to dissolve both the agent and the polymer. The solvent blend containing the dissolved agent and polymer is dispersed in an aqueous solution to form droplets. The resulting emulsion is then added to an aqueous extraction medium preferably containing at least one of the solvents of the blend, whereby the rate of extraction of each solvent is controlled, whereupon the biodegradable microspheres containing the pharmaceutically active agent are formed. This process has the advantage that less extraction medium is required because the solubility of one solvent in water is substantially independent of the other and solvent selection is increased, especially with solvents that are particularly difficult to extract.

Nanoparticles are also contemplated for use with the aural pressure modulating agents disclosed herein. Nanoparticles are material structures of about 100 nm or less in size. One use of nanoparticles in pharmaceutical formulations is the formation of suspensions as the interaction of the particle surface with solvent is strong enough to overcome differences in density. Nanoparticle suspensions are sterilized as the nanoparticles are small enough to be subjected to sterilizing filtration (see, e.g., U.S. Pat. No. 6,139,870, herein incorporated by reference for such disclosure). Nanoparticles comprise at least one hydrophobic, water-insoluble and water-indispersible polymer or copolymer emulsified in a solution or aqueous dispersion of surfactants, phospholipids or fatty acids. The aural pressure modulating agent is optionally introduced with the polymer or the copolymer into the nanoparticles.

Lipid nanocapsules as controlled release structures, as well for penetrating the round window membrane and reaching auris interna and/or auris media targets, is also contemplated herein. Lipid nanocapsules are optionally formed by emulsifying capric and caprylic acid triglycerides (Labrafac WL 1349; avg. mw 512), soybean lecithin (LIPOID® S75-3; 69% phosphatidylcholine and other phospholipids), surfactant (for example, Solutol HS15), a mixture of polyethylene glycol 660 hydroxystearate and free polyethylene glycol 660; NaCl and water. The mixture is stirred at room temperature to obtain an oil emulsion in water. After progressive heating at a rate of 4° C./min under magnetic stirring, a short interval of transparency should occur close to 70° C., and the inverted phase (water droplets in oil) obtained at 85° C. Three cycles of cooling and heating is then applied between 85° C. and 60° C. at the rate of 4° C./min, and a fast dilution in cold water at a temperature close to 0° C. to produce a suspension of nanocapsules. To encapsulate the aural pressure modulating agents, the agent is optionally added just prior to the dilution with cold water.

Aural pressure modulating agents are also inserted into the lipid nanocapsules by incubation for 90 minutes with an aqueous micellar solution of the auris active agent. The suspension is then vortexed every 15 minutes, and then quenched in an ice bath for 1 minute.

Suitable auris-acceptable surfactants are, by way of example, cholic acid or taurocholic acid salts. Taurocholic acid, the conjugate formed from cholic acid and taurine, is a fully metabolizable sulfonic acid surfactant. An analog of taurocholic acid, tauroursodeoxycholic acid (TUDCA), is a naturally occurring bile acid and is a conjugate of taurine and ursodeoxycholic acid (UDCA). Other naturally occurring anionic (e.g., galactocerebroside sulfate), neutral (e.g., lactosylceramide) or zwitterionic surfactants (e.g., sphingomyelin, phosphatidyl choline, palmitoyl carnitine) are optionally used to prepare nanoparticles.

The auris-acceptable phospholipids are chosen, by way of example, from natural, synthetic or semi-synthetic phospholipids; lecithins (phosphatidylcholine) such as, for example, purified egg or soya lecithins (lecithin E100, lecithin E80 and phospholipons, for example phospholipon 90), phosphatidylethanolamine, phosphatidylserine, phosphatidylinositol, phosphatidylglycerol, dipalmitoylphosphatidylcholine, dipalmitoylglycerophosphatidylcholine, dimyristoylphosphatidylcholine, distearoylphosphatidylcholine and phosphatidic acid or mixtures thereof are used more particularly.

Fatty acids for use with the auris-acceptable formulations are chosen from, by way of example, lauric acid, mysristic acid, palmitic acid, stearic acid, isostearic acid, arachidic acid, behenic acid, oleic acid, myristoleic acid, palmitoleic acid, linoleic acid, alpha-linoleic acid, arachidonic acid, eicosapentaenoic acid, erucic acid, docosahexaenoic acid, and the like.

Suitable auris-acceptable surfactants are selected from known organic and inorganic pharmaceutical excipients. Such excipients include various polymers, low molecular weight oligomers, natural products, and surfactants. Preferred surface modifiers include nonionic and ionic surfactants. Two or more surface modifiers are used in combination.

Representative examples of auris-acceptable surfactants include cetyl pyridinium chloride, gelatin, casein, lecithin (phosphatides), dextran, glycerol, gum acacia, cholesterol, tragacanth, stearic acid, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters; dodecyl trimethyl ammonium bromide, polyoxyethylenestearates, colloidal silicon dioxide, phosphates, sodium dodecylsulfate, carboxymethylcellulose calcium, hydroxypropyl cellulose (HPC, HPC-SL, and HPC-L), hydroxypropyl methylcellulose (HPMC), carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol (PVA), polyvinylpyrrolidone (PVP), 4-(1,1,3,3-tetaamethylbutyl)-phenol polymer with ethylene oxide and formaldehyde (also known as tyloxapol, superione, and triton), poloxamers, poloxamines, a charged phospholipid such as dimyristoyl phophatidyl glycerol, dioctylsulfosuccinate (DOSS); Tetronic® 1508, dialkylesters of sodium sulfosuccinic acid, Duponol P, Tritons X-200, Crodestas F-110, p-isononylphenoxypoly-(glycidol), Crodestas SL-40 (Croda, Inc.); and SA9OHCO, which is $C_{18}H_{37}CH_2$ $(CON(CH_3)$—$CH_2$ $(CHOH)_4$ $(CH_2OH)_2$ (Eastman Kodak Co.); decanoyl-N-methylglucamide; n-decyl β-D-glucopyranoside; n-decyl β-D-maltopyranoside; n-dodecyl β-D-glucopyranoside; n-dodecyl β-D-maltoside; heptanoyl-N-methylglucamide; n-heptyl-β-D-glucopyranoside; n-heptyl β-D-thioglucoside; n-hexyl β-D-glucopyranoside; nonanoyl-N-methylglucamide; n-noyl β-D-glucopyranoside; octanoyl-N-methylglucamide; n-octyl-β-D-glucopyranoside; octyl β-D-thioglucopyranoside; and the like. Most of these surfactants are known pharmaceutical excipients and are described in detail in the Handbook of Pharmaceutical Excipients, published jointly by the American Pharmaceutical Association and The Pharmaceutical Society of Great Britain (The Pharmaceutical Press, 1986), specifically incorporated by reference for such disclosure.

The hydrophobic, water-insoluble and water-indispersible polymer or copolymer may be chosen from biocompatible and biodegradable polymers, for example lactic or glycolic acid polymers and copolymers thereof, or polylactic/polyethylene (or polypropylene) oxide copolymers, preferably with molecular weights of between 1000 and 200,000, polyhydroxybutyric acid polymers, polylactones of fatty acids containing at least 12 carbon atoms, or polyanhydrides.

The nanoparticles may be obtained by coacervation, or by the technique of evaporation of solvent, from an aqueous dispersion or solution of phospholipids and of an oleic acid salt into which is added an immiscible organic phase comprising the active principle and the hydrophobic, water-insoluble and water-indispersible polymer or copolymer. The mixture is pre-emulsified and then subjected to homogenization and evaporation of the organic solvent to obtain an aqueous suspension of very small-sized nanoparticles.

A variety of methods are optionally employed to fabricate the aural pressure modulating nanoparticles that are within the scope of the embodiments. These methods include vaporization methods, such as free jet expansion, laser vaporization, spark erosion, electro explosion and chemical vapor deposition; physical methods involving mechanical attrition (e.g., "pearlmilling" technology, Elan Nanosystems), super critical CO2 and interfacial deposition following solvent displacement. In one embodiment, the solvent displacement method is used. The size of nanoparticles produced by this method is sensitive to the concentration of polymer in the organic solvent; the rate of mixing; and to the surfactant employed in the process. Continuous flow mixers provide the necessary turbulence to ensure small particle size. One type of continuous flow mixing device that is optionally used to prepare nanoparticles has been described (Hansen et al J Phys Chem 92, 2189-96, 1988). In other embodiments, ultrasonic devices, flow through homogenizers or supercritical CO2 devices may be used to prepare nanoparticles.

If suitable nanoparticle homogeneity is not obtained on direct synthesis, then size-exclusion chromatography is used to produce highly uniform drug-containing particles that are freed of other components involved in their fabrication. Size-exclusion chromatography (SEC) techniques, such as gel-filtration chromatography, is used to separate particle-bound aural pressure modulating agent or other pharmaceutical compound from free aural pressure modulating agent or other pharmaceutical compound, or to select a suitable size range of aural pressure modulator-containing nanoparticles. Various SEC media, such as Superdex 200, Superose 6, Sephacryl 1000 are commercially available and are employed for the size-based fractionation of such mixtures. Additionally, nanoparticles are optionally purified by centrifugation, membrane filtration and by use of other molecular sieving devices, crosslinked gels/materials and membranes.

Auris-Acceptable Cyclodextrin and Other Stabilizing Formulations

In a specific embodiment, the auris-acceptable formulations alternatively comprises a cyclodextrin. Cyclodextrins are cyclic oligosaccharides containing 6, 7, or 8 glucopyranose units, referred to as α-cyclodextrin, β-cyclodextrin, or γ-cyclodextrin respectively. Cyclodextrins have a hydrophilic exterior, which enhances water-soluble, and a hydrophobic interior which forms a cavity. In an aqueous environment, hydrophobic portions of other molecules often enter the hydrophobic cavity of cyclodextrin to form inclusion compounds. Additionally, cyclodextrins are also capable of other types of nonbonding interactions with molecules that are not inside the hydrophobic cavity. Cyclodextrins have three free hydroxyl groups for each glucopyranose unit, or 18 hydroxyl groups on α-cyclodextrin, 21 hydroxyl groups on β-cyclodextrin, and 24 hydroxyl groups on γ-cyclodextrin. One or more of these hydroxyl groups can be reacted with any of a number of reagents to form a large variety of cyclodextrin derivatives, including hydroxypropyl ethers, sulfonates, and sulfoalkylethers. Shown below is the structure of β-cyclodextrin and the hydroxypropyl-β-cyclodextrin (HPβCD).

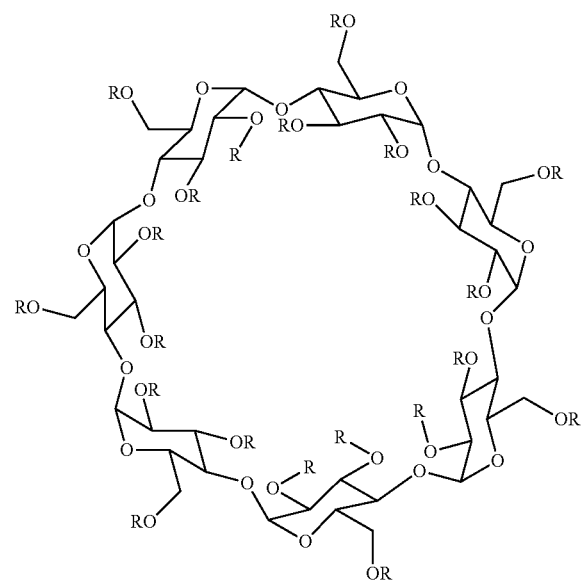

R = H
β-cylcodextrin

R = CH₂CH(OH)CH₃
hydroxypropyl β-cylcodextrin

In some embodiments, the use of cyclodextrins in the pharmaceutical compositions described herein improves the solubility of the drug. Inclusion compounds are involved in many cases of enhanced solubility; however other interactions between cyclodextrins and insoluble compounds also improves solubility. Hydroxypropyl-β-cyclodextrin (HPβCD) is commercially available as a pyrogen free product. It is a nonhygroscopic white powder that readily dissolves in water. HPβCD is thermally stable and does not degrade at neutral pH. Thus, cyclodextrins improve the solubility of a therapeutic agent in a composition or formulation. Accordingly, in some embodiments, cyclodextrins are included to increase the solubility of the auris-acceptable aural pressure modulating agents within the formulations described herein. In other embodiments, cyclodextrins in addition serve as controlled release excipients within the formulations described herein.

By way of example only, cyclodextrin derivatives for use include α-cyclodextrin, β-cyclodextrin, γ-cyclodextrin, hydroxyethyl β-cyclodextrin, hydroxypropyl γ-cyclodextrin, sulfated β-cyclodextrin, sulfated α-cyclodextrin, sulfobutyl ether β-cyclodextrin.

The concentration of the cyclodextrin used in the compositions and methods disclosed herein varies according to the physiochemical properties, pharmacokinetic properties, side effect or adverse events, formulation considerations, or other factors associated with the therapeutically active agent, or a salt or prodrug thereof, or with the properties of other excipients in the composition. Thus, in certain circumstances, the concentration or amount of cyclodextrin used in accordance with the compositions and methods disclosed herein will vary, depending on the need. When used, the amount of cyclodextrins needed to increase solubility of the aural pressure modulating agent and/or function as a controlled release excipient in any of the formulations described herein is selected using the principles, examples, and teachings described herein.

Other stabilizers that are useful in the auris-acceptable formulations disclosed herein include, for example, fatty acids, fatty alcohols, alcohols, long chain fatty acid esters, long chain ethers, hydrophilic derivatives of fatty acids, polyvinyl pyrrolidones, polyvinyl ethers, polyvinyl alcohols, hydrocarbons, hydrophobic polymers, moisture-absorbing polymers, and combinations thereof. In some embodiments, amide analogues of stabilizers are also used. In further embodiments, the chosen stabilizer changes the hydrophobicity of the formulation (e.g., oleic acid, waxes), or improves the mixing of various components in the formulation (e.g., ethanol), controls the moisture level in the formula (e.g., PVP or polyvinyl pyrrolidone), controls the mobility of the phase (substances with melting points higher than room temperature such as long chain fatty acids, alcohols, esters, ethers, amides etc. or mixtures thereof; waxes), and/or improves the compatibility of the formula with encapsulating materials (e.g., oleic acid or wax). In another embodiment some of these stabilizers are used as solvents/co-solvents (e.g., ethanol). In other embodiments, stabilizers are present in sufficient amounts to inhibit the degradation of the aural pressure modulating agent. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

Additional useful aural pressure modulating agent auris-acceptable formulations include one or more anti-aggregation additives to enhance stability of aural pressure modulating agent formulations by reducing the rate of protein aggregation. The anti-aggregation additive selected depends upon the nature of the conditions to which the aural pressure modulating agents, for example aural pressure modulating agent antibodies are exposed. For example, certain formulations undergoing agitation and thermal stress require a different anti-aggregation additive than a formulation undergoing lyophilization and reconstitution. Useful anti-aggregation additives include, by way of example only, urea, guanidinium chloride, simple amino acids such as glycine or arginine, sugars, polyalcohols, polysorbates, polymers such as polyethylene glycol and dextrans, alkyl saccharides, such as alkyl glycoside, and surfactants.

Other useful formulations optionally include one or more auris-acceptable antioxidants to enhance chemical stability where required. Suitable antioxidants include, by way of example only, ascorbic acid, methionine, sodium thiosulfate and sodium metabisulfite. In one embodiment, antioxidants are selected from metal chelating agents, thiol containing compounds and other general stabilizing agents.

Still other useful compositions include one or more auris-acceptable surfactants to enhance physical stability or for other purposes. Suitable nonionic surfactants include, but are not limited to, polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40.

In some embodiments, the auris-acceptable pharmaceutical formulations described herein are stable with respect to compound degradation over a period of any of at least about 1 day, at least about 2 days, at least about 3 days, at least about 4 days, at least about 5 days, at least about 6 days, at least about 1 week, at least about 2 weeks, at least about 3 weeks, at least about 4 weeks, at least about 5 weeks, at least about 6 weeks, at least about 7 weeks, at least about 8 weeks, at least about 3 months, at least about 4 months, at least about 5 months, or at least about 6 months. In other embodiments, the formulations described herein are stable with respect to compound degradation over a period of at least about 1 week. Also described herein are formulations that are stable with respect to compound degradation over a period of at least about 1 month.

In other embodiments, an additional surfactant (co-surfactant) and/or buffering agent is combined with one or more of the pharmaceutically acceptable vehicles previously described herein so that the surfactant and/or buffering agent maintains the product at an optimal pH for stability. Suitable co-surfactants include, but are not limited to: a) natural and synthetic lipophilic agents, e.g., phospholipids, cholesterol, and cholesterol fatty acid esters and derivatives thereof; b) nonionic surfactants, which include for example, polyoxyethylene fatty alcohol esters, sorbitan fatty acid esters (Spans), polyoxyethylene sorbitan fatty acid esters (e.g., polyoxyethylene (20) sorbitan monooleate (Tween 80), polyoxyethylene (20) sorbitan monostearate (Tween 60), polyoxyethylene (20) sorbitan monolaurate (Tween 20) and other Tweens, sorbitan esters, glycerol esters, e.g., Myrj and glycerol triacetate (triacetin), polyethylene glycols, cetyl alcohol, cetostearyl alcohol, stearyl alcohol, polysorbate 80, poloxamers, poloxamines, polyoxyethylene castor oil derivatives (e.g., Cremophor® RH40, Cremphor A25, Cremphor A20, Cremophor® EL) and other Cremophors, sulfosuccinates, alkyl sulphates (SLS); PEG glyceryl fatty acid esters such as PEG-8 glyceryl caprylate/caprate (Labrasol), PEG-4 glyceryl caprylate/caprate (Labrafac Hydro WL 1219), PEG-32 glyceryl laurate (Gelucire 444/14), PEG-6 glyceryl mono oleate (Labrafil M 1944 CS), PEG-6 glyceryl linoleate (Labrafil M 2125 CS); propylene glycol mono- and di-fatty acid esters, such as propylene glycol laurate, propylene glycol caprylate/caprate; Brij® 700, ascorbyl-6-palmitate, stearylamine, sodium lauryl sulfate, polyoxethyleneglycerol triiricinoleate, and any combinations or mixtures thereof; c) anionic surfactants include, but are not limited to, calcium carboxymethylcellulose, sodium carboxymethylcellulose, sodium sulfosuccinate, dioctyl, sodium alginate, alkyl polyoxyethylene sulfates, sodium lauryl sulfate, triethanolamine stearate, potassium laurate, bile salts, and any combinations or mixtures thereof; and d) cationic surfactants such as cetyltrimethylammonium bromide, and lauryldimethylbenzyl-ammonium chloride.

In a further embodiment, when one or more co-surfactants are utilized in the auris-acceptable formulations of the present disclosure, they are combined, e.g., with a pharmaceutically acceptable vehicle and is present in the final formulation, e.g., in an amount ranging from about 0.1% to about 20%, from about 0.5% to about 10%.

In one embodiment, the surfactant has an HLB value of 0 to 20. In additional embodiments, the surfactant has an HLB value of 0 to 3, of 4 to 6, of 7 to 9, of 8 to 18, of 13 to 15, of 10 to 18.

In one embodiment, diluents are also used to stabilize the aural pressure modulating agent or other pharmaceutical compounds because they provide a more stable environment. Salts dissolved in buffered solutions (which also can provide pH control or maintenance) are utilized as diluents, including, but not limited to a phosphate buffered saline solution. In other embodiments, the gel formulation is isotonic with the endolymph or the perilymph: depending on the portion of the cochlea that the aural pressure modulating agent formulation is targeted. Isotonic formulations are provided by the addition of a tonicity agent. Suitable tonicity agents include, but are not limited to any pharmaceutically acceptable sugar, salt or any combinations or mixtures thereof, such as, but not limited to dextrose and sodium chloride. In further embodiments, the tonicity agents are present in an amount from about 100 mOsm/kg to about 500 mOsm/kg. In some embodiments, the tonicity agent is present in an amount from about 200 mOsm/kg to about 400 mOsm/kg, from about 280 mOsm/kg to about 320 mOsm/kg. The amount of tonicity agents will depend on the target structure of the pharmaceutical formulation, as described herein.

Useful tonicity compositions also include one or more salts in an amount required to bring osmolality of the composition into an acceptable range for the perilymph or the endolymph. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some embodiments, the auris-acceptable gel formulations disclosed herein alternatively or additionally contains preservatives to prevent microbial growth. Suitable auris-acceptable preservatives for use in the enhanced viscosity formulations described herein include, but are not limited to benzoic acid, boric acid, p-hydroxybenzoates, alcohols, quarternary compounds, stabilized chlorine dioxide, mercurials, such as merfen and thiomersal, mixtures of the foregoing and the like.

In a further embodiment, the preservative is, by way of example only, an antimicrobial agent, within the auris-acceptable formulations presented herein. In one embodiment, the formulation includes a preservative such as by way of example only, methyl paraben, sodium bisulfite, sodium thiosulfate, ascorbate, chorobutanol, thimerosal, parabens, benzyl alcohol, phenylethanol and others. In another embodiment, the methyl paraben is at a concentration of about 0.05% to about 1.0%, about 0.1% to about 0.2%. In a further embodiment, the gel is prepared by mixing water, methylparaben, hydroxyethylcellulose and sodium citrate. In a further embodiment, the gel is prepared by mixing water, methylparaben, hydroxyethylcellulose and sodium acetate. In a further embodiment, the mixture is sterilized by autoclaving at 120° C. for about 20 minutes, and tested for pH, methylparaben concentration and viscosity before mixing with the appropriate amount of the aural pressure modulating agent disclosed herein.

Suitable auris-acceptable water soluble preservatives which are employed in the drug delivery vehicle include sodium bisulfite, sodium thiosulfate, ascorbate, chorobutanol, thimerosal, parabens, benzyl alcohol, Butylated hydroxytoluene (BHT), phenylethanol and others. These agents are present, generally, in amounts of about 0.001% to about 5% by weight and, preferably, in the amount of about 0.01 to about 2% by weight. In some embodiments, auris-compatible formulations described herein are free of preservatives.

Round Window Membrane Penetration Enhancers

In another embodiment, the formulation further comprises one or more round window membrane penetration enhancers. Penetration across the round window membrane is enhanced by the presence of round window membrane penetration enhancers. Round window membrane penetration enhancers are chemical entities that facilitate transport of coadministered substances across the round window membrane. Round window membrane penetration enhancers are grouped according to chemical structure. Surfactants, both ionic and non-ionic, such as sodium lauryl sulfate, sodium laurate, polyoxyethylene-20-cetyl ether, laureth-9, sodium dodecylsulfate, dioctyl sodium sulfosuccinate, polyoxyethylene-9-lauryl ether (PLE), Tween® 80, nonylphenoxypolyethylene (NP-POE), polysorbates and the like, function as round window membrane penetration enhancers. Bile salts (such as sodium glycocholate, sodium deoxycholate, sodium taurocholate, sodium taurodihydrofusidate, sodium glycodihydrofusidate and the like), fatty acids and derivatives (such as oleic acid, caprylic acid, mono- and di-glycerides, lauric acids, acylcholines, caprylic acids, acylcarnitines, sodium caprates and the like), chelating agents (such as EDTA, citric acid, salicylates and the like), sulfoxides (such as dimethyl sulfoxide (DMSO), decylmethyl sulfoxide and the like), and alcohols (such as ethanol, isopropanol, glycerol, propanediol and the like) also function as round window membrane penetration enhancers.

In some embodiments, the auris acceptable penetration enhancer is a surfactant comprising an alkyl-glycoside wherein the alkyl glycoside is tetradecyl-β-D-maltoside. In some embodiments, the auris acceptable penetration enhancer is a surfactant comprising an alkyl-glycoside wherein the alkyl glycoside is dodecyl-maltoside. In certain instances, the penetration enhancing agent is a hyaluronidase. In certain instances, a hyaluronidase is a human or bovine hyaluronidase. In some instances, a hyaluronidase is a human hyaluronidase (e.g., hyaluronidase found in human sperm, PH20 (Halozyme), Hyelenex® (Baxter International, Inc.)). In some instances, a hyaluronidase is a bovine hyaluronidase (e.g., bovine testicular hyaluronidase, Amphadase® (Amphastar Pharmaceuticals), Hydase® (PrimaPharm, Inc). In some instances, a hyluronidase is an ovine hyaluronidase, Vitrase® (ISTA Pharmaceuticals). In certain instances, a hyaluronidase described herein is a recombinant hyaluronidase. In some instances, a hyaluronidase described herein is a humanized recombinant hyaluronidase. In some instances, a hyaluronidase described herein is a pegylated hyaluronidase (e.g., PEGPH20 (Halozyme)). In addition, the peptide-like penetration enhancers described in U.S. Pat. Nos. 7,151,191, 6,221,367 and 5,714,167, herein incorporated by references for such disclosure, are contemplated as an additional embodiment. These penetration enhancers are amino-acid and peptide derivatives and enable drug absorption by passive transcellular diffusion without affecting the integrity of membranes or intercellular tight junctions.

Round Window Membrane Permeable Liposomes

Liposomes or lipid particles may also be employed to encapsulate the aural pressure modulating agent formulations or compositions. Phospholipids that are gently dispersed in an aqueous medium form multilayer vesicles with areas of entrapped aqueous media separating the lipid layers. Sonication, or turbulent agitation, of these multilayer veiscles results in the formation of single layer vesicles, commonly referred to as liposomes, with sizes of about 10-1000 nm. These liposomes have many advantages as aural pressure modulating agents or other pharmaceutical agent carriers. They are biologically inert, biodegradable, non-toxic and non-antigenic. Liposomes are formed in various sizes and with varying compositions and surface properties. Additionally, they are able to entrap a wide variety of agents and release the agent at the site of liposome collapse.

Suitable phospholipids for use in auris-acceptable liposomes here are, for example, phosphatidyl cholines, ethanolamines and serines, sphingomyelins, cardiolipins, plasmalogens, phosphatidic acids and cerebrosides, in particular those which are soluble together with the aural pressure modulating agents herein in non-toxic, pharmaceutically acceptable organic solvents. Preferred phospholipids are, for example, phosphatidyl choline, phosphatidyl ethanolmine, phosphatidyl serine, phosphatidyl inositol, lysophosphatidyl choline, phosphatidyl glycerol and the like, and mixtures thereof especially lecithin, e.g. soya lecithin. The amount of phospholipid used in the present formulation range from about 10 to about 30%, preferably from about 15 to about 25% and in particular is about 20%.

Lipophilic additives may be employed advantageously to modify selectively the characteristics of the liposomes. Examples of such additives include by way of example only, stearylamine, phosphatidic acid, tocopherol, cholesterol, cholesterol hemisuccinate and lanolin extracts. The amount of lipophilic additive used range from 0.5 to 8%, preferably from 1.5 to 4% and in particular is about 2%. Generally, the ratio of the amount of lipophilic additive to the amount of phospholipid ranges from about 1:8 to about 1:12 and in particular is about 1:10. Said phospholipid, lipophilic additive and the aural pressure modulating agent and other pharmaceutical compounds are employed in conjunction with a non-toxic, pharmaceutically acceptable organic solvent system which dissolve said ingredients. Said solvent system not only must dissolve the aural pressure modulating agent completely, but it also has to allow the formulation of stable single bilayered liposomes. The solvent system comprises dimethylisosorbide and tetraglycol (glycofurol, tetrahydrofurfuryl alcohol polyethylene glycol ether) in an amount of about 8 to about 30%. In said solvent system, the ratio of the amount of dimethylisosorbide to the amount of tetraglycol range from about 2:1 to about 1:3, in particular from about 1:1 to about 1:2.5 and preferably is about 1:2. The amount of tetraglycol in the final composition thus vary from 5 to 20%, in particular from 5 to 15% and preferably is approximately 10%. The amount of dimethylisosorbide in the final composition thus range from 3 to 10%, in particular from 3 to 7% and preferably is approximately 5%.

The term "organic component" as used hereinafter refers to mixtures comprising said phospholipid, lipophilic additives and organic solvents. The aural pressure modulating agent may be dissolved in the organic component, or other means to maintain full activity of the agent. The amount of aural pressure modulating agent in the final formulation may range from 0.1 to 5.0%. In addition, other ingredients such as anti-oxidants may be added to the organic component. Examples include tocopherol, butylated hydroxyanisole, butylated hydroxytoluene, ascorbyl palmitate, ascorbyl oleate and the like.

Liposomal formulations are alternatively prepared, for aural pressure modulating agents or other pharmaceutical agents that are moderately heat-resistant, by (a) heating the phospholipid and the organic solvent system to about 60-80° C. in a vessel, dissolving the active ingredient, then adding any additional formulating agents, and stirring the mixture until complete dissolution is obtained; (b) heating the aqueous solution to 90-95° C. in a second vessel and dissolving the preservatives therein, allowing the mixture to cool and then adding the remainder of the auxiliary formulating agents and the remainder of the water, and stirring the mixture until complete dissolution is obtained; thus preparing the aqueous component; (c) transferring the organic phase directly into the aqueous component, while homogenizing the combination with a high performance mixing apparatus, for example, a high-shear mixer; and (d) adding a viscosity enhancing agent to the resulting mixture while further homogenizing. The aqueous component is optionally placed in a suitable vessel which is equipped with a homogenizer and homogenization is effected by creating turbulence during the injection of the organic component. Any mixing means or homogenizer which exerts high shear forces on the mixture may be employed. Generally, a mixer capable of speeds from about 1,500 to 20,000 rpm, in particular from about 3,000 to about 6,000 rpm may be employed. Suitable viscosity enhancing agents for use in process step (d) are for example, xanthan gum, hydroxypropyl cellulose, hydroxypropyl methylcellulose or mixtures thereof. The amount of viscosity enhancing agent depends on the nature and the concentration of the other ingredients and in general ranges from about 0.5 to 2.0%, or approximately 1.5%. In order to prevent degradation of the materials used during the preparation of the liposomal formulation, it is advantageous to purge all solutions with an inert gas such as nitrogen or argon, and to conduct all steps under an inert atmosphere. Liposomes prepared by the above described method usually contain most of the active ingredient bound in the lipid bilayer and separation of the liposomes from unencapsulated material is not required.

In other embodiments, the auris-acceptable formulations, including gel formulations and viscosity-enhanced formulations, further include excipients, other medicinal or pharmaceutical agents, carriers, adjuvants, such as preserving, stabilizing, wetting or emulsifying agents, solution promoters, salts, solubilizers, an antifoaming agent, an antioxidant, a dispersing agent, a wetting agent, a surfactant, and combinations thereof.

Suitable carriers for use in an auris-acceptable formulation described herein include, but are not limited to, any pharmaceutically acceptable solvent compatible with the targeted auris structure's physiological environment. In other embodiments, the base is a combination of a pharmaceutically acceptable surfactant and solvent.

In some embodiments, other excipients include, sodium stearyl fumarate, diethanolamine cetyl sulfate, isostearate, polyethoxylated castor oil, nonoxyl 10, octoxynol 9, sodium lauryl sulfate, sorbitan esters (sorbitan monolaurate, sorbitan monooleate, sorbitan monopalmitate, sorbitan monostearate, sorbitan sesquioleate, sorbitan trioleate, sorbitan tristearate, sorbitan laurate, sorbitan oleate, sorbitan palmitate, sorbitan stearate, sorbitan dioleate, sorbitan sesqui-isostearate, sorbitan sesquistearate, sorbitan tri-isostearate), lecithin pharmaceutical acceptable salts thereof and combinations or mixtures thereof.

In other embodiments, the carrier is a polysorbate. Polysorbates are nonionic surfactants of sorbitan esters. Polysorbates useful in the present disclosure include, but are not limited to polysorbate 20, polysorbate 40, polysorbate 60, polysorbate 80 (Tween 80) and any combinations or mixtures thereof. In further embodiments, polysorbate 80 is utilized as the pharmaceutically acceptable carrier.

In one embodiment, water-soluble glycerin-based auris-acceptable enhanced viscosity formulations utilized in the preparation of pharmaceutical delivery vehicles comprise at least one aural pressure modulating agent containing at least about 0.1% of the water-soluble glycerin compound or more. In some embodiments, the percentage of aural pressure modulating agent is varied between about 1% and about 95%, between about 5% and about 80%, between about 10% and about 60% or more of the weight or volume of the total pharmaceutical formulation. In some embodiments, the amount of the compound(s) in each therapeutically useful aural pressure modulating agent formulation is prepared in such a way that a suitable dosage will be obtained in any given unit dose of the compound. Factors such as solubility, bioavailability, biological half-life, route of administration, product shelf life, as well as other pharmacological considerations are contemplated herein.

If desired, the auris-acceptable pharmaceutical gels also contain co-solvents, preservatives, cosolvents, ionic strength and osmolality adjustors and other excipeints in addition to buffering agents. Suitable auris-acceptable water soluble buffering agents are alkali or alkaline earth metal carbonates, phosphates, bicarbonates, citrates, borates, acetates, succinates and the like, such as sodium phosphate, citrate, borate, acetate, bicarbonate, carbonate and tromethamine (TRIS). These agents are present in amounts sufficient to maintain the pH of the system at 7.4±0.2 and preferably, 7.4. As such, the buffering agent is as much as 5% on a weight basis of the total composition.

Cosolvents are used to enhance aural pressure modulating agent solubility, however, some aural pressure modulating agents or other pharmaceutical compounds are insoluble. These are often suspended in the polymer vehicle with the aid of suitable suspending or viscosity enhancing agents.

Moreover, some pharmaceutical excipients, diluents or carriers are potentially ototoxic. For example, benzalkonium chloride, a common preservative, is ototoxic and therefore potentially harmful if introduced into the vestibular or cochlear structures. In formulating a controlled release aural pressure modulating agent formulation, it is advised to avoid or combine the appropriate excipients, diluents or carriers to lessen or eliminate potential ototoxic components from the formulation, or to decrease the amount of such excipients, diluents or carriers. Optionally, a controlled release aural pressure modulating agent formulation includes otoprotective agents, such as antioxidants, alpha lipoic acid, calicum, fosfomycin or iron chelators, to counteract potential ototoxic effects that may arise from the use of specific therapeutic agents or excipients, diluents or carriers.

Thof therapeutically acceptable otic formulations:

| Example Formulation | Example Characteristics |
|---|---|
| Chitosan glycerophosphate (CGP) | tunable degradation of matrix in vitro<br>tunable TACE inhibitor release in vitro: e.g., ~50% of drug released after 24 hrs<br>biodegradable<br>compatible with drug delivery to the inner ear<br>suitable for macromolecules and hydrophobic drugs |

| Example Formulation | Example Characteristics |
| --- | --- |
| PEG-PLGA-PEG triblock polymers | tunable high stability: e.g., maintains mechanical integrity >1 month in vitro<br>tunable fast release of hydrophilic drugs: e.g., ~50% of drug released after 24 hrs, and remainder released over ~5 days<br>tunable slow release of hydrophobic drugs: e.g., ~80% released after 8 weeks<br>biodegradable<br>subcutaneous injection of solution: e.g., gel forms within seconds and is intact after 1 month |
| PEO-PPO-PEO triblock copolymers (e.g., Pluronic or Poloxameres) (e.g., F127) | Tunable sol-gel transition temperature: e.g., decreases with increasing F127 concentration |
| Chitosan glycerophosphate with drug-loaded liposomes | CGP formulation tolerates liposomes: e.g., up to 15 uM/ml liposomes.<br>liposomes tunably reduce drug release time (e.g., up to 2 weeks in vitro).<br>increase in liposome diameter optionally reduces drug release kinetics (e.g., liposome size between 100 and 300 nm)<br>release parameters are controlled by changing composition of liposomes |

The formulations disclosed herein alternatively encompass an otoprotectant agent in addition to the at least one active agent and/or excipients, including but not limited to such agents as antioxidants, alpha lipoic acid, calcium, fosfomycin or iron chelators, to counteract potential ototoxic effects that may arise from the use of specific therapeutic agents or excipients, diluents or carriers.

Modes of Treatment

Dosing Methods and Schedules

Drugs delivered to the inner ear have been administered systemically via oral, intravenous or intramuscular routes. However, systemic administration for pathologies local to the inner ear increases the likelihood of systemic toxicities and adverse side effects and creates a non-productive distribution of drug in which high levels of drug are found in the serum and correspondingly lower levels are found at the inner ear.

Intratympanic injection of therapeutic agents is the technique of injecting a therapeutic agent behind the tympanic membrane into the middle and/or inner ear. In one embodiment, the formulations described herein are administered directly onto the round window membrane via transtympanic injection. In another embodiment, the aural pressure modulating agent auris-acceptable formulations described herein are administered onto the round window membrane via a non-transtympanic approach to the inner ear. In additional embodiments, the formulation described herein is administered onto the round window membrane via a surgical approach to the round window membrane comprising modification of the crista fenestrae cochleae.

In one embodiment the delivery system is a syringe and needle apparatus that is capable of piercing the tympanic membrane and directly accessing the round window membrane or crista fenestrae cochleae of the auris interna. In some embodiments, the needle on the syringe is wider than a 18 gauge needle. In another embodiment, the needle gauge is from 18 gauge to 31 gauge. In a further embodiment, the needle gauge is from 25 gauge to 30 gauge. Depending upon the thickness or viscosity of the aural pressure modulating agent compositions or formulations, the gauge level of the syringe or hypodermic needle may be varied accordingly. In another embodiment, the internal diameter of the needle can be increased by reducing the wall thickness of the needle (commonly referred as thin wall or extra thin wall needles) to reduce the possibility of needle clogging while maintaining an adequate needle gauge.

In another embodiment, the needle is a hypodermic needle used for instant delivery of the gel formulation. The hypodermic needle may be a single use needle or a disposable needle. In some embodiments, a syringe may be used for delivery of the pharmaceutically acceptable gel-based aural pressure modulating agent-containing compositions as disclosed herein wherein the syringe has a press-fit (Luer) or twist-on (Luer-lock) fitting. In one embodiment, the syringe is a hypodermic syringe. In another embodiment, the syringe is made of plastic or glass. In yet another embodiment, the hypodermic syringe is a single use syringe. In a further embodiment, the glass syringe is capable of being sterilized. In yet a further embodiment, the sterilization occurs through an autoclave. In another embodiment, the syringe comprises a cylindrical syringe body wherein the gel formulation is stored before use. In other embodiments, the syringe comprises a cylindrical syringe body wherein the aural pressure modulating agent pharmaceutically acceptable gel-based compositions as disclosed herein is stored before use which conveniently allows for mixing with a suitable pharmaceutically acceptable buffer. In other embodiments, the syringe may contain other excipients, stabilizers, suspending agents, diluents or a combination thereof to stabilize or otherwise stably store the aural pressure modulating agent or other pharmaceutical compounds contained therein.

In some embodiments, the syringe comprises a cylindrical syringe body wherein the body is compartmentalized in that each compartment is able to store at least one component of the auris-acceptable aural pressure modulating agent gel formulation. In a further embodiment, the syringe having a compartmentalized body allows for mixing of the components prior to injection into the auris media or auris interna. In other embodiments, the delivery system comprises multiple syringes, each syringe of the multiple syringes contains at least one component of the gel formulation such that each component is pre-mixed prior to injection or is mixed subsequent to injection. In a further embodiment, the syringes disclosed herein comprise at least one reservoir wherein the at least one reservoir comprises an aural pressure modulating agent, or a pharmaceutically acceptable buffer, or a viscosity enhancing agent, such as a gelling agent or a combination thereof. Commercially available injection devices are optionally employed in their simplest form as ready-to-use plastic syringes with a syringe barrel, needle assembly with a needle, plunger with a plunger rod, and holding flange, to perform an intratympanic injection.

In some embodiments, the delivery device is an apparatus designed for administration of therapeutic agents to the middle and/or inner ear. By way of example only: GYRUS Medical Gmbh offers micro-otoscopes for visualization of and drug delivery to the round window niche; Arenberg has described a medical treatment device to deliver fluids to inner ear structures in U.S. Pat. Nos. 5,421,818; 5,474,529; and 5,476,446, each of which is incorporated by reference herein for such disclosure. U.S. patent application Ser. No. 08/874,208, which is incorporated herein by reference for such disclosure, describes a surgical method for implanting a fluid transfer conduit to deliver therapeutic agents to the inner ear. U.S. Patent Application Publication 2007/0167918, which is incorporated herein by reference for such disclosure, further describes a combined otic aspirator and medication dispenser for intratympanic fluid sampling and medicament application.

The formulations described herein, and modes of administration thereof, are also applicable to methods of direct instillation or perfusion of the inner ear compartments. Thus, the formulations described herein are useful in surgical procedures including, by way of non-limiting examples, cochleostomy, labyrinthotomy, mastoidectomy, stapedectomy, endolymphatic sacculotomy or the like.

The auris-acceptable compositions or formulations containing the aural pressure modulating agent compound(s) described herein are administered for prophylactic and/or therapeutic treatments. In therapeutic applications, the aural pressure modulating agent compositions are administered to a patient already suffering from an autoimmune disease, condition or disorder, in an amount sufficient to cure or at least partially arrest the symptoms of the disease, disorder or condition. Amounts effective for this use will depend on the severity and course of the disease, disorder or condition, previous therapy, the patient's health status and response to the drugs, and the judgment of the treating physician.

In the case wherein the patient's condition does not improve, upon the doctor's discretion the administration of the aural pressure modulating agent compounds may be administered chronically, that is, for an extended period of time, including throughout the duration of the patient's life in order to ameliorate or otherwise control or limit the symptoms of the patient's disease or condition.

In the case wherein the patient's status does improve, upon the doctor's discretion the administration of the aural pressure modulating agent compounds may be given continuously; alternatively, the dose of drug being administered may be temporarily reduced or temporarily suspended for a certain length of time (i.e., a "drug holiday"). The length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, and 365 days. The dose reduction during a drug holiday may be from 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's otic conditions has occurred, a maintenance aural pressure modulating agent dose is administered if necessary. Subsequently, the dosage or the frequency of administration, or both, is optionally reduced, as a function of the symptoms, to a level at which the improved disease, disorder or condition is retained. In certain embodiments, patients require intermittent treatment on a long-term basis upon any recurrence of symptoms.

The amount of aural pressure modulating agent that will correspond to such an amount will vary depending upon factors such as the particular compound, disease condition and its severity, according to the particular circumstances surrounding the case, including, e.g., the specific aural pressure modulating agent being administered, the route of administration, the autoimmune condition being treated, the target area being treated, and the subject or host being treated. In general, however, doses employed for adult human treatment will typically be in the range of 0.02-50 mg per administration, preferably 1-15 mg per administration. The desired dose is presented in a single dose or as divided doses administered simultaneously (or over a short period of time) or at appropriate intervals.

In some embodiments, the initial administration is a particular aural pressure modulating agent and the subsequent administration a different formulation or aural pressure modulating agent.

Pharmacokinetics of Controlled Release Formulations

In one embodiment, the formulations disclosed herein additionally provides an immediate release of an aural pressure modulating agent from the composition, or within 1 minute, or within 5 minutes, or within 10 minutes, or within 15 minutes, or within 30 minutes, or within 60 minutes or within 90 minutes. In other embodiments, a therapeutically effective amount of at least one aural pressure modulating agent is released from the composition immediately, or within 1 minute, or within 5 minutes, or within 10 minutes, or within 15 minutes, or within 30 minutes, or within 60 minutes or within 90 minutes. In certain embodiments the composition comprises an auris-pharmaceutically acceptable gel formulation providing immediate release of at least one aural pressure modulating agent. Additional embodiments of the formulation may also include an agent that enhances the viscosity of the formulations included herein.

In other or further embodiments, the formulation provides an extended release formulation of at least one aural pressure modulating agent. In certain embodiments, diffusion of at least one aural pressure modulating agent from the formulation occurs for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year. In other embodiments, a therapeutically effective amount of at least one aural pressure modulating agent is released from the formulation for a time period exceeding 5 minutes, or 15 minutes, or 30 minutes, or 1 hour, or 4 hours, or 6 hours, or 12 hours, or 18 hours, or 1 day, or 2 days, or 3 days, or 4 days, or 5 days, or 6 days, or 7 days, or 10 days, or 12 days, or 14 days, or 18 days, or 21 days, or 25 days, or 30 days, or 45 days, or 2 months or 3 months or 4 months or 5 months or 6 months or 9 months or 1 year.

In other embodiments, the formulation provides both an immediate release and an extended release formulation of an aural pressure modulating agent. In yet other embodiments, the formulation contains a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations. In a further embodiment the formulation provides an immediate release of a first aural pressure modulating agent and an extended release of a second aural pressure modulating agent or other therapeutic agent. In yet other embodiments, the formulation provides an immediate release and extended release formulation of at least one aural pressure modulating agent, and at least one therapeutic agent. In some embodiments, the formulation provides a 0.25:1 ratio, or a 0.5:1 ratio, or a 1:1 ratio, or a 1:2 ratio, or a 1:3, or a 1:4 ratio, or a 1:5 ratio, or a 1:7 ratio, or a 1:10 ratio, or a 1:15 ratio, or a 1:20 ratio of immediate release and extended release formulations of a first aural pressure modulating agent and second therapeutic agent, respectively.

In a specific embodiment the formulation provides a therapeutically effective amount of at least one aural pressure modulating agent at the site of disease with essentially no systemic exposure. In an additional embodiment the formulation provides a therapeutically effective amount of at least one aural pressure modulating agent at the site of disease with essentially no detectable systemic exposure. In other embodiments, the formulation provides a therapeutically effective amount of at least one aural pressure modulating agent at the site of disease with little or no detectable systemic exposure.

The combination of immediate release, delayed release and/or extended release aural pressure modulating agent compositions or formulations may be combined with other pharmaceutical agents, as well as the excipients, diluents, stabilizers, tonicity agents and other components disclosed herein. As such, depending upon the aural pressure modulating agent used, the thickness or viscosity desired, or the mode of delivery chosen, alternative aspects of the embodiments disclosed herein are combined with the immediate release, delayed release and/or extended release embodiments accordingly.

In certain embodiments, the pharmacokinetics of the aural pressure modulating agent formulations described herein are determined by injecting the formulation on or near the round window membrane of a test animal (including by way of example, a guinea pig or a chinchilla). At a determined period of time (e.g., 6 hours, 12 hours, 1 day, 2 days, 3 days, 4 days, 5 days, 6 days, and 7 days for testing the pharmacokinetics of a formulation over a 1 week period), the test animal is euthanized and a 5 mL sample of the perilymph fluid is tested. The inner ear removed and tested for the presence of the aural pressure modulating agent. As needed, the level of aural pressure modulating agent is measured in other organs. In addition, the systemic level of the aural pressure modulating agent is measured by withdrawing a blood sample from the test animal. In order to determine whether the formulation impedes hearing, the hearing of the test animal is optionally tested.

Alternatively, an inner ear is provided (as removed from a test animal) and the migration of the aural pressure modulating agent is measured. As yet another alternative, an in vitro model of a round window membrane is provided and the migration of the aural pressure modulating agent is measured.

Kits/Articles of Manufacture

The disclosure also provides kits for preventing, treating or ameliorating the symptoms of a disease or disorder in a mammal. Such kits generally will comprise one or more of the aural pressure modulating agent controlled-release compositions or devices disclosed herein, and instructions for using the kit. The disclosure also contemplates the use of one or more of the aural pressure modulating agent controlled-release compositions, in the manufacture of medicaments for treating, abating, reducing, or ameliorating the symptoms of a disease, dysfunction, or disorder in a mammal, such as a human that has, is suspected of having, or at risk for developing an inner ear disorder.

In some embodiments, kits include a carrier, package, or container that is compartmentalized to receive one or more containers such as vials, tubes, and the like, each of the container(s) including one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products are also presented herein. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of aural pressure modulating agent formulations compositions provided herein are contemplated as are a variety of treatments for any disease, disorder, or condition that would benefit by controlled release administration of a aural pressure modulating agent to the inner ear.

In some embodiments, a kit includes one or more additional containers, each with one or more of various materials (such as reagents, optionally in concentrated form, and/or devices) desirable from a commercial and user standpoint for use of a formulation described herein. Non-limiting examples of such materials include, but not limited to, buffers, diluents, filters, needles, syringes; carrier, package, container, vial and/or tube labels listing contents and/or instructions for use and package inserts with instructions for use. A set of instructions is optionally included. In a further embodiment, a label is on or associated with the container. In yet a further embodiment, a label is on a container when letters, numbers or other characters forming the label are attached, molded or etched into the container itself; a label is associated with a container when it is present within a receptacle or carrier that also holds the container, e.g., as a package insert. In other embodiments a label is used to indicate that the contents are to be used for a specific therapeutic application. In yet another embodiment, a label also indicates directions for use of the contents, such as in the methods described herein.

In certain embodiments, the pharmaceutical compositions are presented in a pack or dispenser device which contains one or more unit dosage forms containing a compound provided herein. In another embodiment, the pack for example contains metal or plastic foil, such as a blister pack. In a further embodiment, the pack or dispenser device is accompanied by instructions for administration. In yet a further embodiment, the pack or dispenser is also accompanied with a notice associated with the container in form prescribed by a governmental agency regulating the manufacture, use, or sale of pharmaceuticals, which notice is reflective of approval by the agency of the form of the drug for human or veterinary administration. In another embodiment, such notice, for example, is the labeling approved by the U.S. Food and Drug Administration for prescription drugs, or the approved product insert. In yet another embodiment, compositions containing a compound provided herein formulated in a compatible pharmaceutical carrier are also prepared, placed in an appropriate container, and labeled for treatment of an indicated condition.

EXAMPLES

Example 1—Preparation of a Thermoreversible Gel VP2 Antagonist Formulation

| Ingredient | Quantity (mg/g of formulation) |
|---|---|
| Lixivaptan | 20.00 |
| methylparaben | 1.0 |
| HPMC | 10.0 |
| Poloxamer 407 | 180.0 |
| TRIS HCl buffer (0.1M) | 789.0 |

A 10-g batch of gel formulation containing 2.0% of lixivaptan is prepared by suspending 1.80 g of Poloxamer 407 (BASF Corp.) in 5.00 g of TRIS HCl buffer (0.1 M) and the components are mixed under agitation overnight at 4° C. to ensure complete dissolution. The lixivaptan (200.0 mg), hydroxypropylmethylcellulose (100.0 mg), methylparaben (10 mg) and additional TRIS HCl buffer (0.1 M) (2.89 g) is added and further stirring allowed until complete dissolution is observed. The mixture is maintained below room temperature until use.

Example 2—Preparation of Liposomal VP2 Antagonist Formation

| Ingredient | Quantity (mg/g of cream) |
|---|---|
| Lixivaptan | 5.0 |
| soya lecithin | 200.0 |
| cholesterol | 20.0 |
| tetraglycol | 100.0 |
| dimethylisosorbide | 50.0 |
| methylparaben | 2.0 |
| propylparaben | 0.2 |
| BHT | 0.1 |
| sodium chloride | 1.0 |
| HPMC | 15.0 |
| sodium hydroxide | 0.6 |
| citric acid | 1.0 |
| purified water, USP | 603.6 |

Heat the soya lecithin, tetraglycol and dimethyl isosorbide to about 70-75° C. Dissolve the lixivaptan, cholesterol and butylated hydroxytoluene in the heated mixture. Stir until complete dissolution is obtained. Heat about one third of the water to 80-95° C. in a separate vessel and dissolve the preservatives methylparaben and propylparaben in the heated water while stirring. Allow the solution to cool to about 25° C. and then add the disodium edetate, sodium chloride, sodium hydroxide and citric acid. Add the remainder of the water and stir to obtain a complete solution. Transfer the organic mixture into the aqueous mixture by means of a vacuum, while homogenizing the combination with a high-shear mixer until a homogeneous product is obtained. Add the hydroxypropyl methylcellulose into the biphasic mixture by means of a vacuum while homogenizing with a mixer. The homogenizer is a Silverson high-shear mixer operating at approximately 3000 rpm. Single bilayered liposomes are formed. The white lipogel cream is ready for use.

Example 3—Preparation of a VP2 Antagonist Nanoparticle Formulation 750 mg (15 mg/ml theoretical) of a diblock copolymer consisting of the combination of a poly(d,l-lactic acid) of mass 30 kD and of a polyethylene glycol of mass 2 kD (PLA-PEG) and 250 mg (5 mg/ml theoretical) of tolvaptan is dissolved in 20 ml of ethyl acetate (solution A). 175 mg of lecithin E80 and 90 mg of sodium oleate is dispersed in 50 ml of 5% w/v glucose solution (solution B). Solution A is emulsified in solution B with an Ultra-turrax stirrer and the pre-emulsion is then introduced into a Microfluidizer 110 S.®. type homogenizer for 10 minutes at 10° C. The volume of emulsion recovered is about 70 ml (70 g). The ethyl acetate is removed using a rotary evaporator at reduced pressure (100 mm of mercury) to a suspension volume of about 45 ml (45 g).

Example 4—Preparation of a 5% Cyclodextrin VP2 Antagonist Formulation

To a suitable 150 mL glass vessel is added tolvaptan (5.0 g), sterile 2% dibasic sodium phosphate dodecahydrate solution (9.0 g) and Hydroxypropyl-®-cyclodextrin (50 g). The resulting mixture is stirred until a clear solution is formed. To this solution is added sterile 2% polysorbate 80 solution (5 g), sterile 2% stock HPMC 2910 (E4M) solution (2.5 g) and 5% sterile sodium chloride solution (11 g), and stirring is continued until homogeneous. Sterile water for injection is added to get to 95% of batch size. The solution is stirred at rt for 30 min and pH is adjusted to 7.2. Finally, water for injection is added to get a final batch size of 100 g.

Example 5—Preparation of a Mucoadhesive, Thermoreversible Gel VP2 Antagonist Formulation

| Ingredient | Quantity (mg/g of formulation) |
|---|---|
| SR-121463 | 20.0 |
| methylparaben | 1.0 |
| HPMC | 10.0 |
| Carbopol 934P | 2.0 |
| Poloxamer 407 | 180.0 |
| TRIS HCl buffer (0.1M) | 787.0 |

A 10-g batch of mucoadhesive, gel formulation containing 2.0% of SR-121463 is prepared by suspending 2.0 mg of Carbopol 934P and 1.80 g of Poloxamer 407 (BASF Corp.) in 5.00 g of TRIS HCl buffer (0.1 M) and the components are mixed under agitation overnight at 4° C. to ensure complete dissolution. The SR-121463 (200.0 mg), hydroxypropylmethylcellulose (100.0 mg), methylparaben (10 mg) and additional TRIS HCl buffer (0.1 M) (2.87 g) are added and further stirring allowed until complete dissolution is observed. The mixture is maintained below room temperature until use.

Example 6—Preparation of a 50% VP2 Antagonist 95:5 d,l-PLGA Microsphere Formulation Twenty-five grams (25 g) of 95:5 d,l-PLGA and 25 g of OPC-31260 are codissolved in 196 g ethyl acetate in an Erlemeyer flask at 52° C. The drug/polymer solution is added to a 1000 ml glass jacketed reactor containing 550 g of 5% aqueous polyvinyl alcohol containing 9.7 g of ethyl acetate. Reactor contents are stirred with an overhead stir motor and the temperature is maintained at 52° C. by a circulating bath. The emulsion size is monitored by light microscopy and the stirring is stopped when the particle size is found to be in the desired size range (less than 300 microns), usually after about 2 minutes. The stir speed is reduced to avoid further size reduction of the sterilized emulsion. After stirring for a total of 4 minutes, the reactor contents are pressure-transferred into 40 liters of water at 12° C. After stirring for 20 minutes, the hardened microspheres are isolated and the product then transferred into 20 liters of water at 12° C. After approximately 3 hours, the second wash is transferred onto a sieve stack composed of 25, 45, 90, 150, and 212 micron openings. The product on the sieves is washed with copious amounts of cold water to separate the different sizes of microspheres. After drying on the sieves overnight, the different fractions are collected and drying was continued under vacuum at room temperature. Formulations with other drug levels are prepared by simply adjusting the polymer/drug ratio.

Example 7—Preparation of a 50% VP2 Antagonist 65:35 d,l-PLGA Microsphere Formulation Microspheres were produced by the method of Example 6 except that a different biodegradable polymer matrix was utilized. A 65:35 d,l-PLGA polymer was used in place of the 95:5 polymer indicated in Example 6.

Example 8—Preparation of a Mucoadhesive, Cyclodextrin-based VP2 Antagonist Formulation

| Ingredient | Quantity (mg/g of formulation) |
|---|---|
| Lixivaptan | 20.0 |
| HP ® CD | 500 |
| propylene glycol | 50 |
| paraffin oil | 200 |
| trihydroxystearate | 10 |
| cetyl dimethicon copolyol | 30 |
| water | qs ad 1000 |
| phosphate buffer pH 7.4 | qs pH 7.4 |

The cream-type formulation is prepared by solubilizing lixivaptan with propylene glycol and this solution is added to a suspension of HP®CD in water. A second system is prepared by mixing paraffin oil, trihydroxystearate and cetyl dimethicon copolyol with warming to 60° C. Upon cooling to room temperature, the lipid system is mixed with the aqueous phase in a homogenizer for 30 minutes.

Example 9—Preparation of a Cyclodextrin-containing Thermoreversible Gel 2.5% VP2 Antagonist Formulation

| Ingredient | Quantity (mg/g of formulation) |
|---|---|
| 5% CD solution | 500.0 |
| methylparaben | 1.0 |
| Poloxamer 407 | 180.0 |
| TRIS HCl buffer (0.1M) | 317.0 |

The Poloxamer 407 (BASF Corp.) is suspended in the TRIS HCl buffer (0.1 M) and the components are mixed under agitation overnight at 4° C. to ensure complete dissolution. The cyclodextrin solution from Example 4 and methylparaben is added and further stirring allowed until complete dissolution is observed. The mixture is maintained below room temperature until use.

Example 10—Preparation of a Cyclodextrin-containing Mucoadhesive, Thermoreversible Gel VP2 Antagonist Formulation

| Ingredient | Quantity (mg/g of formulation) |
|---|---|
| 5% CD solution | 500.0 |
| methylparaben | 1.0 |
| Poloxamer 407 | 180.0 |
| Carbopol 934P | 2.0 |
| TRIS HCl buffer (0.1M) | 317.0 |

The Carbopol 934P and Poloxamer 407 (BASF Corp.) is suspended in the TRIS HCl buffer (0.1 M) and the components are mixed under agitation overnight at 4° C. to ensure complete dissolution. The cyclodextrin solution from Example 4 and methylparaben is added and further stirring allowed until complete dissolution is observed. The mixture is maintained below room temperature until use.

Example 11—Preparation of a Gel VP2 Antagonist Formulation

| Ingredient | Quantity (mg/g of formulation) |
|---|---|
| SR-121463 | 20.0 |
| chitosan | 20.0 |
| Glycerophosphate disodium | 80.0 |
| water | 880 |

A 5 ml solution of acetic acid is titrated to a pH of about 4.0. The chitosan is added to achieve a pH of about 5.5. The SR-121463 is then dissolved in the chitosan solution. This solution is sterilized by filtration. A 5 ml aqueous solution of glycerophosphate disodium is also prepared and sterilized. The two solutions are mixed and within 2 h at 37° C., the desired gel is formed.

Example 12—Preparation of a Gel/Liposome VP2 Antagonist Formulation

| Ingredient | Quantity |
|---|---|
| SR-121463 | 20.0 mg/g |
| Liposomes | 15 umol/ml |
| Chitosan-Glycerophosphate | 100.0 mg/g |

The liposomes are prepared in the presence of the VP2 antagonist SR-121463 by the reversed-phase evaporation method, where lipids in chloroform or chloroform-methanol (2:1, v/v) are deposited on the sides of a tube by evaporation of the organic solvent. The lipid film is redissolved in diethyl ether and the aqueous phase (pH 7.4 300 mOsm/kg) containing 20 mM Hepes and 144 mM NaCl is added. The mixture is sonicated to obtain a homogeneous emulsion, and then the organic solvent is removed under vacuum. The preparation is extruded to obtain the required liposome size and free components removed by size-exclusion chromatography using a Sephadex G-50 column (Amersham Pharmacia Biotech, Uppsala, Sweden).

To prepare the chitosan-glycerophosphate formulation, a 5 ml solution of acetic acid is titrated to a pH of about 4.0. The chitosan is added to achieve a pH of about 5.5. This solution is sterilized by filtration. A 5 ml aqueous solution of glycerophosphate disodium is also prepared and sterilized. The two solutions are mixed and within 2 h at 37° C., and the desired gel is formed. The chitosan-glycerophosphate solution is gently mixed with the liposomes at room temperature.

Example 13—Effect of pH on Degradation Products for Autoclaved 17% Poloxamer 407NF/2% Otic Agent in PBS Buffer A stock solution of a 17% poloxamer 407/2% otic agent is prepared by dissolving 351.4 mg of sodium chloride (Fisher Scientific), 302.1 mg of sodium phosphate dibasic anhydrous (Fisher Scientific), 122.1 mg of sodium phosphate monobasic anhydrous (Fisher Scientific) and an appropriate amount of an otic agent with 79.3 g of sterile filtered DI water. The solution is cooled down in a ice chilled water bath and then 17.05 g of poloxamer 407NF (SPECTRUM CHEMICALS) is sprinkled into the cold solution while mixing. The mixture is further mixed until the poloxamer is completely dissolved. The pH for this solution is measured.

17% Poloxamer 407/2% Otic Agent in PBS pH of 5.3.

Take an aliquot (approximately 30 mL) of the above solution and adjust the pH to 5.3 by the addition of 1 M HCl.

17% Poloxamer 407/2% Otic Agent in PBS pH of 8.0.

Take an aliquot (approximately 30 mL) of the above stock solution and adjust the pH to 8.0 by the addition of 1 M NaOH.

A PBS buffer (pH 7.3) is prepared by dissolving 805.5 mg of sodium chloride (Fisher Scientific), 606 mg of sodium phosphate dibasic anhydrous (Fisher Scientific), 247 mg of sodium phosphate monobasic anhydrous (Fisher Scientific), then QS to 200 g with sterile filtered DI water.

A 2% solution of an otic agent in PBS pH 7.3 is prepared by dissolving an appropriate amount of the otic agent in the PBS buffer and QS to 10 g with PBS buffer.

One mL samples are individually placed in 3 mL screw cap glass vials (with rubber lining) and closed tightly. The vials are placed in a Market Forge-sterilmatic autoclave (settings, slow liquids) and sterilized at 250° F. for 15 minutes. After the autoclave the samples are left to cool down to room temperature and then placed in refrigerator. The samples are homogenized by mixing the vials while cold.

Appearance (e.g., discoloration and/or precipitation) is observed and recorded. HPLC analysis is performed using an Agilent 1200 equipped with a Luna C18(2) 3 µm, 100 Å, 250×4 6 mm column) using a 30-80 acetonitrile gradient (1-10 min) of (water-acetonitrile mixture containing 0.05% TFA), for a total run of 15 minutes. Samples are diluted by taking 30 µL of sample and dissolved with 1.5 mL of a 1:1 acetonitrile water mixture. Purity of the otic agent in the autoclaved samples is recorded.

In general the formulation should not have any individual impurity (e.g., degradation product of otic agent) of more than 2% and more preferably not more than one percent. In addition, the formulation should not precipitate during storage or change in color after manufacturing and storage.

Formulations comprising conivaptan, SR-121463 or micronized lixivaptan, prepared according to the procedure above, are tested using the above procedure to determine the effect of pH on degradation during the autoclaving step.

Example 14—Effect of Autoclaving on the Release Profile and Viscosity of a 17% Poloxamer 407NF/2% Otic Agent in PBS An aliquot of a sample (autoclaved and not autoclaved) is evaluated for release profile and viscosity measurement to evaluate the impact of heat sterilization on the properties of the gel.

Dissolution is performed at 37° C. in snapwells (6.5 mm diameter polycarbonate membrane with a pore size of 0.4 µm). 0.2 mL of gel is placed into snapwell and left to harden, then 0.5 mL is placed into reservoir and shaken using a Labline orbit shaker at 70 rpm. Samples are taken every hour (0.1 mL withdrawn and replace with warm buffer). Samples are analyzed for poloxamer concentration by UV at 624 nm using the cobalt thiocyanate method, against an external calibration standard curve. In brief, 20 µL of the sample is mixed with 1980 µL of a 15 mM cobalt thiocyanate solution and absorbance measured at 625 nm, using a Evolution 160 UV/Vis spectrophotometer (Thermo Scientific).

The released otic agent is fitted to the Korsmeyer-Peppas equation $$\frac{Q}{Q_x} = kt^n + b$$

where Q is the amount of otic agent released at time t, $Q_\alpha$ is the overall released amount of otic agent, k is a release constant of the nth order, n is a dimensionless number related to the dissolution mechanism and b is the axis intercept, characterizing the initial burst release mechanism wherein n=1 characterizes an erosion controlled mechanism. The mean dissolution time (MDT) is the sum of different periods of time the drug molecules stay in the matrix before release, divided by the total number of molecules and is calculated by:

$$MDT = \frac{nk^{\frac{-1}{n}}}{n+1}$$

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min) Tgel is defined as the inflection point of the curve where the increase in viscosity occurs due to the sol-gel transition.

Formulations comprising conivaptan, SR-121463 or micronized lixivaptan prepared according to the procedures described above, are tested using the procedure described above to determine Tgel.

Example 15—Effect of Addition of a Secondary Polymer on the Degradation Products and Viscosity of a Formulation Containing 2% Otic Agent and 17% Poloxamer 407NF after Heat Sterilization (Autoclaving)

Solution A.

A solution of pH 7.0 comprising sodium carboxymethylcellulose (CMC) in PBS buffer is prepared by dissolving 178.35 mg of sodium chloride (Fisher Scientific), 300.5 mg of sodium phosphate dibasic anhydrous (Fisher Scientific), 126.6 mg of sodium phosphate monobasic anhydrous (Fisher Scientific) dissolved with 78.4 of sterile filtered DI water, then 1 g of Blanose 7M65 CMC (Hercules, viscosity of 5450 cP @ 2%) is sprinkled into the buffer solution and heated to aid dissolution, and the solution is then cooled down.

A solution of pH 7.0 comprising 17% poloxamer 407NF/ 1% CMC/2% otic agent in PBS buffer is made by cooling down 8.1 g of solution A in a ice chilled water bath and then adding an appropriate amount of an otic agent followed by mixing. 1.74 g of poloxamer 407NF (Spectrum Chemicals) is sprinkled into the cold solution while mixing. The mixture is further mixed until all the poloxamer is completely dissolved.

Two mL of the above sample is placed in a 3 mL screw cap glass vial (with rubber lining) and closed tightly. The vial is placed in a Market Forge-sterilmatic autoclave (settings, slow liquids) and sterilized at 250° F. for 25 minutes. After autoclaving the sample is left to cool down to room temperature and then placed in refrigerator. The sample is homogenized by mixing while the vials are cold.

Precipitation or discoloration are observed after autoclaving. HPLC analysis is performed using an Agilent 1200 equipped with a Luna C18(2) 3 μm, 100 Å, 250×4 6 mm column) using a 30-80 acetonitrile gradient (1-10 min) of (water-acetonitrile mixture containing 0.05% TFA), for a total run of 15 minutes. Samples are diluted by taking 30 μL of sample and dissolving with 1.5 mL of a 1:1 acetonitrile water mixture. Purity of the otic agent in the autoclaved samples is recorded.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min) Tgel is defined as the inflection point of the curve where the increase in viscosity occurs due to the sol-gel transition.

Dissolution is performed at 37° C. for the non-autoclaved sample in snapwells (6.5 mm diameter polycarbonate membrane with a pore size of 0.4 μM), 0.2 mL of gel is placed into snapwell and left to harden, then 0.5 mL is placed into reservoir and shaken using a Labline orbit shaker at 70 rpm. Samples are taken every hour (0.1 mL withdrawn and replaced with warm buffer). Samples are analyzed for otic agent concentration by UV at 245 nm, against an external calibration standard curve.

Formulations comprising conivaptan, SR-121463 or micronized lixivaptan are tested using the above procedure to determine the effect addition of a secondary polymer on the degradation products and viscosity of a formulation containing 2% otic agent and 17% poloxamer 407NF after heat sterilization (autoclaving).

Example 16—Effect of Buffer Type on the Degradation Products for Formulations Containing Poloxamer 407NF after Heat Sterilization (Autoclaving)

A TRIS buffer is made by dissolving 377.8 mg of sodium chloride (Fisher Scientific), and 602.9 mg of Tromethamine (Sigma Chemical Co.) then QS to 100 g with sterile filtered DI water, pH is adjusted to 7.4 with 1M HCl.

Stock Solution Containing 25% Poloxamer 407 Solution in TRIS Buffer:

Weigh 45 g of TRIS buffer, chill in an ice chilled bath then sprinkle into the buffer, while mixing, 15 g of poloxamer 407 NF (Spectrum Chemicals). The mixture is further mixed until all the poloxamer is completely dissolved.

A series of formulations is prepared with the above stock solution. An appropriate amount of otic agent (or salt or prodrug thereof) and/or otic agent as micronized/coated/ liposomal particles (or salt or prodrug thereof) is used for all experiments.

Stock Solution (pH 7.3) Containing 25% Poloxamer 407 Solution in PBS Buffer:

PBS buffer described above is used. Dissolve 704 mg of sodium chloride (Fisher Scientific), 601.2 mg of sodium phosphate dibasic anhydrous (Fisher Scientific), 242.7 mg of sodium phosphate monobasic anhydrous (Fisher Scientific) with 140.4 g of sterile filtered DI water. The solution is cooled down in an ice chilled water bath and then 50 g of poloxamer 407NF (SPECTRUM CHEMICALS) is sprinkled into the cold solution while mixing. The mixture is further mixed until the poloxamer is completely dissolved.

A series of formulations is prepared with the above stock solution. An appropriate amount of otic agent (or salt or prodrug thereof) and/or otic agent as micronized/coated/ liposomal particles (or salt or prodrug thereof) is used for all experiments.

Tables 2 and 3 list samples prepared using the procedures described above. An appropriate amount of otic agent is added to each sample to provide a final concentration of 2% otic agent in the sample.

TABLE 2

Preparation of samples containing TRIS buffer

| Sample | pH | 25% Stock Solution (g) | TRIS Buffer (g) |
|---|---|---|---|
| 20% P407/2 otic agent/TRIS | 7.45 | 8.01 | 1.82 |
| 18% P407/2 otic agent/TRIS | 7.45 | 7.22 | 2.61 |
| 16% P407/2 otic agent/TRIS | 7.45 | 6.47 | 3.42 |
| 18% P4072 otic agent/TRIS | 7.4 | 7.18 | 2.64 |
| 4% otic agent/TRIS | 7.5 | — | 9.7 |
| 2% otic agent /TRIS | 7.43 | — | 5 |
| 1% otic agent /TRIS | 7.35 | — | 5 |
| 2% otic agent /TRIS (suspension) | 7.4 | — | 4.9 |

TABLE 3

Preparation of samples containing PBS buffer (pH of 7.3)

| Sample | 25% Stock Solution in PBS (g) | PBS Buffer (g) |
|---|---|---|
| 20% P407/2 otic agent/PBS | 8.03 | 1.82 |
| 18% P407/2 otic agent/PBS | 7.1 | 2.63 |
| 16% P407/2 otic agent/PBS | 6.45 | 3.44 |
| 18% P407/2 otic agent/PBS | — | 2.63 |
| 2% otic agent/PBS | — | 4.9 |

One mL samples are individually placed in 3 mL screw cap glass vials (with rubber lining) and closed tightly. The vials are placed in a Market Forge-sterilmatic autoclave (setting, slow liquids) and sterilized at 250° F. for 25 minutes. After the autoclaving the samples are left to cool down to room temperature. The vials are placed in the refrigerator and mixed while cold to homogenize the samples.

HPLC analysis is performed using an Agilent 1200 equipped with a Luna C18(2) 3 μm, 100 Å, 250×4.6 mm column) using a 30-80 acetonitrile gradient (1-10 min) of (water-acetonitrile mixture containing 0.05% TFA), for a total run of 15 minutes. Samples are diluted by taking 30 μL of sample and dissolving with 1.5 mL of a 1:1 acetonitrile water mixture. Purity of the otic agent in the autoclaved samples is recorded. The stability of formulations in TRIS and PBS buffers is compared.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min) Tgel is defined as the inflection point of the curve where the increase in viscosity occurs due to the sol-gel transition. Only formulations that show no change after autoclaving are analyzed.

Formulations comprising conivaptan, SR-121463 or micronized lixivaptan are tested using the above procedure to determine the effect addition of a secondary polymer on the degradation products and viscosity of a formulation containing 2% otic agent and 17% poloxamer 407NF after heat sterilization (autoclaving). Stability of formulations containing micronized otic agent is compared to non-micronized otic agent formulation counterparts.

Example 17—Pulsed Release Otic Formulations a combination of SR-121463 and SR-121463 hydrochloride (ratio of 1:1) is used to prepare a pulsed release otic agent formulation using the procedures described herein. 20% of the delivered dose of SR-121463 is solubilized in a 17% poloxamer solution of example 13 with the aid of beta-cyclodextrins. The remaining 80% of the otic agent is then added to the mixture and the final formulation is prepared using any procedure described herein.

Pulsed release formulations comprising conivaptan, SR-121463 or micronized lixivaptan prepared according to the procedures and examples described herein, are tested using procedures described herein to determine pulse release profiles.

Example 18—Preparation of a 17% Poloxamer 407/2% Otic Agent/78 ppm Evans Blue in Pbs A Stock solution of Evans Blue (5.9 mg/mL) in PBS buffer is prepared by dissolving 5.9 mg of Evans Blue (Sigma Chemical Co) with 1 mL of PBS buffer (from example 13).

A Stock solution containing 25% Poloxamer 407 solution in PBS buffer is used in this study. An appropriate amount of an otic agent is added to the stock solution to prepare formulations comprising 2% of an otic agent (Table 4).

TABLE 4

Preparation of poloxamer 407 samples containing Evans Blue

| Sample ID | 25% P407 in PBS (g) | PBS Buffer (g) | Evans Blue Solution (μL) |
|---|---|---|---|
| 17% P407/2 otic agent/EB | 13.6 | 6 | 265 |
| 20% P407/2 otic agent/EB | 16.019 | 3.62 | 265 |
| 25% P407/2 otic agent/EB | 19.63 | — | 265 |

Formulations comprising conivaptan, SR-121463 or micronized lixivaptan are prepared according to the procedures described above and are sterile filtered through 0.22 μm PVDF syringe filters (Millipore corporation), and autoclaved.

The above formulations are dosed to guinea pigs in the middle ear by procedures described herein and the ability of formulations to gel upon contact and the location of the gel is identified after dosing and at 24 hours after dosing.

Example 19—Terminal Sterilization of Poloxamer 407 Formulations with and without a Visualization Dye 17% Poloxamer407/2% Otic Agent/in Phosphate Buffer, pH 7.3:

Dissolve 709 mg of sodium chloride (Fisher Scientific), 742 mg of sodium phosphate dibasic dehydrate USP (Fisher Scientific), 251.1 mg of sodium phosphate monobasic monohydrate USP (Fisher Scientific) and an appropriate amount of an otic agent with 158.1 g of sterile filtered DI water. The solution is cooled down in an ice chilled water bath and then 34.13 g of poloxamer 407NF (Spectrum chemicals) is sprinkled into the cold solution while mixing. The mixture is further mixed until the poloxamer is completely dissolved.

17% Poloxamer407/2% Otic Agent/59 ppm Evans Blue in Phosphate Buffer:

Take two mL of the 17% poloxamer407/2% otic agent/in phosphate buffer solution and add 2 mL of a 5.9 mg/mL Evans blue (Sigma-Aldrich chemical Co) solution in PBS buffer.

25% Poloxamer407/2% Otic Agent/in Phosphate Buffer:

Dissolve 330.5 mg of sodium chloride (Fisher Scientific), 334.5 mg of sodium phosphate dibasic dehydrate USP (Fisher Scientific), 125.9 mg of sodium phosphate monobasic monohydrate USP (Fisher Scientific) and an appropriate amount of an otic agent with 70.5 g of sterile filtered DI water.

The solution is cooled down in an ice chilled water bath and then 25.1 g of poloxamer 407NF (Spectrum chemicals) is sprinkled into the cold solution while mixing. The mixture is further mixed until the poloxamer is completely dissolved.

25% Poloxamer407/2% Otic Agent/59 ppm Evans Blue in Phosphate Buffer:

Take two mL of the 25% poloxamer407/2% otic agent/in phosphate buffer solution and add 2 mL of a 5.9 mg/mL Evans blue (Sigma-Aldrich chemical Co) solution in PBS buffer.

Place 2 mL of formulation into a 2 mL glass vial (Wheaton serum glass vial) and seal with 13 mm butyl str (kimble stoppers) and crimp with a 13 mm aluminum seal. The vials are placed in a Market Forge-sterilmatic autoclave (settings, slow liquids) and sterilized at 250° F. for 25 minutes. After the autoclaving the samples are left to cool down to room temperature and then placed in refrigeration. The vials are placed in the refrigerator and mixed while cold to homogenize the samples. Sample discoloration or precipitation after autoclaving is recorded.

HPLC analysis is performed using an Agilent 1200 equipped with a Luna C18(2) 3 μm, 100 Å, 250×4.6 mm column) using a 30-95 methanol:acetate buffer pH 4 gradient (1-6 min), then isocratic for 11 minutes, for a total run of 22 minutes. Samples are diluted by taking 30 μL of sample and dissolved with 0.97 mL of water. The main peaks are recorded in the table below. Purity before autoclaving is always greater than 99% using this method.

Viscosity measurements are performed using a Brookfield viscometer RVDV-II+P with a CPE-51 spindle rotated at 0.08 rpm (shear rate of 0.31 s$^{-1}$), equipped with a water jacketed temperature control unit (temperature ramped from 15-34° C. at 1.6° C./min) Tgel is defined as the inflection point of the curve where the increase in viscosity occurs due to the sol-gel transition.

Formulations comprising conivaptan, SR-121463 or micronized lixivaptan prepared according to the procedures described herein, are tested using the above procedures to determine stability of the formulations.

Example 20—In Vitro Comparison of Release Profile

Dissolution is performed at 37° C. in snapwells (6.5 mm diameter polycarbonate membrane with a pore size of 0.4 µm), 0.2 mL of a gel formulation described herein is placed into snapwell and left to harden, then 0.5 mL buffer is placed into reservoir and shaken using a Labline orbit shaker at 70 rpm. Samples are taken every hour (0.1 mL withdrawn and replace with warm buffer). Samples are analyzed for otic agent concentration by UV at 245 nm against an external calibration standard curve. Pluronic concentration is analyzed at 624 nm using the cobalt thiocyanate method. Relative rank-order of mean dissolution time (MDT) as a function of % P407 is determined A linear relationship between the formulations mean dissolution time (MDT) and the P407 concentration indicates that the otic agent is released due to the erosion of the polymer gel (poloxamer) and not via diffusion. A non-linear relationship indicates release of otic agent via a combination of diffusion and/or polymer gel degradation.

Alternatively, samples are analyzed using the method described by Li Xin-Yu paper [Acta Pharmaceutica Sinica 2008, 43(2):208-203] and Rank-order of mean dissolution time (MDT) as a function of % P407 is determined.

Formulations comprising conivaptan, SR-121463 or micronized lixivaptan, prepared according to the procedures described herein, are tested using the above procedure to determine the release profile of the otic agents.

Example 21—In Vitro Comparison of Gelation Temperature

The effect of Poloxamer 188 and an otic agent on the gelation temperature and viscosity of Poloxamer 407 formulations is evaluated with the purpose of manipulating the gelation temperature.

A 25% Poloxamer 407 stock solution in PBS buffer and the PBS solution described above are used. Poloxamer 188NF from BASF is used. An appropriate amount of otic agent is added to the solutions described in Table 5 to provide a 2% formulation of the otic agent.

TABLE 5

Preparation of samples containing poloxamer 407/poloxamer 188

| Sample | 25% P407 Stock Solution (g) | Poloxamer 188 (mg) | PBS Buffer (g) |
|---|---|---|---|
| 16% P407/10% P188 | 3.207 | 501 | 1.3036 |
| 17% P407/10% P188 | 3.4089 | 500 | 1.1056 |
| 18% P407/10% P188 | 3.6156 | 502 | 0.9072 |
| 19% P407/10% P188 | 3.8183 | 500 | 0.7050 |
| 20% P407/10% P188 | 4.008 | 501 | 0.5032 |
| 20% P407/5% P188 | 4.01 | 256 | 0.770 |

Mean dissolution time, viscosity and gel temperature of the above formulations are measured using procedures described herein.

An equation is fitted to the data obtained and can be utilized to estimate the gelation temperature of F127/F68 mixtures (for 17-20% F127 and 0-10% F68).

$T_{gel} = -1.8(\% F127) + 1.3(\% F68) + 53$

An equation is fitted to the data obtained and can be utilized to estimate the Mean Dissolution Time (hr) based on the gelation temperature of F127/F68 mixtures (for 17-25% F127 and 0-10% F68), using results obtained in examples above.

$MDT = -0.2(T_{gel}) + 8$

Formulations comprising conivaptan, SR-121463 or micronized lixivaptan are prepared by addition of an appropriate amount of otic agents to the solutions described in Table 5. The gel temperature of the formulations is determined using the procedure described above.

Example 22—Determination of Temperature Range for Sterile Filtration

The viscosity at low temperatures is measured to help guide the temperature range at which the sterile filtration needs to occur to reduce the possibility of clogging.

Viscosity measurements are performed using a Brookfield viscometer RVDV-II+P with a CPE-40 spindle rotated at 1, 5 and 10 rpm (shear rate of 7.5, 37.5 and 75 s$^{-1}$), equipped with a water jacketed temperature control unit (temperature ramped from 10-25° C. at 1.6° C./min).

The Tgel of a 17% Pluronic P407 is determined as a function of increasing concentration of otic agent. The increase in Tgel for a 17% pluronic formulation is estimated by:

$\Delta T_{gel} = 0.93 [\% \text{ otic agent}]$

Formulations comprising conivaptan, SR-121463 or micronized lixivaptan, prepared according to procedures described herein, are tested using the above procedure to determine the temperature range for sterile filtration. The effect of addition of increased amounts of otic agent on the Tgel, and the apparent viscosity of the formulations is recorded.

Example 23—Determination of Manufacturing Conditions

TABLE 6

Viscosity of potential formulations at manufacturing/filtration conditions.

| | Apparent Viscosity$^a$ (cP) | | |
|---|---|---|---|
| Sample | 5° C. below Tgel | 20° C. | Temperature @ 100 cP |
| Placebo | 52 cP @ 17° C. | 120 cP | 19° C. |
| 17% P407/2% otic agent | 90 cP @ 18° C. | 147 cP | 18.5° C. |
| 17% P407/6% otic agent | 142 cP @ 22° C. | 105 cP | 19.7° C. |

$^a$Viscosity measured at a shear rate of 37.5 s$^{-1}$

An 8 liter batch of a 17% P407 placebo is manufactured to evaluate the manufacturing/filtration conditions. The placebo is manufactured by placing 6.4 liters of DI water in a 3 gallon SS pressure vessel, and left to cool down in the refrigerator overnight. The following morning the tank is taken out (water temperature 5° C., RT 18° C.) and 48 g of sodium chloride, 29.6 g of sodium phosphate dibasic dehydrate and 10 g of sodium phosphate monobasic monohydrate is added and dissolved with an overhead mixer (IKA RW20 @ 1720 rpm). Half hour later, once the buffer is dissolved (solution temperature 8° C., RT 18° C.), 1.36 kg of poloxamer 407 NF (spectrum chemicals) is slowly sprinkled into the buffer solution in a 15 minute interval (solution temperature 12° C., RT 18° C.), then speed is increased to 2430 rpm. After an additional one hour mixing, mixing speed is reduced to 1062 rpm (complete dissolution).

The temperature of the room is maintained below 25° C. to retain the temperature of the solution at below 19° C. The temperature of the solution is maintained at below 19° C. up to 3 hours of the initiation of the manufacturing, without the need to chill/cool the container.

Three different Sartoscale (Sartorius Stedim) filters with a surface area of 17.3 $cm^2$ are evaluated at 20 psi and 14° C. of solution
1) Sartopore 2, 0.2 μm 5445307HS-FF (PES), flow rate of 16 mL/min
2) Sartobran P, 0.2 μm 5235307HS-FF (cellulose ester), flow rate of 12 mL/min
3) Sartopore 2 XLI, 0.2 μm 54453071S-FF (PES), flow rate of 15 mL/min Sartopore 2 filter 5441307H4-SS is used, filtration is carried out at the solution temperature using a 0.45, 0.2 μm Sartopore 2 150 sterile capsule (Sartorius Stedim) with a surface area of 0.015 $m^2$ at a pressure of 16 psi. Flow rate is measured at approximately 100 mL/min at 16 psi, with no change in flow rate while the temperature is maintained in the 6.5-14° C. range. Decreasing pressure and increasing temperature of the solution causes a decrease in flow rate due to an increase in the viscosity of the solution. Discoloration of the solution is monitored during the process.

TABLE 7

Predicted filtration time for a 17% poloxamer 407 placebo at a solution temperature range of 6.5-14° C. using Sartopore 2, 0.2 μm filters at a pressure of 16 psi of pressure.

| Filter | Size ($m^2$) | Estimated flow rate (mL/min) | Time to filter 8 L (estimated) |
| --- | --- | --- | --- |
| Sartopore 2, size 4 | 0.015 | 100 mL/min | 80 min |
| Sartopore 2, size 7 | 0.05 | 330 mL/min | 24 min |
| Sartopore 2, size 8 | 0.1 | 670 mL/min | 12 min |

Viscosity, Tgel and UV/Vis absorption is check before filtration evaluation. Pluronic UV/Vis spectra are obtained by a Evolution 160 UV/Vis (Thermo Scientific). A peak in the range of 250-300 nm is attributed to BHT stabilizer present in the raw material (poloxamer). Table 8 lists physicochemical properties of the above solutions before and after filtration.

TABLE 8

Physicochemical properties of 17% poloxamer 407 placebo solution before and after filtration

| Sample | Tgel (° C.) | Viscosity[a] @ 19° C. (cP) | Absorbance @ 274 nm |
| --- | --- | --- | --- |
| Before filtration | 22 | 100 | 0.3181 |
| After filtration | 22 | 100 | 0.3081 |

[a]Viscosity measured at a shear rate of 37.5 $s^{-1}$

The above process is applicable for manufacture of 17% P407 formulations, and includes temperature analysis of the room conditions. Preferably, a maximum temperature of 19° C. reduces cost of cooling the container during manufacturing. In some instances, a jacketed container is used to further control the temperature of the solution to ease manufacturing concerns.

Example 24—In Vitro Release of Otic Agent from an Autoclaved Micronized Sample

17% poloxamer 407/1.5% otic agent in TRIS buffer: 250.8 mg of sodium chloride (Fisher Scientific), and 302.4 mg of Tromethamine (Sigma Chemical Co.) is dissolved in 39.3 g of sterile filtered DI water, pH is adjusted to 7.4 with 1M HCl. 4.9 g of the above solution is used and an appropriate amount of micronized otic agent is suspended and dispersed well. 2 mL of the formulation is transferred into a 2 mL glass vial (Wheaton serum glass vial) and seald with 13 mm butyl styrene (kimble stoppers) and crimped with a 13 mm aluminum seal. The vial is placed in a Market Forge-sterilmatic autoclave (settings, slow liquids) and sterilized at 250° F. for 25 minutes. After the autoclaving the sample is left to cool down to room temperature. The vial is placed in the refrigerator and mixed while cold to homogenize the sample. Sample discoloration or precipitation after autoclaving is recorded.

Dissolution is performed at 37° C. in snapwells (6.5 mm diameter polycarbonate membrane with a pore size of 0.4 μm), 0.2 mL of gel is placed into snapwell and left to harden, then 0.5 mL PBS buffer is placed into reservoir and shaken using a Labline orbit shaker at 70 rpm. Samples are taken every hour [0.1 mL withdrawn and replaced with warm PBS buffer containing 2% PEG-40 hydrogenated castor oil (BASF) to enhance otic agent solubility]. Samples are analyzed for otic agent concentration by UV at 245 nm against an external calibration standard curve. The release rate is compared to other formulations disclosed herein. MDT time is calculated for each sample.

Solubilization of otic agent in the 17% poloxamer system is evaluated by measuring the concentration of the otic agent in the supernatant after centrifuging samples at 15,000 rpm for 10 minutes using an eppendorf centrifuge 5424. Otic agent concentration in the supernatant is measured by UV at 245 nm against an external calibration standard curve.

Formulations comprising conivaptan, SR-121463 or micronized lixivaptan, prepared according to the procedures described herein, are tested using the above procedures to determine release rate of the otic agent from each formulation.

Example 25—Release Rate or MDT and Viscosity of Formulation Containing Sodium Carboxymethyl Cellulose 17% Poloxamer 407/2% Otic Agent/1% CMC (Hercules Blanose 7M):

A sodium carboxymethylcellulose (CMC) solution (pH 7.0) in PBS buffer is prepared by dissolving 205.6 mg of sodium chloride (Fisher Scientific), 372.1 mg of sodium phosphate dibasic dihydrate (Fisher Scientific), 106.2 mg of sodium phosphate monobasic monohydrate (Fisher Scientific) in 78.1 g of sterile filtered DI water. 1 g of Blanose 7M CMC (Hercules, viscosity of 533 cP @ 2%) is sprinkled into the buffer solution and heated to ease solution, solution is then cooled down and 17.08 g poloxamer 407NF (Spectrum Chemicals) is sprinkled into the cold solution while mixing.

A formulation comprising 17% poloxamer 407NF/1% CMC/2% otic agent in PBS buffer is made adding/dissolving an appropriate amount of otic agent to 9.8 g of the above solution, and mixing until all the otic agent is completely dissolved.

17% Poloxamer 407/2% Otic Agent/0.5% CMC (Blanose 7M65):

A sodium carboxymethylcellulose (CMC) solution (pH 7.2) in PBS buffer is prepared by dissolving 257 mg of sodium chloride (Fisher Scientific), 375 mg of sodium phosphate dibasic dihydrate (Fisher Scientific), 108 mg of sodium phosphate monobasic monohydrate (Fisher Scientific) in 78.7 g of sterile filtered DI water. 0.502 g of Blanose 7M65 CMC (Hercules, viscosity of 5450 cP @ 2%) is sprinkled into the buffer solution and heated to ease solution, solution is then cooled down and 17.06 g poloxamer 407NF (Spectrum Chemicals) is sprinkled into the cold solution while mixing. A 17% poloxamer 407NF/1% CMC/2% otic agent solution in PBS buffer is made adding/dissolving an appropriate amount of otic agent to 9.8 g of the above solution, and mixing until the otic agent is completely dissolved.

17% Poloxamer 407/2% Otic Agent/0.5% CMC (Blanose 7H9):

A sodium carboxymethylcellulose (CMC) solution (pH 7.3) in PBS buffer is prepared by dissolving 256.5 mg of sodium chloride (Fisher Scientific), 374 mg of sodium phosphate dibasic dihydrate (Fisher Scientific), 107 mg of sodium phosphate monobasic monohydrate (Fisher Scientific) in 78.6 g of sterile filtered DI water, then 0.502 g of Blanose 7H9 CMC (Hercules, viscosity of 5600 cP @ 1%) is sprinkled to the buffer solution and heated to ease solution, solution is then cooled down and 17.03 g poloxamer 407NF (Spectrum Chemicals) is sprinkled into the cold solution while mixing. A 17% poloxamer 407NF/1% CMC/ 2% otic agent solution in PBS buffer is made adding/ dissolving an appropriate amount of otic agent to 9.8 of the above solution, and mixing until the otic agent is completely dissolved.

Viscosity measurements are performed using a Brookfield viscometer RVDV-II+P with a CPE-40 spindle rotated at 0.08 rpm (shear rate of 0.6 s$^{-1}$), equipped with a water jacketed temperature control unit (temperature ramped from 10-34° C. at 1.6° C./min) Tgel is defined as the inflection point of the curve where the increase in viscosity occurs due to the sol-gel transition.

Dissolution is performed at 37° C. in snapwells (6.5 mm diameter polycarbonate membrane with a pore size of 0.4 µm). 0.2 mL of gel is placed into snapwell and left to harden, then 0.5 mL PBS buffer is placed into reservoir and shaken using a Labline orbit shaker at 70 rpm. Samples are taken every hour, 0.1 mL withdrawn and replaced with warm PBS buffer. Samples are analyzed for otic agent concentration by UV at 245 nm against an external calibration standard curve. The release rate is compared to the formulations disclosed in above examples, and MDT time is calculated for each of the above formulations.

Formulations comprising conivaptan, SR-121463 or micronized lixivaptan, prepared according to procedures described above, are tested using the above procedures to determine relationship between release rate and/or mean dissolution time and viscosity of formulation containing sodium carboxymethyl cellulose. Any correlation between the mean dissolution time (MDT) and the apparent viscosity (measured at 2° C. below the gelation temperature) is recorded.

Example 26—Application of an Enhanced Viscosity Aural Pressure Modulating Agent Formulation onto the Round Window Membrane A formulation according to Example 2 is prepared and loaded into 5 ml siliconized glass syringes attached to a 15-gauge luer lock disposable needle. Lidocaine is topically applied to the tympanic membrane, and a small incision made to allow visualization into the middle ear cavity. The needle tip is guided into place over the round window membrane, and the aural pressure modulator formulation applied directly onto the round-window membrane.

Example 27—In Vivo Testing of Intratympanic Injection of Aural Pressure Modulating Agent Formulation in a Guinea Pig A cohort of 21 guinea pigs (Charles River, females weighing 200-300 g) is intratympanically injected with 50 µL of different P407-DSP formulations described herein, containing 0 to 50% otic agent. The gel elimination time course for each formulation is determined A faster gel elimination time course of a formulation indicates lower mean dissolution time (MDT). Thus the injection volume and the concentration of an aural pressure modulator in a formulation are tested to determine optimal parameters for preclinical and clinical studies.

Example 28—In Vivo Extended Release Kinetics

A cohort of 21 guinea pigs (Charles River, females weighing 200-300 g) is intratympanically injected with 50 µL 17% Pluronic F-127 formulation buffered at 280 mOsm/ kg and containing 1.5% to 35% aural pressure modulating agent by weight of the formulation. Animals are dosed on day 1. The release profile for the formulations is determined based on analysis of the perilymph.

Example 29—Evaluation of VP2 Antagonist Formulations in an Endolymphatic Hydrops Animal Model The following procedure is used to determine the efficacy of the thermoreversible gel formulation of lixivaptan as prepared in Example 1.
Materials and Methods Thirty-five Hartley guinea pigs with a positive Preyer's reflex and weighing about 300 g are used. Five animals, which serve as controls (normal ear group), are fed for 5 weeks with neither operation nor treatment, and the remaining 30 serve as experimental animals. All experimental animals received electro-cauterization of the endolymphatic sac (Lee et al., Acta Otolaryngol. (1992) 112:658-666; Takeda et al., Equilib. Res. (1993) 9:139-143). Four weeks after surgery, these animals are divided into three groups of non-infusion hydropic ears, vehicle-treated hydropic ears and lixivaptan-treated hydropic ears, consisting of 10 animals each. The group of non-infusion hydropic ears receive no treatment except for electro-cauterization of the endolymphatic sac. In the groups of vehicle-treated hydropic ears and lixivaptan-treated hydropic ears, the thermoreversible gel formulation is applied to the round window membrane. One week after administration of the composition, all animals are sacrificed for assessment of the changes of the endolymphatic space. All animals are left undisturbed and freely moving in individual cages in a quiet room throughout the period, except during experimental procedures.

To assess the changes to the endolymphatic space, all animals are transcardially perfused with physiological saline solution under deep anesthesia by a peritoneal injection of pentobarbital, and fixation is performed with 10% formalin. The left temporal bones are removed and postfixed in 10% formalin solution for 10 days or more. Thereafter, they are decalcified with 5% trichloroacetic acid for 12 days and dehydrated in a graded ethanol series. They are embedded in paraffin and celloidin. The prepared blocks are cut horizontally into 6 µm sections. The sections are stained with hematoxylin and eosin and observed under a light microscope. Quantitative assessment of changes of the endolymphatic space is performed according to the method of Takeda (Takeda et al., Hearing Res. (2003) 182:9-18).

Example 30—Evaluation of Lixivaptan Administration in Meniere's Patients

Study Objective

The primary objective of this study will be to assess the safety and efficacy of Lixivaptan (100 mg) in ameliorating Meniere's Disease in human subjects.

Methods

Study Design

This will be a phase 3, multicentre, double-blind, randomised, placebo-controlled, parallel group study comparing lixivaptan administration (100 mg) to placebo in the treatment of endolymphatic hydrops. Approximately 100 subjects will be enrolled in this study, and randomised (1:1) to 1 of 2 treatment groups based on a randomisation sequence prepared by the sponsor. Each group will receive either 100 mg lixivaptan+meclizine or meclizine treatment alone.

Subjects who do not complete the study will not be replaced. All patients will receive daily meclizine treatment for 8 weeks. Patients receiving the study drug (Lixivaptan 100 mg or matching placebo) will be administered a gel formulation directly onto the subjects' round window membrane for 8 weeks. Each patient will receive a vestibular and hearing evaluation before each treatment with meclizine and the study drug.

While preferred embodiments of the present invention have been shown and described herein, such embodiments are provided by way of example only. Various alternatives to the embodiments described herein are optionally employed in practicing the inventions. It is intended that the following claims define the scope of the invention and that methods and structures within the scope of these claims and their equivalents be covered thereby.

We claim:

1. An intratympanic composition for use in the treatment of an otic disease or condition, the intratympanic composition comprising:
   a multiparticulate and non-microencapsulated aural pressure modulating agent, or pharmaceutically acceptable salt thereof; and
   an auris acceptable thermoreversible hydrogel,
   wherein sustained release of the aural pressure modulating agent into an inner ear occurs for a period of at least 5 days after a single administration, and
   wherein the composition has a non-gel state at room temperature.

2. The intratympanic composition of claim 1, wherein the auris acceptable hydrogel has a gelation viscosity between about 15,000 cP and about 1,000,000 cP.

3. The intratympanic composition of claim 1, wherein the auris acceptable hydrogel is capable of being injected by a 18-31 gauge needle or cannula through the tympanic membrane.

4. The intratympanic composition of claim 1, wherein the intratympanic composition has an osmolarity of from about 150 mOsm/L to about 1000 mOsm/L.

5. The intratympanic composition of claim 1, wherein the multiparticulate and non-microencapsulated aural pressure modulating agent is essentially in the form of micronized particles.

6. The intratympanic composition of claim 1, wherein the intratympanic composition has a pH between 7.0 and 8.0.

7. The intratympanic composition of claim 1, wherein the aural pressure modulating agent is selected from the group consisting of vasopressin receptor modulators, prostaglandins, prostaglandin modulators, estrogen-related receptor beta modulators, osmotic diuretics, and calcium channel blockers.

8. The intratympanic composition of claim 7, wherein the aural pressure modulating agent is a vasopressin receptor modulator.

9. The intratympanic composition of claim 8, wherein the vasopressin receptor modulator is a VP2 receptor agonist selected from the group consisting of OPC-51803, WAY-VNA-932, OPC-31260, SR-121463, tolvaptan, conivaptan, and lixivaptan.

10. The intratympanic composition of claim 7, wherein the aural pressure modulating agent is a prostaglandin or a prostaglandin modulator.

11. The intratympanic composition of claim 10, wherein the aural pressure modulating agent is a prostaglandin modulator selected from the group consisting of a latanoprost, travoprost, unoprostone, minprostin F2-alpha, bimtoprost and SQ29548.

12. The intratympanic composition of claim 7, wherein the aural pressure modulating agent is an estrogen-related receptor beta modulator.

13. The intratympanic composition of claim 7, wherein the aural pressure modulating agent is an osmotic diuretic selected from the group consisting of erythritol, mannitol, glucose, isosorbide, glycerol and urea.

14. The intratympanic composition of claim 7, wherein the aural pressure modulating agent is a calcium channel blocker selected from the group consisting of lomerizine, cinnarizine, flunarizine, and nimodipine.

15. The intratympanic composition of claim 1, wherein sustained release of the aural pressure modulating agent into the cochlea occurs for a period of at least 7 days after a single administration.

16. The intratympanic composition of claim 1, wherein sustained release of the aural pressure modulating agent into the cochlea occurs for a period of at least 10 days after a single administration.

* * * * *